United States Patent
Cheng et al.

(10) Patent No.: US 10,344,049 B2
(45) Date of Patent: Jul. 9, 2019

(54) SUBSTITUTED STEROIDS FOR THE TREATMENT OF CANCER

(71) Applicant: AQUAVAN TECHNOLOGY CO., LTD., Taipei (TW)

(72) Inventors: Shi-Yie Cheng, Taipei (TW); Yao-Ting Wang, Taipei (TW); Kuo-Tang Tseng, Taipei (TW); Wen-Hung Chen, Taipei (TW); Hsin Ju Wang, Taipei (TW)

(73) Assignee: AQUAVAN TECHNOLOGY CO., LTD, Taipei (TW)

( * ) Notice: Subject to any disclaimer, the term of this patent is extended or adjusted under 35 U.S.C. 154(b) by 0 days.

(21) Appl. No.: 15/842,843

(22) Filed: Dec. 14, 2017

(65) Prior Publication Data

US 2018/0298050 A1 Oct. 18, 2018

(30) Foreign Application Priority Data

Apr. 12, 2017 (TW) .............................. 106112149 A
Oct. 31, 2017 (TW) .............................. 106137494 A

(51) Int. Cl.
| | |
|---|---|
| *A61K 31/575* | (2006.01) |
| *C07J 1/00* | (2006.01) |
| *C07J 71/00* | (2006.01) |
| *A61P 35/00* | (2006.01) |
| *C07J 9/00* | (2006.01) |
| *A61K 31/58* | (2006.01) |
| *A61K 36/42* | (2006.01) |

(52) U.S. Cl.
CPC ......... *C07J 71/0026* (2013.01); *A61K 31/575* (2013.01); *A61K 31/58* (2013.01); *A61K 36/42* (2013.01); *A61P 35/00* (2018.01); *C07J 9/00* (2013.01)

(58) Field of Classification Search
CPC ................................ A61K 31/575; C07J 1/00
USPC .......................................... 514/182; 552/623
See application file for complete search history.

(56) References Cited

U.S. PATENT DOCUMENTS

2017/0152285 A1* 6/2017 Tsai ..................... A61K 31/575

* cited by examiner

Primary Examiner — Douglas M Willis

(57) ABSTRACT

A compound and pharmaceutically acceptable salts thereof for treating cancer, having a structure represented by the following formula (I) or formula (II):

formula (I)

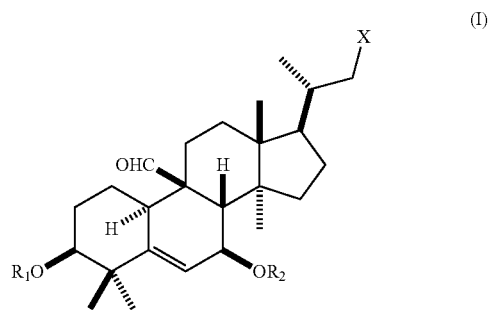

formula (II)

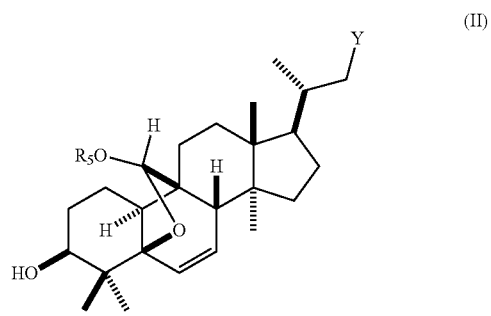

in which X and Y each individually represent:

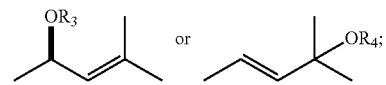

$R_1$, $R_2$, $R_3$, $R_4$, and $R_5$ individually represents hydrogen atom, acyl having 20 or less carbon atoms, alkyl having 20 or less carbon atoms, alkanoyl having 20 or less carbon atoms, aroyl having 20 or less carbon atoms, aryl having 20 or less carbon atoms, aralkyl having 20 or less carbon atoms, sulfonyl having 20 or less carbon atoms, phosphonyl having 20 or less carbon atoms, or haloacyl having 20 or less carbon atoms.

6 Claims, 26 Drawing Sheets

SUBSTITUTED STEROIDS FOR THE TREATMENT OF CANCER

CROSS-REFERENCE TO RELATED APPLICATIONS

The present application claims the benefit of Taiwanese Patent Application No. 106112149 filed on Apr. 12, 2017 and Taiwanese Patent Application No. 106137494 filed on Oct. 31, 2017, the entire contents of which are hereby incorporated by reference.

BACKGROUND OF THE INVENTION

1. Field of the Invention

The present invention relates to a compound for treating cancer, and pharmaceutically acceptable salts thereof, and more particularly to a compound containing a component effective to treat cancers isolated from balsam pear, pharmaceutically acceptable salts thereof, and derivatives thereof.

2. Description of the Related Art

In recent decades, with aging populations, affliction with cancers or malignancies has become one of top 10 causes of death in Taiwan. Medically called "tumors" include benign and malignant tumors, and generally refer to abnormal cell proliferation to form neoplasms, and even affect surrounding or distant cell tissues, affecting normal physiological functions. Common cancers include liver cancer, rectal cancer, colorectal cancer, esophageal cancer, gastric cancer, leukemia, malignant lymphoma, nasopharyngeal cancer, brain tumor, lung cancer, breast cancer, cervical cancer, hematologic cancer, and bone cancer etc. Of them, lung cancer, gastric cancer, and liver cancer are the strongest in destruction power, accounting for 18%, 10% and 9% of the number of cancer deaths respectively.

Various malignant tumors are typically collectively referred to as "cancers". In this case, cancer cells are in uncontrolled state in growth and division, and can invade normal tissues and affect surrounding tissues, and be metastasized to sites away from its origin via circulatory system, lymphatic system or lumen in body, thereby presenting a serious challenge on human health and life security. Methods for treatment of cancers may be generally divided into surgery, chemotherapy, radiotherapy, targeted therapy, immunotherapy, hormonal therapy, cryotherapy, thermotherapy, anti-angiogenic therapy, as well as TCM therapy, CMH therapy etc.

Among the various treatment methods of cancers, surgery, radiotherapy, and chemotherapy are main means of clinical treatment at present, and different therapies are adapted according to the type, position and stage of cancer in a patient. Surgical resection is mainly used to remove cell tissues at cancer site; and radiotherapy and chemotherapy also have damage to normal cells while killing tumor cells, with high side effect, poor quality of life, and low survival rate in patients. However, surgical resection, radiotherapy and chemotherapy all are an irreversible approach in which human body cells, tissues and even organs are damaged.

With exploration achievements for cell death phenomena and molecular mechanisms, an entirely new understanding on screening of anti-cancer agents has been generated, and therefore, a method which causes less irreversible secondary damage to cancer patients, for example, an approach treating a particular signaling pathway of tumor cells or a particular target site of cancer cells using an agent containing Chinese herbal medicine or extracted ingredients thereof, is being paid more and more attention.

Balsam pear, commonly grown in tropical and sub-tropical regions, is a plant of the Cucurbitaceae family, called as *Momordica charantia* L. in a scientific name, and has many different varieties or lines in various locations due to natural evolution or artificial hybridization. In Taiwan, commonly called "balsam pear" generally refers to bailian kugua or "dabai kugua" sold on the market as foods at home. Bitter gourd, which has become popular in recent years, is also a balsam pear, having the same scientific name as bailian kugua and belonging to a different line from bailian kugua.

One of the most common functions of balsam pear is fire-downbearing. It is considered in traditional Chinese herbal medicine that a whole plant of balsam pear can be used as medicine, and is cold in nature and tastes bitter, can be absorbed in heart, spleen, and stomach, has summer heat clearing and antipyretic effects, and can improve eyesight and remove toxic substances. In addition, in traditional medicine in some countries and regions such as China, Japan, South East Asia, India, Africa, Latin America, balsam pear can also be used to treat diabetes, and generally local varieties are used. Even balsam pear is referred to as plant insulin in some locations.

Recently, it has been proved through modern scientific tests by scientists that balsam pear indeed has hypoglycemic function. It has also been found from further research that active ingredients such as proteins, polypeptides, alkaloids, triterpene compounds, and steroid compounds in balsam pear, in addition to hypoglycemic effect, also have antiviral, antibacterial, anti-oxidant, anti-inflammatory, immunomodulatory, hypolipidemic, and other effects.

Moreover, the present inventors have found that momordicin I contained in balsam pear and derivatives thereof have inhibition effect on the growth of cancer cells, and could be used as active ingredient in an agent for treating or preventing cancers.

BRIEF SUMMARY OF THE INVENTION

The following presents a simplified summary of the disclosure in order to provide a basic understanding to the reader. This summary is not an extensive overview of the disclosure and it does not identify key/critical elements of the invention or delineate the scope of the invention.

As described above, the present invention is based on an unexpected finding that a particular momordicin I and derivatives thereof, when used in treating different cancers, can provide surprisingly good results which is much better than those with common anticancer agents, including reduction and regulation of oncogenic activity, prevention and even reversal of proliferation of cancer cells, thereby achieving prevention and treatment of cancers and tumor metastases. Therefore, momordicin I derivatives can be used in development of an agent for treating or preventing inflammation and/or tumor-related diseases.

That is, the present invention can provide a compound for treating cancer, and pharmaceutically acceptable salts thereof, having a structure represented by the following formula (I) or formula (II):

formula (I)

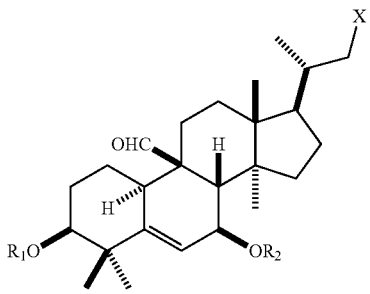

formula (II)

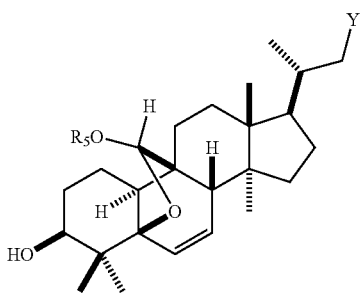

in which X and Y each individually represent

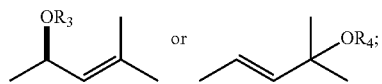

R₁ represents hydrogen atom, acyl having 20 or less carbon atoms, alkanoyl having 20 or less carbon atoms, aroyl having 20 or less carbon atoms, sulfonyl having 20 or less carbon atoms, phosphonyl having 20 or less carbon atoms, or haloacyl having 20 or less carbon atoms; $R_2$ represents hydrogen atom, acyl having 20 or less carbon atoms, alkyl having 20 or less carbon atoms, aryl having 20 or less carbon atoms, aralkyl having 20 or less carbon atoms, or heteroatom-containing alkyl having 20 or less carbon atoms; $R_3$ represents hydrogen atom, acyl having 20 or less carbon atoms, alkanoyl having 20 or less carbon atoms, aroyl having 20 or less carbon atoms, sulfonyl having 20 or less carbon atoms, phosphonyl having 20 or less carbon atoms, or haloacyl having 20 or less carbon atoms; $R_4$ represents hydrogen atom, or alkyl having 20 or less carbon atoms, aryl having 20 or less carbon atoms, aralkyl having 20 or less carbon atoms, or heteroatom-containing alkyl having 20 or less carbon atoms; and $R_5$ represents alkyl having 20 or less carbon atoms, aryl having 20 or less carbon atoms, aralkyl having 20 or less carbon atoms, or heteroatom-containing alkyl having 20 or less carbon atoms.

According to an embodiment of the present invention, provided are a compound for treating cancer, and pharmaceutically acceptable salts thereof, where the acyl, alkanoyl, aroyl, sulfonyl, phosphonyl, and haloacyl each further have a substituent, where the substituent is at least one selected from the group consisting of halogen, hydroxyl, alkoxy, phenyl, naphthyl, isobenzofuranyl, isobenzothienyl, and isoquinolyl, preferably at least one of halogen, hydroxyl, alkyl, alkoxy, and phenyl, more preferably at least one of halogen, hydroxyl, alkyl, and alkoxy, most preferably at least one of hydroxyl, alkyl, and alkoxy.

According to an embodiment of the present invention, provided are a compound for treating cancer, and pharmaceutically acceptable salts thereof, where the acyl is generally acyl having 20 or less carbon atoms, preferably acyl having 15 or less carbon atoms, more preferably acyl having 10 or less carbon atoms, particularly preferably having 5 or less carbon atoms, most preferably acetyl.

According to an embodiment of the present invention, provided are a compound for treating cancer, and pharmaceutically acceptable salts thereof, where the alkyl is generally alkyl having 20 or less carbon atoms, preferably alkyl having 15 or less carbon atoms, more preferably alkyl having 10 or less carbon atoms, particularly preferably having 5 or less carbon atoms, most preferably methyl.

According to an embodiment of the present invention, provided are a compound for treating cancer, and pharmaceutically acceptable salts thereof, where the alkyl is alkyl further having a substituent, where the substituent is at least one selected from the group consisting of halogen, hydroxyl, alkanoyloxy, alkoxy, phenyl, naphthyl, isobenzofuranyl, isobenzothienyl, and isoquinolyl, preferably at least one of halogen, hydroxyl, alkanoyloxy, alkoxy, phenyl, naphthyl, and isobenzofuranyl, and more preferably at least one of hydroxyl, alkanoyloxy, alkoxy, and phenyl, most preferably at least one of hydroxyl, alkanoyloxy, and alkoxy.

According to an embodiment of the present invention, provided are a compound for treating cancer, and pharmaceutically acceptable salts thereof, where the aryl is aryl further having a substituent, where the substituent is at least one selected from the group consisting of halogen atom, C1-4 alkyl, C1-20 alkoxy, and halogenated C1-20 alkoxy, preferably at least one of halogen atom, C1-4 alkyl, C1-20 alkoxy, and more preferably at least one of halogen atom and C1-4 alkyl.

According to an embodiment of the present invention, provided are a compound for treating cancer, and pharmaceutically acceptable salts thereof, where the aralkyl further has a substituent, where the substituent is at least one selected from the group consisting of halogen, hydroxyl, alkanoyloxy, alkoxy, phenyl, naphthyl, isobenzofuranyl, isobenzothienyl, and isoquinolyl, preferably at least one of halogen, hydroxyl, alkanoyloxy, alkoxy, phenyl, isobenzofuranyl, and isobenzothienyl, and more preferably at least one of halogen, hydroxyl, alkanoyloxy, and alkoxy, most preferably at least one of hydroxyl, alkanoyloxy, and alkoxy.

According to an embodiment of the present invention, provided are a compound for treating cancer, and pharmaceutically acceptable salts thereof, where the heteroatom-containing alkyl has at least one heteroatom selected from the group consisting of N, O, S, P, B, Cl, Br, and I, preferably at least one of N, O, S, P, Cl, and Br, and more preferably at least one of N, O, and P, most preferably at least one of N and O.

According to an embodiment of the present invention, provided is a compound for treating cancer, and pharmaceutically acceptable salts thereof, where the cancer is at least one of malignant glial brain tumor, liver cancer, colorectal cancer, lung cancer, hematologic cancer, and breast cancer.

According to an embodiment of the present invention, provided is a pharmaceutical composition for treating cancer, at least comprising a compound for treating cancer as described above and pharmaceutically acceptable salts thereof, as well as a carrier and/or any of a diluent, a vehicle and an adjuvant.

According to an embodiment of the present invention, provided is a pharmaceutical composition for treating cancer, where the compound is in an amount of about 0.1% to 99% (by weight) based on the total weight of the pharmaceutical composition, preferably at least 1% (by weight) based on the total weight of the pharmaceutical composition, more preferably at least 5% (by weight) based on the total weight of the pharmaceutical composition, particularly preferably at least 10% (by weight) based on the total weight of the pharmaceutical composition, most preferably at least 25% (by weight) based on the total weight of the pharmaceutical composition.

One or more examples of the disclosure will be described in detail below in the Detailed Description of the Invention. The foregoing features of the disclosure will become more apparent from the following detailed description and the appended claims. It should be noted that the foregoing general description and the following detailed description are intended to be exemplary only for illustrative purposes and are not intended to limit the scope of the disclosure.

BRIEF DESCRIPTION OF THE SEVERAL VIEWS OF DRAWING

FIG. 1 is a flow diagram illustrating separation of compounds 1, 2, and 11 to 14 in preparative example 1 according to the present invention.

DETAILED DESCRIPTION OF THE INVENTION

Figure 1:
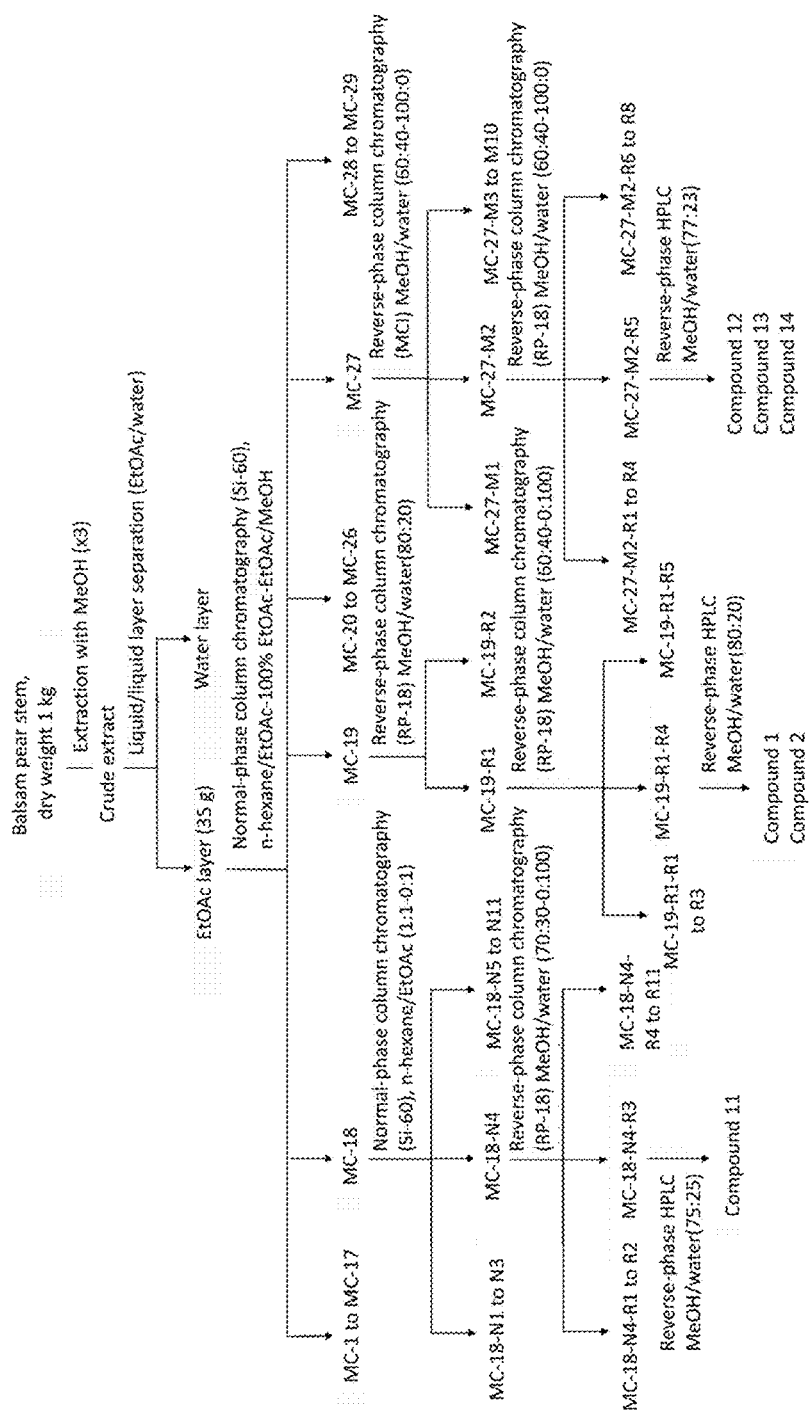

Herein, all technical and scientific terms used herein have the same meaning as commonly understood by one of ordinary skill in the art to which this invention belongs. Further, unless otherwise clearly contradicted by context, singular terms used herein shall include pluralities and plural terms shall include the singular.

Herein, the term "alkyl" means a hydrocarbyl group which has 1 to 20 carbon atoms and is straight, branched, and/or cyclic ("cycloalkyl") (i.e., 1-10, 1-9, 1-8, 1-7, 1-6, 1-5, 1-4, 1-3, 1-2, or 1 carbon atom). An alkyl structure containing 1 to 4 carbon atoms is referred to as "lower alkyl". For example, the alkyl group includes methyl, ethyl, propyl, isopropyl, n-butyl, t-butyl, isobutyl, 2-isopropyl-3-methylbutyl, pentyl, pent-2-yl, hexyl, isohexyl, heptyl, kept-2-yl, 4,4-dimethylpentyl, octyl, 2,2,4-trimethylpentyl, nonyl, decyl, undecyl, and dodecyl. The cycloalkyl structure may be monocyclic or polycyclic, and examples thereof include cyclopropyl, cyclobutyl, cyclopentyl, and cyclohexyl. Unless otherwise defined, an alkyl group in each example individually contains an optional substituent, i.e. unsubstituted alkyl or substituted alkyl. In a particular embodiment, the alkyl group is substituted C2-10 alkyl.

Herein, the term "acyl" means a moiety remaining after the removal of hydroxyl (—OH) from the molecule of an inorganic or organic oxoacid. Examples of the acyl group include, but not limited to, formyl, acetyl, propionyl, butyryl, i-butyryl, methylsulfonyl, ethylsulfonyl, n-propylsulfonyl, iso-propylsulfonyl, n-butylsulfonyl, iso-butylsulfonyl, tert-butylsulfonyl), and the like.

Herein, the term "alkoxy" means —O— alkyl group. Examples of the alkyl group include, but not limited to —OCH3, —OCH2CH3, —O(CH2) 2CH3, —O(CH2) 3CH3, —O(CH2)4CH3, and —O(CH2)5CH3. The term "lower alkoxy" means —O— (lower alkyl), such as —OCH3 and —OCH2CH3.

Herein, the term "aryl" means an aromatic ring or a partially aromatic ring system consisting of C and H atoms. An aryl group may contain a plurality of rings bonded or fused to each other. Examples of the aryl group include naphthyl and phenyl. Unless otherwise indicated, an aryl group in each example individually contains an optional substituent, i.e. unsubstituted aryl or substituted aryl. In a particular embodiment, the aryl group is substituted phenyl. In another embodiment, the aryl group is substituted naphthyl.

Herein, the "heteroaryl" means that at least one carbon atom in an aryl group carries a heteroatom (e.g., N, O, or S). Examples thereof include benzofuranyl, benzothienyl, quinolyl, benzodioxolyl, furyl, and thienyl.

Herein, the term "aralkyl" means that an alkyl group is bound to an aryl group.

Unless otherwise defined herein, the term "halogen (halo)" includes F, Cl, Br, and I.

Unless otherwise defined herein, the term "substituted", when used to describe a chemical structure or chemical group, means that one or more hydrogen are substituted with an atom, chemical group, or functional group, i.e., but not limited to, —OH, —CHO, alkoxy, acyl (e.g., —OAc), alkenyl, alkyl (e.g., methyl, ethyl, propyl, t-butyl), aryl, aryloxy, halo, or haloalkyl (e.g., —CCl3, —CF3, —C(CF3) 3).

In a particular embodiment, the term "substituted", when used to describe a chemical structure or chemical group, means that one or more hydrogen atoms in the structure or group of a derivative are substituted with one or more of alkoxy, acyl, alkyl, aryl, halo, haloalkyl, or hydroxyl.

Unless otherwise defined herein, a "therapeutically effective amount" of a compound means the amount of a compound that, when used in treating or managing a disease or condition, is sufficient to provide a therapeutic effect or to delay or reduce a symptom related to the disease or condition. A therapeutically effective amount of a compound means an amount, alone or in combination with other agents, sufficient to provide a therapeutic effect of treating or managing a disease or disorder. The term "therapeutically effective amount" can encompass an amount that improves overall therapeutic effect, reduces or avoids symptoms of a disease or condition, or enhances the efficacy of another therapeutic agent.

Unless otherwise defined herein, the term "treat, treating or treatment" means an action of administration to a patient with a particular disease or disorder, where the action can reduce the disease or disorder of the patient, or the severity of one or more symptoms, or slow or delay the progress of the disease or disorder.

It should be noted that if the stereochemistry of a structure or a portion of a structure is not indicated with, for example, bold or dashed lines, the structure or portion of the structure is to be interpreted as encompassing all stereoisomers of it. Similarly, where a compound contains one or more asymmetric centers and its name does not specifically define the stereochemistry encompassed by these asymmetric centers, the compound should be interpreted as encompassing its pure optical isomers and mixtures thereof. Furthermore, any atom with unsatisfied valences shown in the figures is assumed to have the sufficient hydrogen atoms to satisfy the valences.

Notwithstanding that the numerical ranges and parameters setting forth the broad scope of the invention are approximations, the numerical values set forth in the specific examples are presented herein as precisely as possible. Any numerical value, however, inherently contains certain errors necessarily resulting from the standard deviation found in its respective testing measurement. Herein, the term "about" generally means that an actual value is within 10%, 5%, 1%, or 0.5% above and below a particular value or range. Alternatively, the term "about" indicates that the actual value falls within an acceptable standard error of the mean when considered by one of ordinary skill in the art. Except in the Examples, or where otherwise explicitly indicated, all ranges, amounts, values, and percentages used herein (for example, for describing amounts of materials, time, temperature, operation conditions, amount ratio, and the like) are understood to be modified by the word "about". Thus, unless expressly stated to the contrary, the numerical parameters disclosed in this specification and the appended claims are all approximations and, if required, may vary. At the very least, each numerical parameter should at least be construed in light of the number of reported significant digits and by applying ordinary rounding techniques.

The compounds of this invention are momordicin I derivatives which may contain one or more stereogenic centers; and therefore, the compounds are present as different isomers, for example, a racemic mixture of enantiomers and/or mixture of diastereomers. The present invention encompasses enantiomers of these compounds, and a mixture of these enantiomers and/or diastereomers. Enantiomers may be prepared by asymmetric synthesis, or separated using conventional techniques, e.g., crystallization, chromatography, and separation with a resolving agent. High-performance liquid chromatography (HPLC) is a preferred method for separating enantiomers from a racemic mixture. Additionally, two enantiomers may also be separated from each other from racemic isomers through a reaction with the optically active form of a resolving agent in a solvent. Depending on the optical form of the resolving agent used, one isomer of two enantiomers may be separated as an insoluble salt, and compared to the isomer remaining in the solution, the separated isomer has high yield and high optical purity.

The present invention further includes a mixture of stereoisomers of the compounds. Furthermore, the present invention also encompasses conformational isomers (i.e., cis and trans isomers, with or without double bonds) of the compounds, including a mixture of the isomers, pure isomers, or substantially pure form.

The pharmaceutical composition disclosed in this invention is suitable for treating various cancers, for example, such as, but not limited to, liver cancer, colorectal cancer, esophageal cancer, gastric cancer, leukemia, malignant lymphoma, nasopharyngeal cancer, malignant glial brain tumor, lung cancer, breast cancer, cervical cancer, bone cancer, rectal cancer, liver cancer, breast cancer, or hematologic cancer, and preferably, liver cancer, colorectal cancer, esophageal cancer, gastric cancer, leukemia, malignant lymphoma, nasopharyngeal cancer, malignant glial brain tumor, lung cancer, breast cancer, cervical cancer, hematologic cancer, or bone cancer.

The pharmaceutical composition disclosed in this invention may be prepared by well-known pharmaceutical processes. In one implementation aspect of this invention, the pharmaceutical composition disclosed in this invention may be administered by way of any appropriate dosing route, for example, systemic administration modes by oral administration as capsules, suspensions, or dragees, or by parenteral administration, for example, as intramuscular injection, intravenous injection, subcutaneous injection, or intraperitoneal injection. In addition, in some embodiments, the pharmaceutical composition disclosed in this invention may also be administered through transmucosal or transdermal means, for example, topical dermal application, or bronchial, nasal, or oral inhalation, or instillation as nasal drops; and may also be administered rectally.

For oral administration, the pharmaceutical composition disclosed in this invention may be administered with excipients or may be administered without excipients. Also, the pharmaceutical composition of this invention may also be formulated into dragees as a solid dosage form containing various auxiliaries, disintegrants, granular binders, or lubricants therein. Additionally, in an example, lactose or high molecular weight polyethylene glycols may also be used. In addition, optionally, the rate of release of any pharmaceutically active ingredient may be further improved with a coating or cladding, for example, enteric coating. In other examples, the pharmaceutical composition of this invention may also be formulated into a liposome structure or biomimetic extracellular matrix system structure, or may be filled into hard and soft gelatin capsules, or may be encapsulated into biodegradable granules in kits.

Also, in the present invention, a pharmaceutically acceptable excipient means one that is compatible with other ingredients of the pharmaceutical formulation and compatible with organisms, for example, encapsulating materials, or various additives such as absorption enhancer, antioxidant, binder, buffer, coating agent, coloring agent, diluent, disintegrant, emulsifier, supplement, filler, flavoring agent, humectant, lubricant, perfume, preservative, propellant, release agent, sterilization agent, sweeting agent, solubilizing agent, wetting agent, and mixtures thereof.

Examples of auxiliaries suitable for use in the present invention may be, for example, microcrystalline cellulose, calcium carbonate, di calcium phosphate, or glycine. Examples of disintegrants suitable for use in the present invention may be, for example, starch, alginic acids, or certain silicates. Examples of granular binders suitable for use in the present invention may be, for example, polyvinylpyrrolidone, sucrose, gelatin, or acacia. Examples of granular binders suitable for use in the present invention may be, for example, magnesium stearate, sodium lauryl sulfate, or talc. Examples of excipients suitable for use in the present invention may be, for example, lactose, sucrose, mannitol, sorbitol, maize starch, wheat starch, rice starch, potato starch, gelatin, or gum tragacanth.

In some embodiments, the pharmaceutical composition of this invention is formulated into a liquid dosage form suitable for oral administration, for example, oral suspensions, emulsions, microemulsions, and/or elixirs. For such a liquid dosage form, the active ingredients of the pharmaceutical composition of this invention may be further formulated with various sweeting agents or flavoring agents, coloring agents or dyes, if desired, with addition of emulsifiers and/or suspending agents, or diluents such as water, alcohol, propylene glycol, or glycerine, or buffers used to maintain the pH.

Also, in other embodiments, the liquid formulation containing the pharmaceutical composition of this invention is made into sterile injectable solutions or suspensions; for example, made into solutions suitable for administration by intravenous, intramuscular, subcutaneous, or intraperitoneal injection.

Examples of diluents suitable for use in the sterile injectable solutions or suspensions may be, for example, but not limited to, 1,3-butanediol, mannitol, water, Ringer's solution, or isotonic sodium chloride solution; fatty acids such as oleic acid, glyceride derivatives, or natural pharmaceutically acceptable oils such as olive oil or rapeseed oil.

Furthermore, in some embodiments, alcohol or carboxymethyl cellulose dispersants, surfactants, emulsifiers, or the like may also be further added.

In addition, in some embodiments, the liquid formulation containing the pharmaceutical composition of this invention may also be filled into soft capsules for use.

In addition, in one embodiment, the mendicant or pharmaceutical composition of this invention may also be prepared with pharmaceutically acceptable polymeric auxiliaries into many dosage forms suitable for mucosal application, for example, buccal and/or sublingual dosage form. Generally, the polymeric auxiliaries include hydrophilic polymers, for example, including, but not limited to, acrylic acid polymers, hydrolyzed polyvinylalcohol, polyethylene oxides, polyacrylates, vinyl polymers, polyvinylpyrrolidones, dextran, guar gum, pectins, starches, or cellulosic polymers.

In some embodiments, the pharmaceutical composition disclosed in this invention may be used as an additional adjunctive therapeutic agent, so as to improve the therapeutic effect of a primary treatment method of cancers such as surgery, radiotherapy, or chemotherapy. The pharmaceutical composition disclosed in this invention may be applied alone or in combination with conventional pharmaceutically acceptable auxiliaries, and, for example, may be administered orally or with a food to an individual.

In some embodiments, the method of this invention further includes before, during or after administering the pharmaceutical composition of this invention to the individual, additionally applying another primary treatment means of cancers such as surgery, radiotherapy, or chemotherapy to the individual, so as to improve the therapeutic effect of cancers in the individual.

For a more thorough and complete description of this disclosure, illustrative description for implementation aspects and specific examples of this invention is provided below; however, this is not intended to represent the only form of specific examples in which the present invention may be practiced or utilized. Features of a number of specific examples and process steps and sequences to construct and operate these specific examples are covered in the embodiments. However, the same or equivalent functions and step sequences may also be accomplished by other examples.

Firstly, standard operation processes of the tests in examples of this invention are described.

<Cell Viability Tests>

Cells used the tests were human leukemia cells U937, human lung cancer cells A549, African green monkey kidney cells Vero, human Glioblastoma cells U87-MG, human liver cancer cells Mahlavu, human colorectal cancer cells SW-480, human breast cancer cells MDA-MB-231, and human breast cancer cells MDA-MB-468.

U937 and A549 cells were cultured in RPMI 1640 medium, supplemented with 10% fetal calf serum (FCS), 100 U/ml penicillin, and 10 µg/ml streptomycin.

Vero, U87-MG, MDA-MB-231, MDA-MB-468, Mahlavu, and SW480 were cultured in DMEM medium containing 10% fetal calf serum (FCS), 100 U/ml penicillin, and 10 μg/ml streptomycin.

Vero, U87-MG, MDA-MB-231, MDA-MB-468, A549, and Mahlavu cells were seeded at 1×104 cells/well in 96-well plates in cell culture medium containing 10% fetal calf serum (FCS), incubated for 16 hours in an incubator for complete cell adhesion, washed twice with phosphate-buffered saline (PBS), added with cell culture medium containing 10% fetal calf serum (FCS), incubated for 24 hours in the incubator, washed once with phosphate-buffered saline (PBS), added with cell culture medium containing the agent and 0.1% fetal calf serum (FCS) (at final concentrations of the agent of 200, 100, 50, 25, 12.5, 6.25, 3.125, 1.5625, 0.78125, 0 μM), and incubated for 48 hours in the incubator. Cell viability was determined with Resazurin (at a final concentration of 25 μg/mL).

SW480 cells were seeded at 1×104 cells/well in 96-well plates in cell culture medium containing 10% fetal calf serum (FCS), incubated for 36 hours in an incubator for complete cell adhesion, washed twice with phosphate-buffered saline (PBS), added with cell culture medium containing the agent and 0.1% fetal calf serum (FCS) (at final concentrations of the agent of 200, 100, 50, 25, 12.5, 6.25, 3.125, 1.5625, 0.78125, 0 μM), and incubated for 48 hours in the incubator. Cell viability was determined with Resazurin (at a final concentration of 25 μg/mL).

U937 cells were incubated for 24 hours in the incubator in cell culture medium containing 0.1% fetal calf serum (FCS), washed twice with phosphate-buffered saline (PBS), again added with cell culture medium containing 0.1% fetal calf serum (FCS), seeded at 1×104 cells/well in 96-well plates, added with cell culture medium containing the agent and 0.1% fetal calf serum (FCS) (at final concentrations of the agent of 200, 100, 50, 25, 12.5, 6.25, 3.125, 1.5625, 0.78125, 0 μM), and incubated for 48 hours in the incubator. Cell viability was determined with Resazurin (at a final concentration of 25 μg/mL).

Hereafter, the present invention will be described in detail by explaining preferred embodiments of the invention with reference to the attached drawings.

Preparative Example 1

Figure 2:
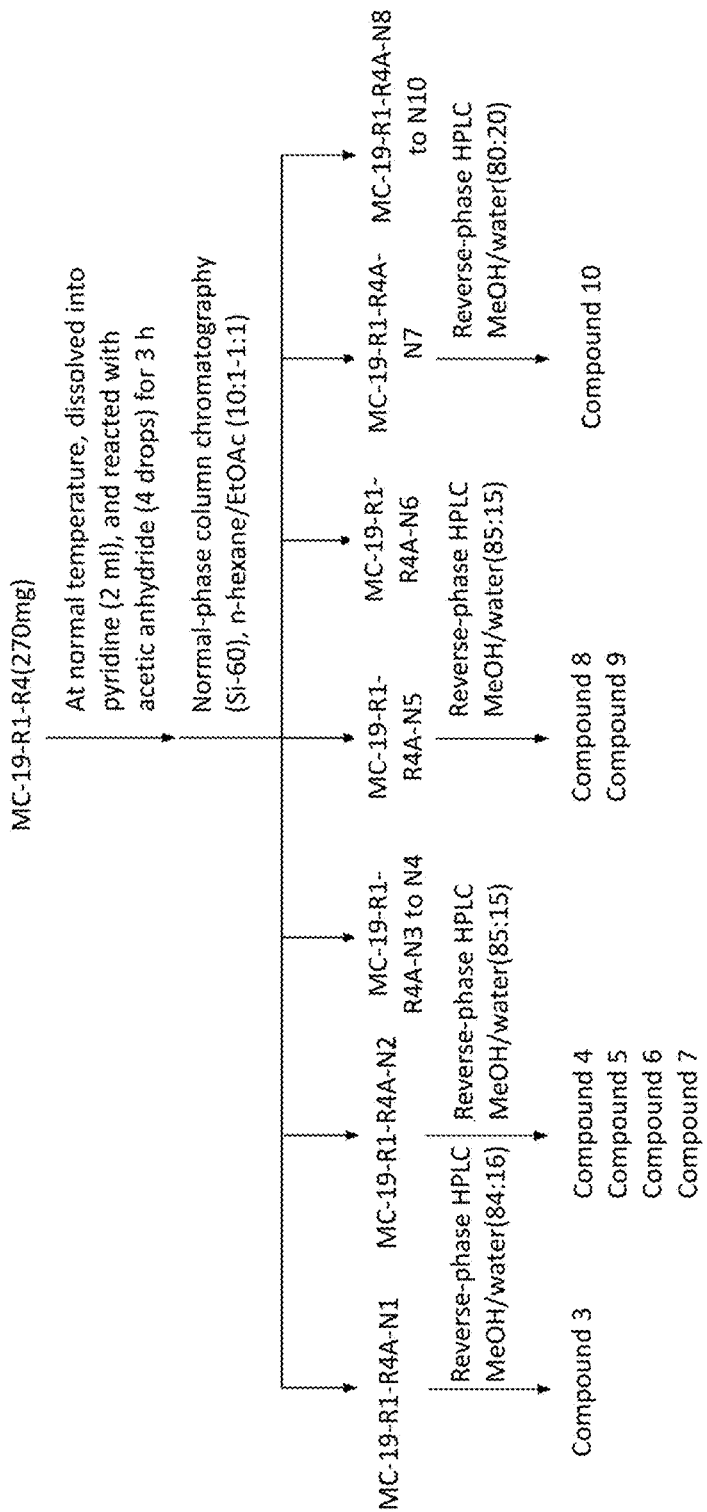
FIG. 2 is a flow diagram illustrating separation of compounds 3 to 10 in preparative example 1 according to the present invention.
Figure 3:
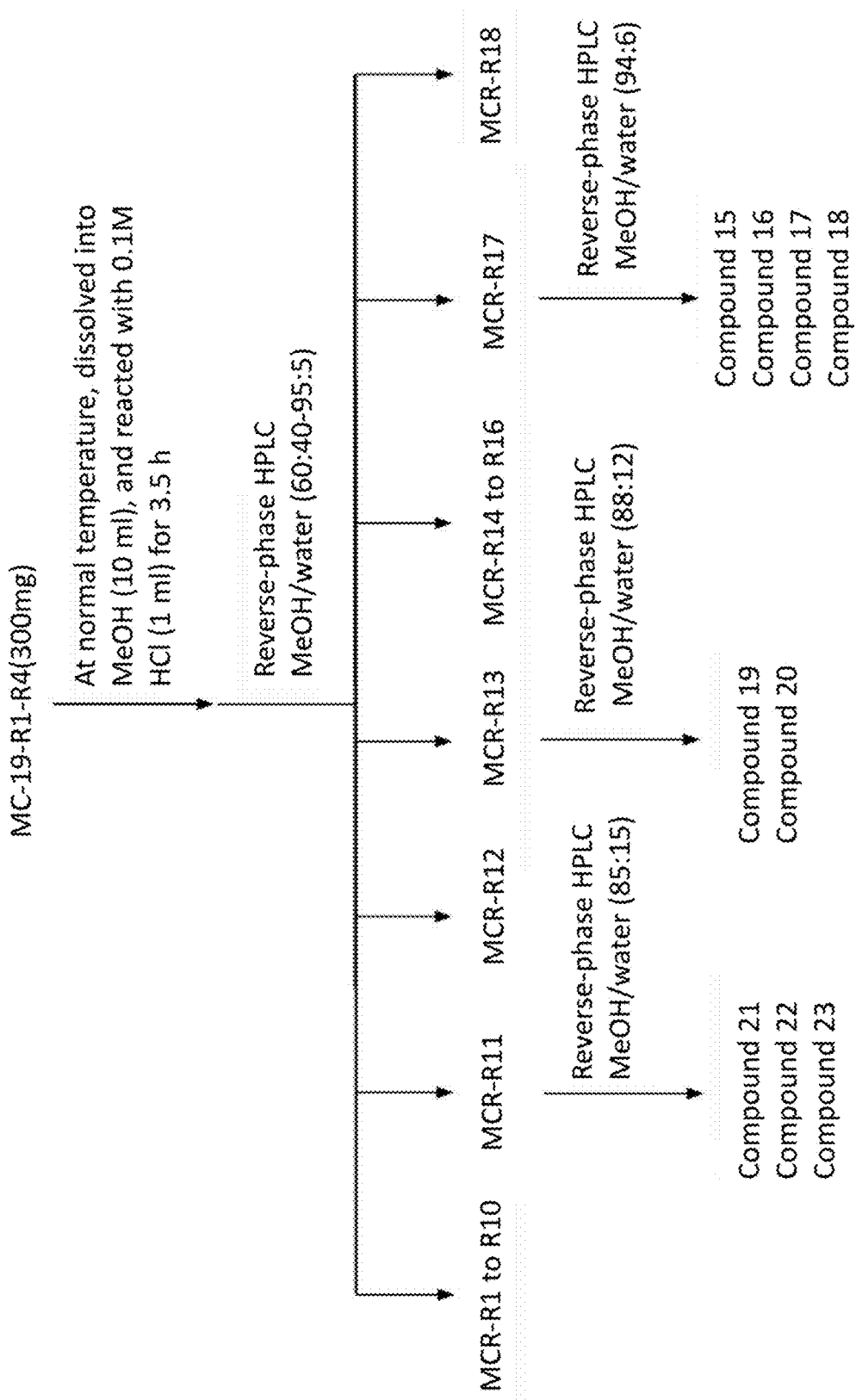
FIG. 3 is a flow diagram illustrating separation of compounds 15 to 23 in preparative example 1 according to the present invention.
Figure 4:
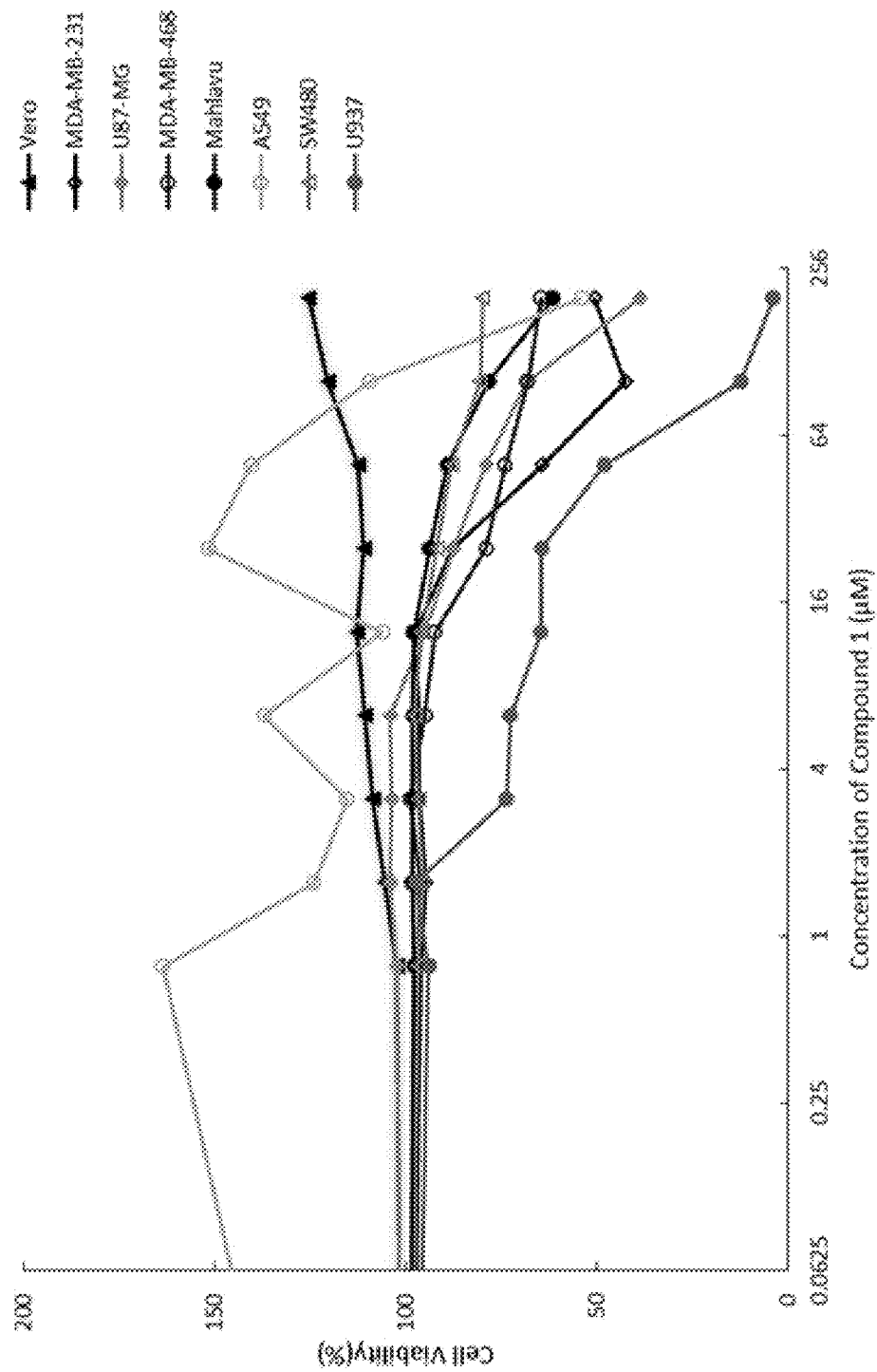
FIG. 4 is a diagram illustrating results of cell viability tests for compound 1 in example 1 according to the present invention.
Figure 5:
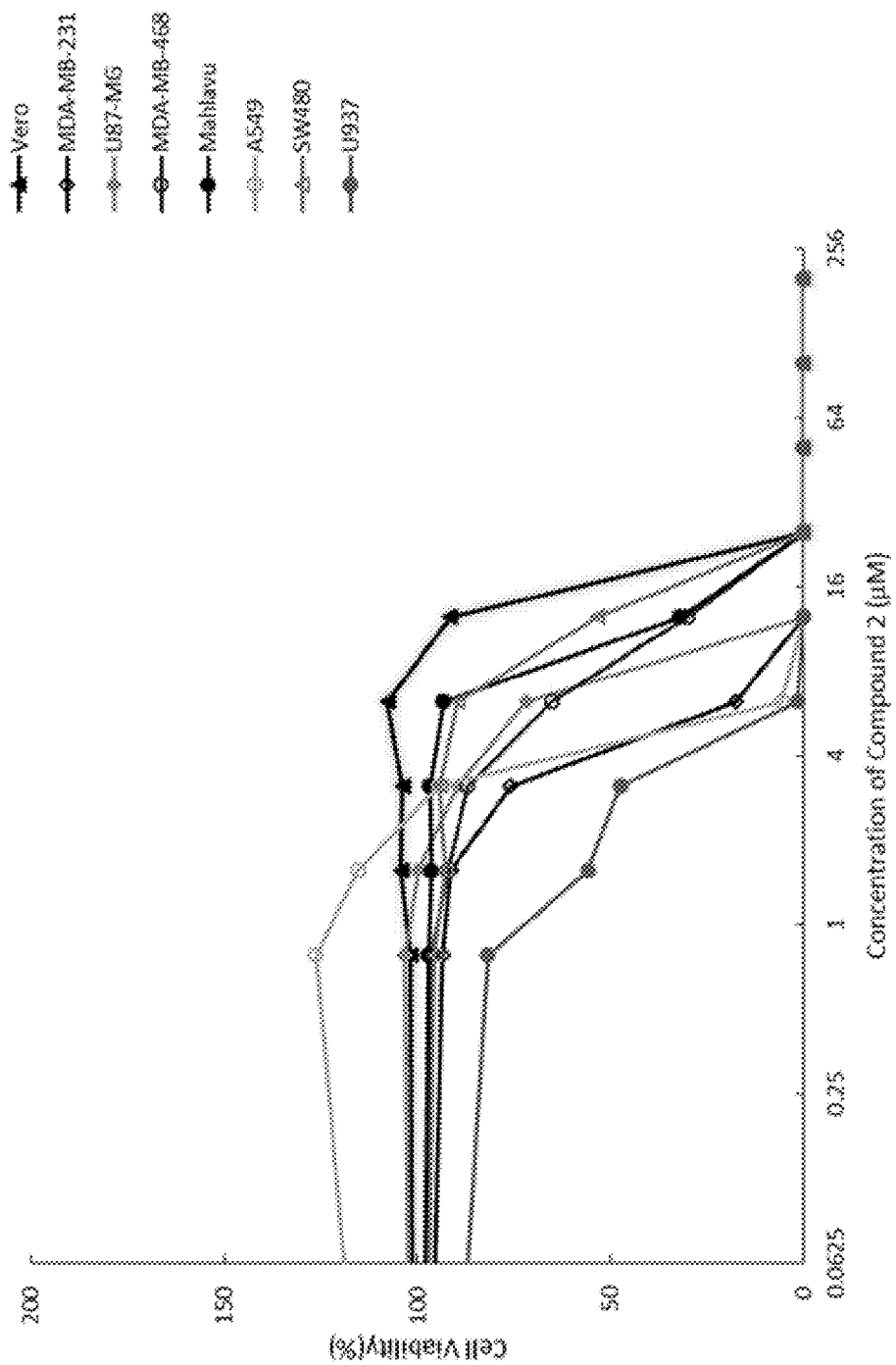
FIG. 5 is a diagram illustrating results of cell viability tests for compound 2 in example 2 according to the present invention.
Figure 6:
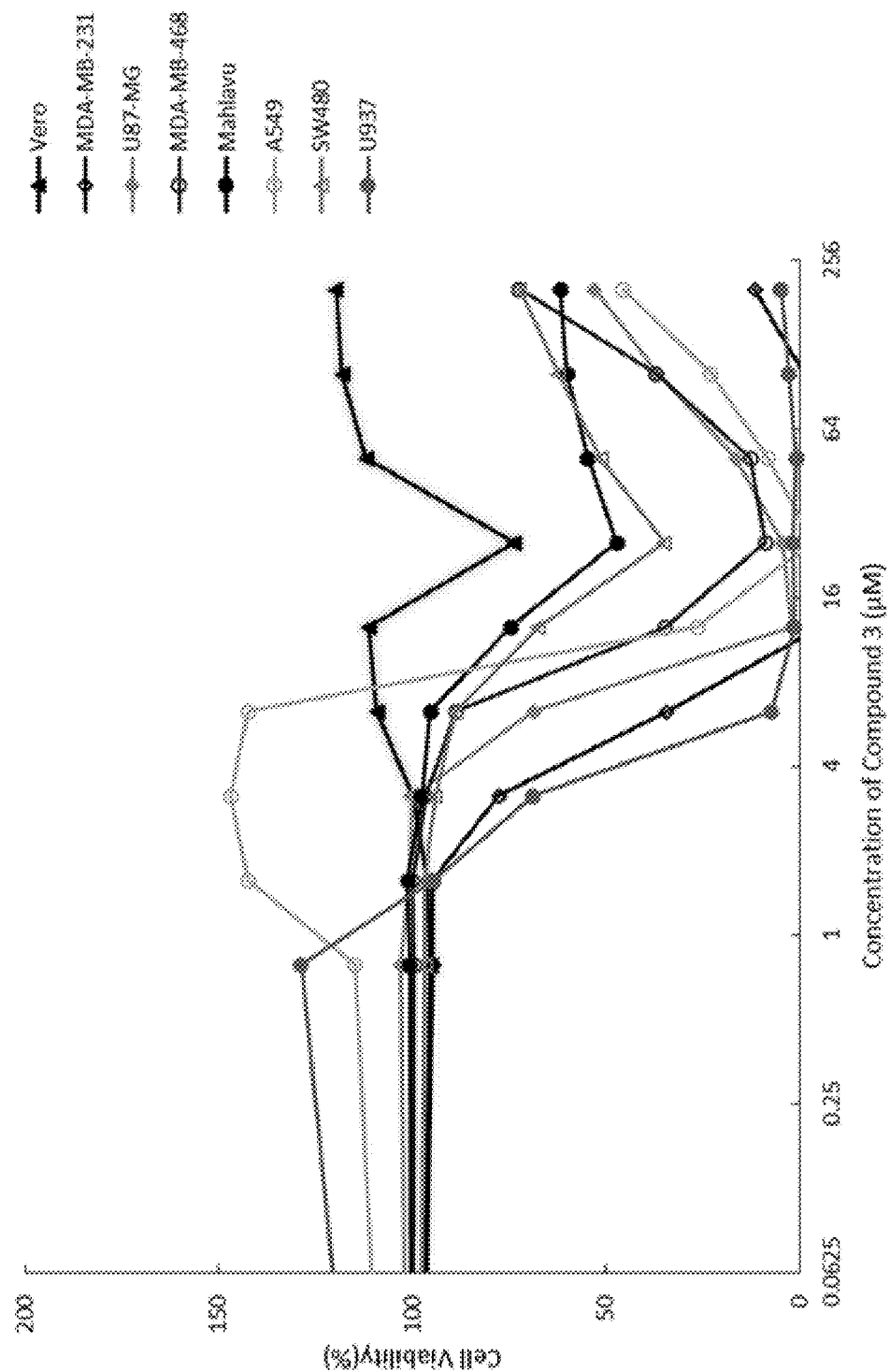
FIG. 6 is a diagram illustrating results of cell viability tests for compound 3 in example 3 according to the present invention.
Figure 7:
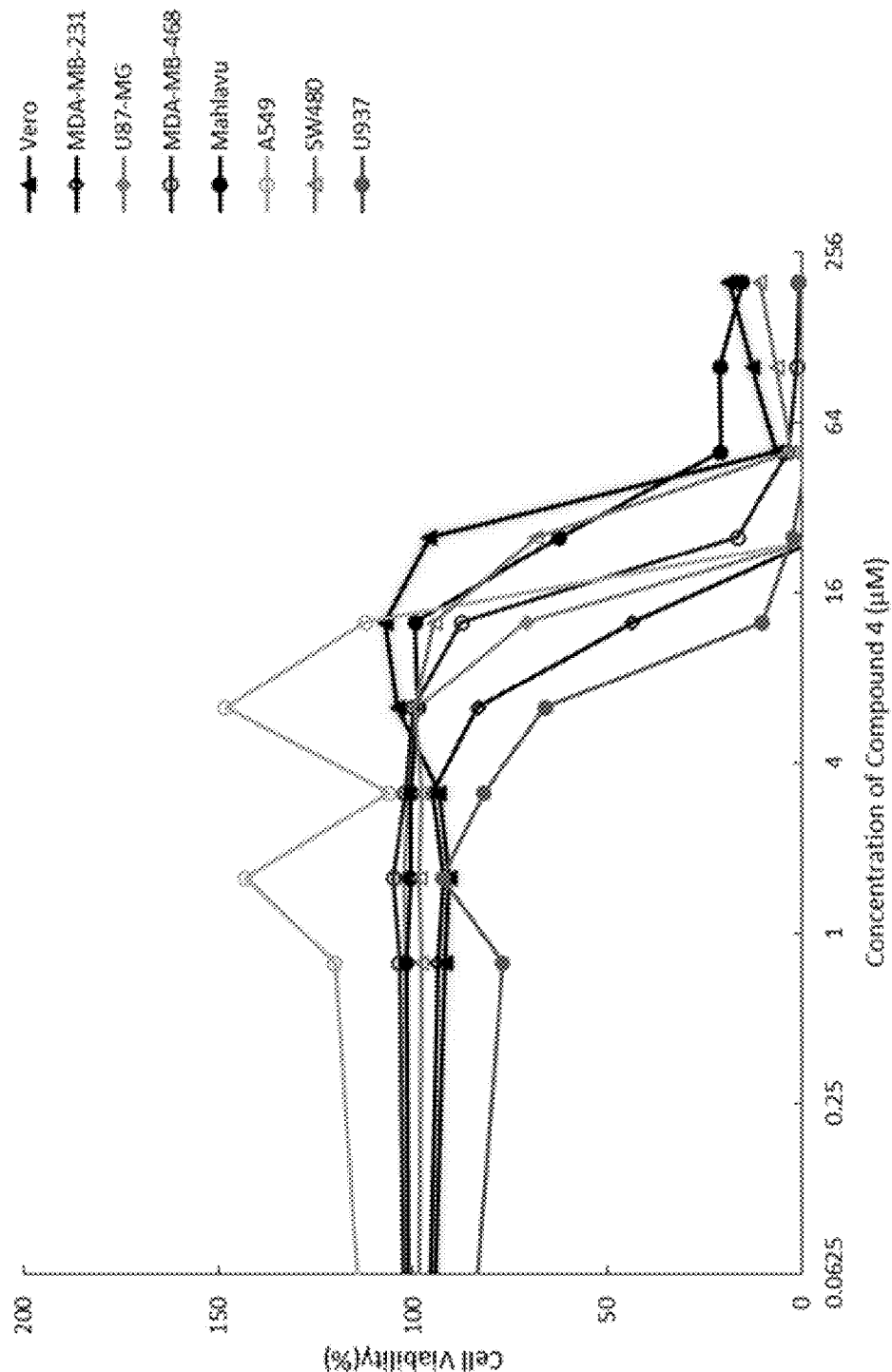
FIG. 7 is a diagram illustrating results of cell viability tests for compound 4 in example 4 according to the present invention.
Figure 8:
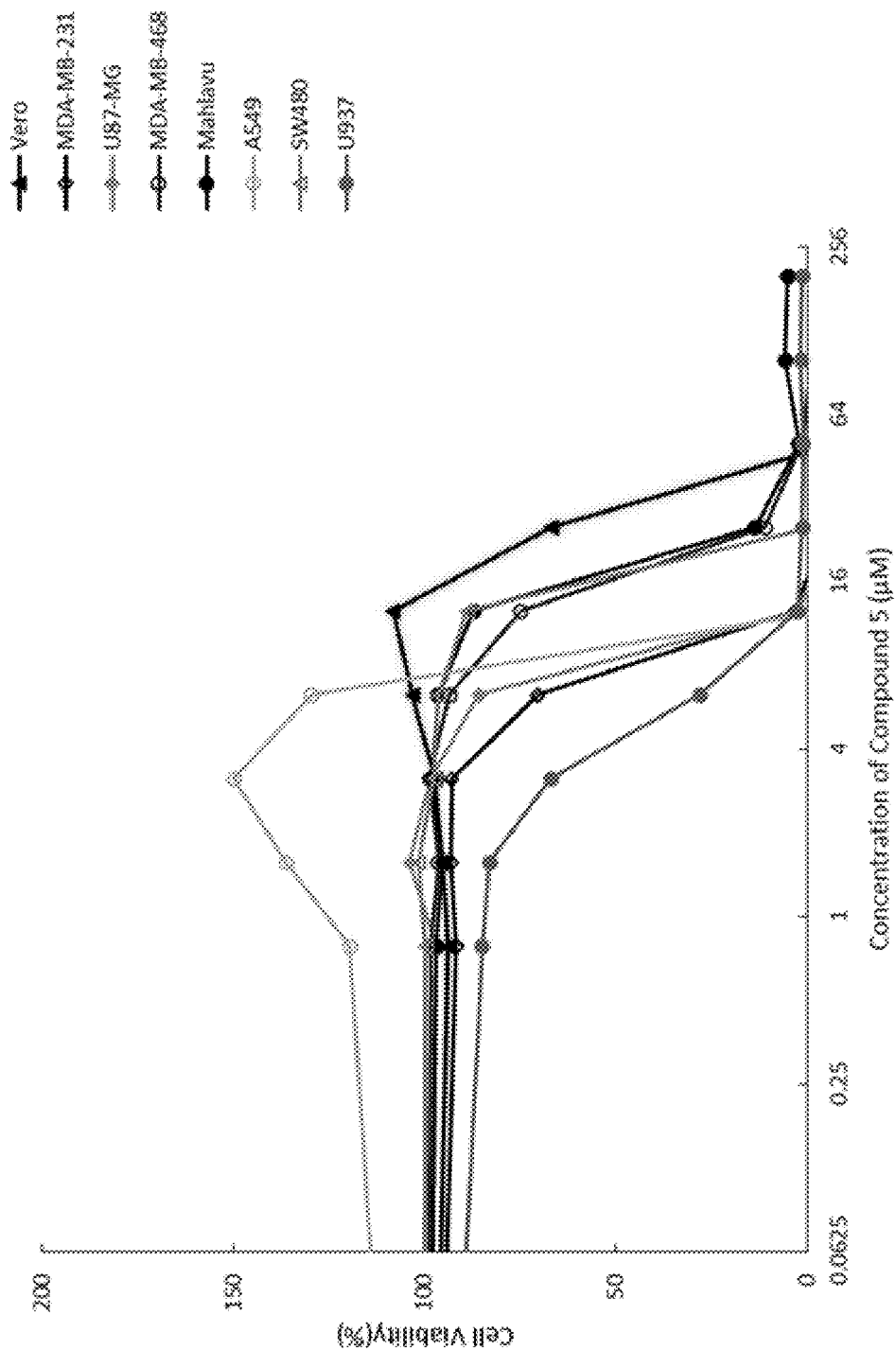
FIG. 8 is a diagram illustrating results of cell viability tests for compound 5 in example 5 according to the present invention.
Figure 9:
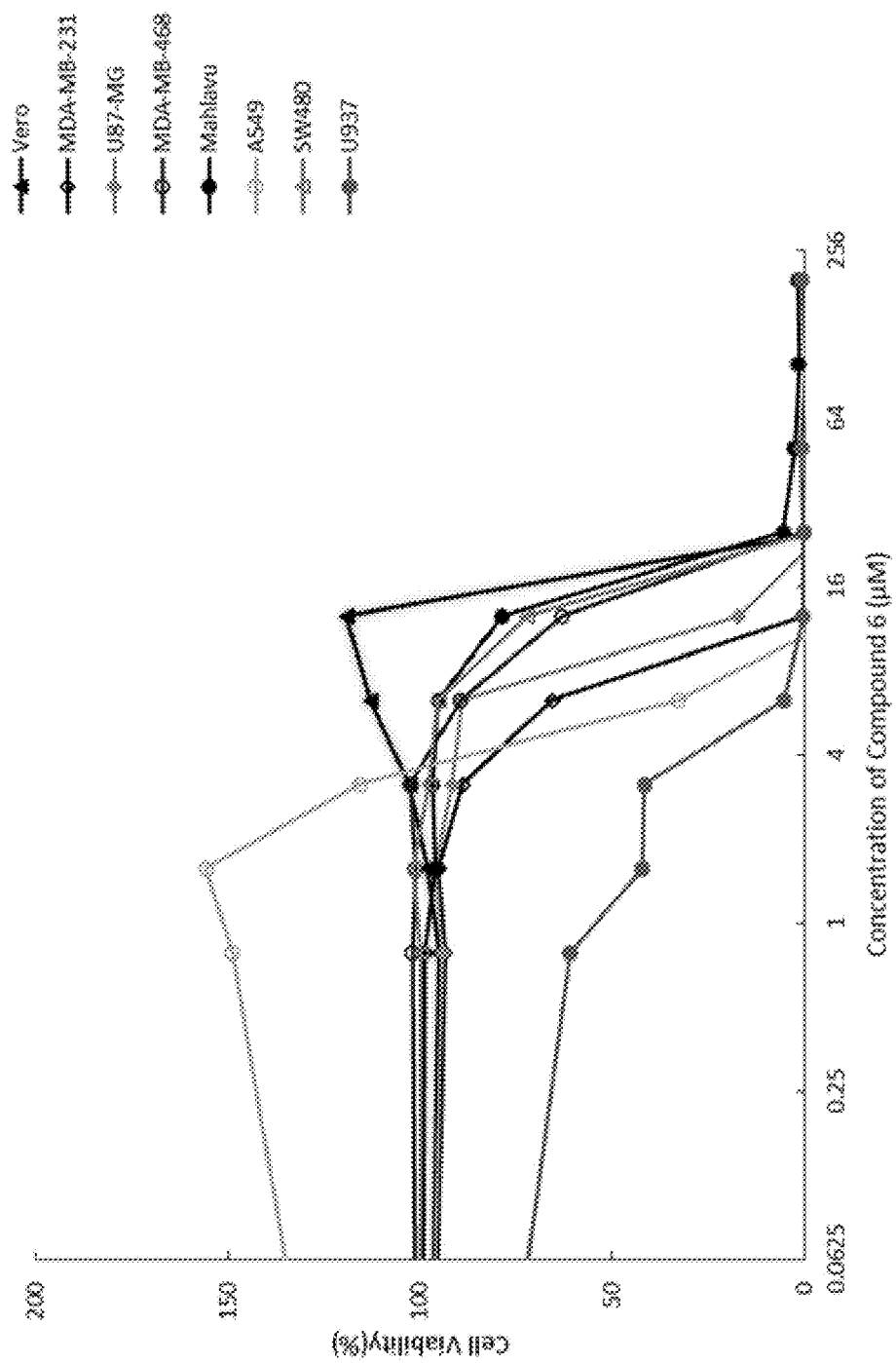
FIG. 9 is a diagram illustrating results of cell viability tests for compound 6 in example 6 according to the present invention.
Figure 10:
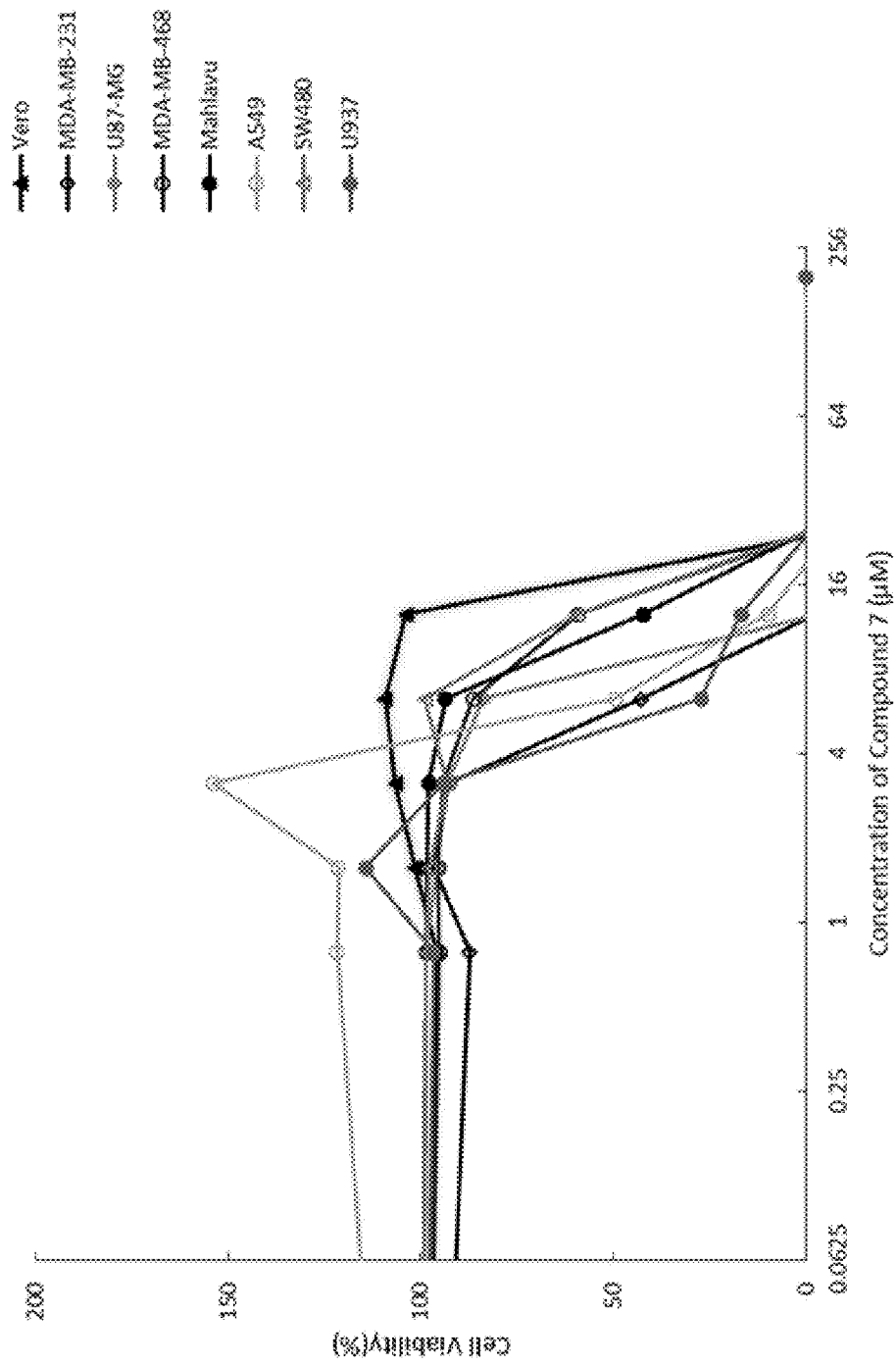
FIG. 10 is a diagram illustrating results of cell viability tests for compound 7 in example 7 according to the present invention.
Figure 11:
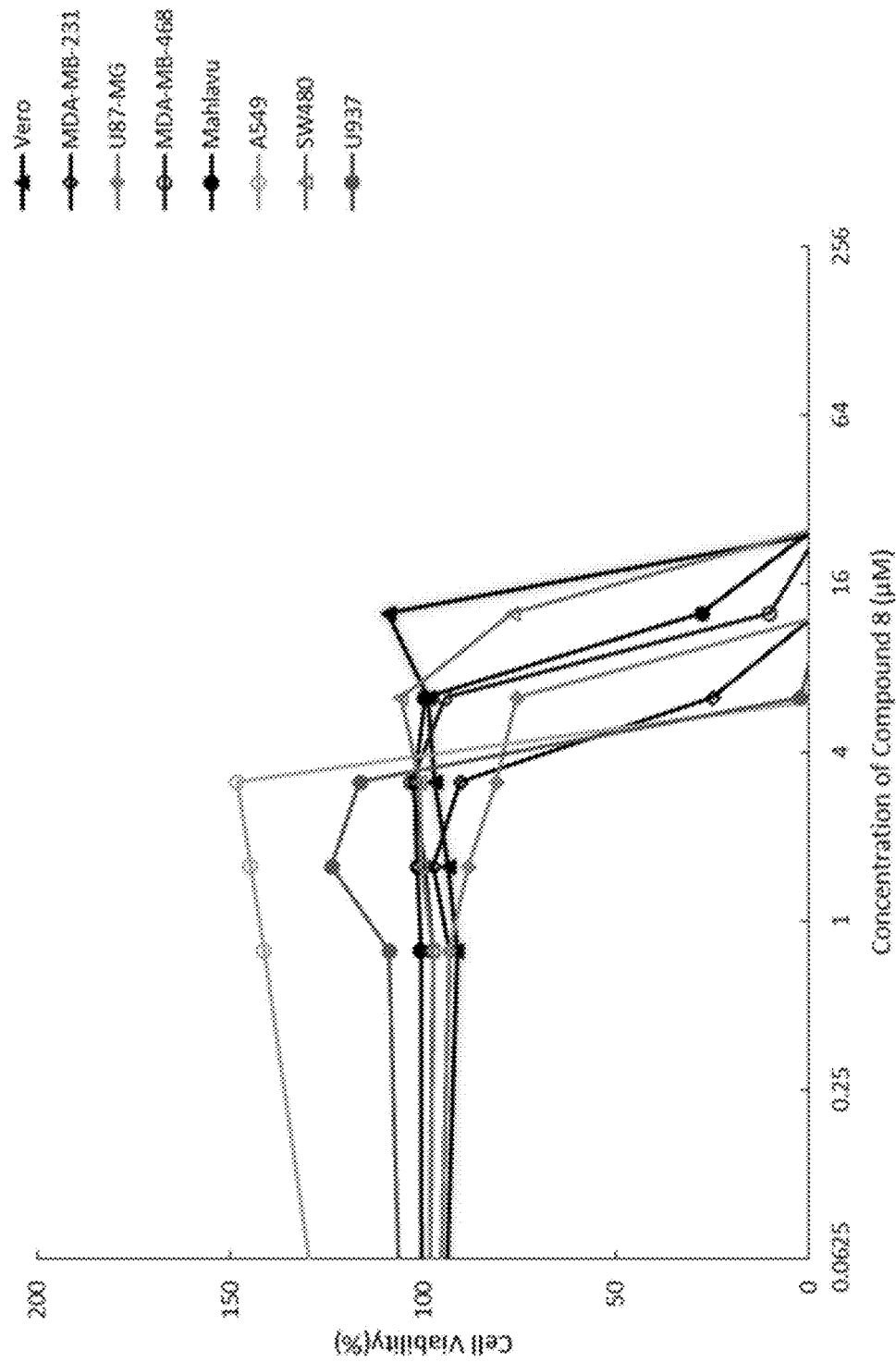
FIG. 11 is a diagram illustrating results of cell viability tests for compound 8 in example 8 according to the present invention.
Figure 12:
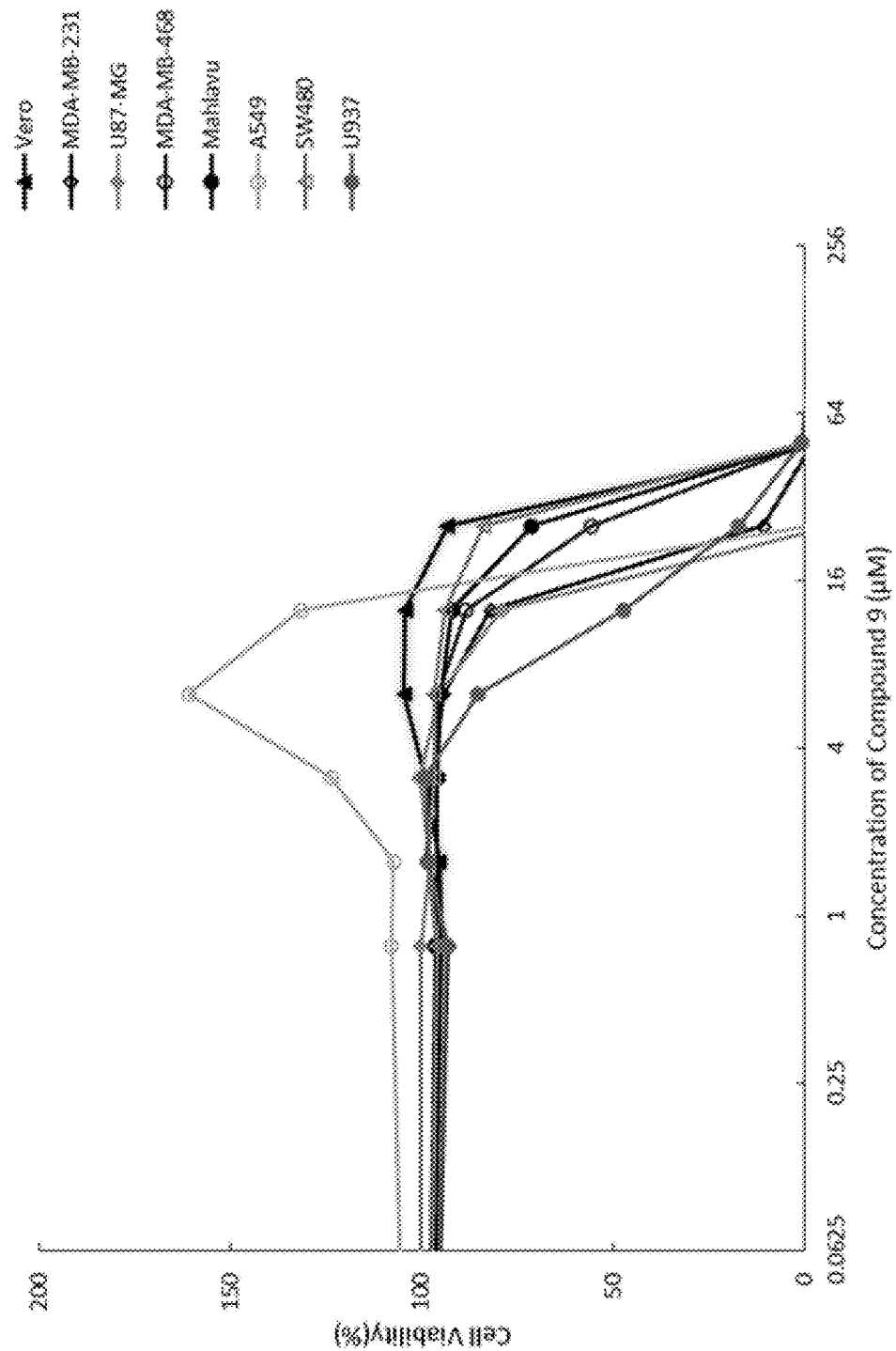
FIG. 12 is a diagram illustrating results of cell viability tests for compound 9 in example 9 according to the present invention.
Figure 13:
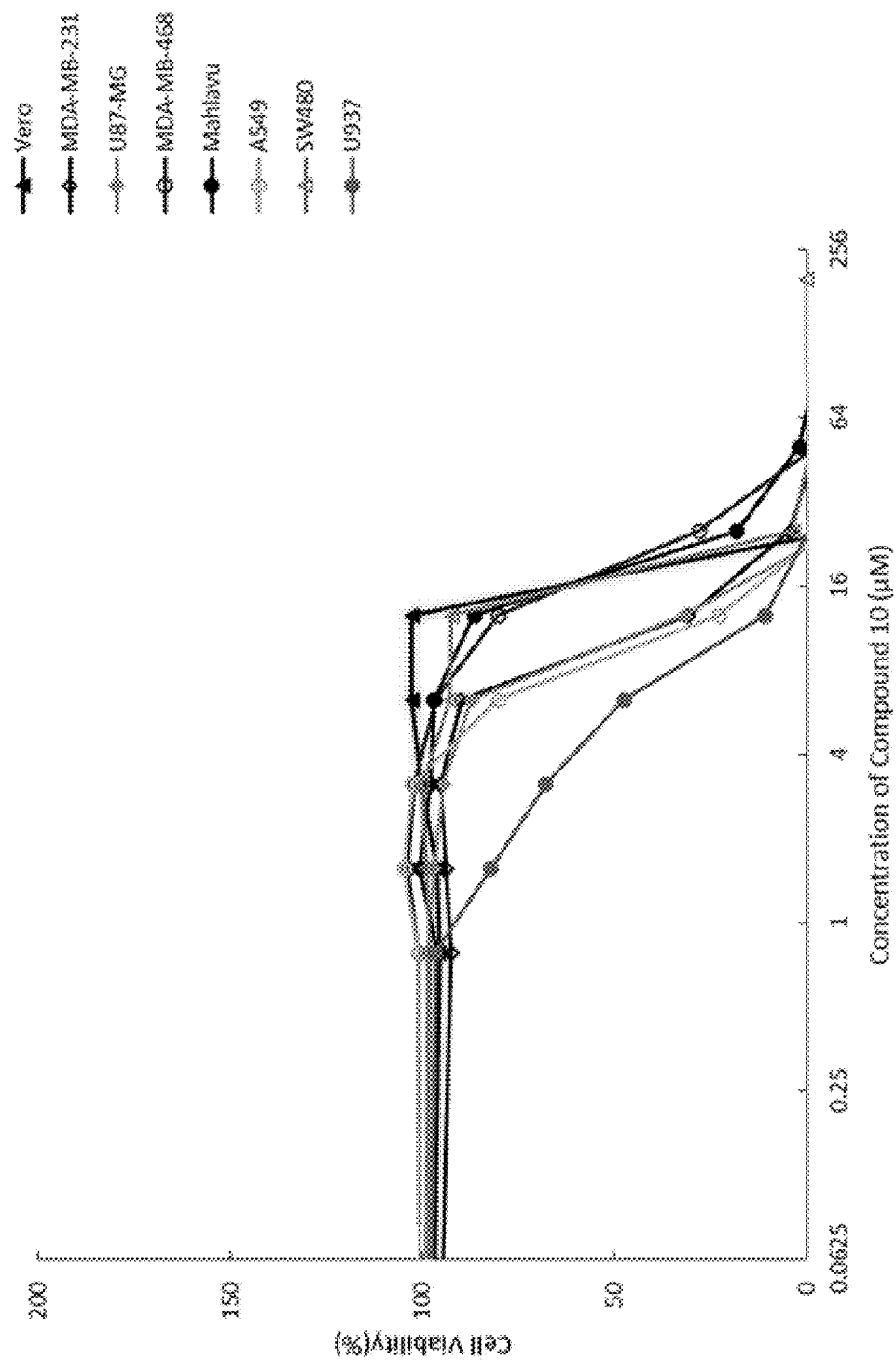
FIG. 13 is a diagram illustrating results of cell viability tests for compound 10 in example 10 according to the present invention.
Figure 14:
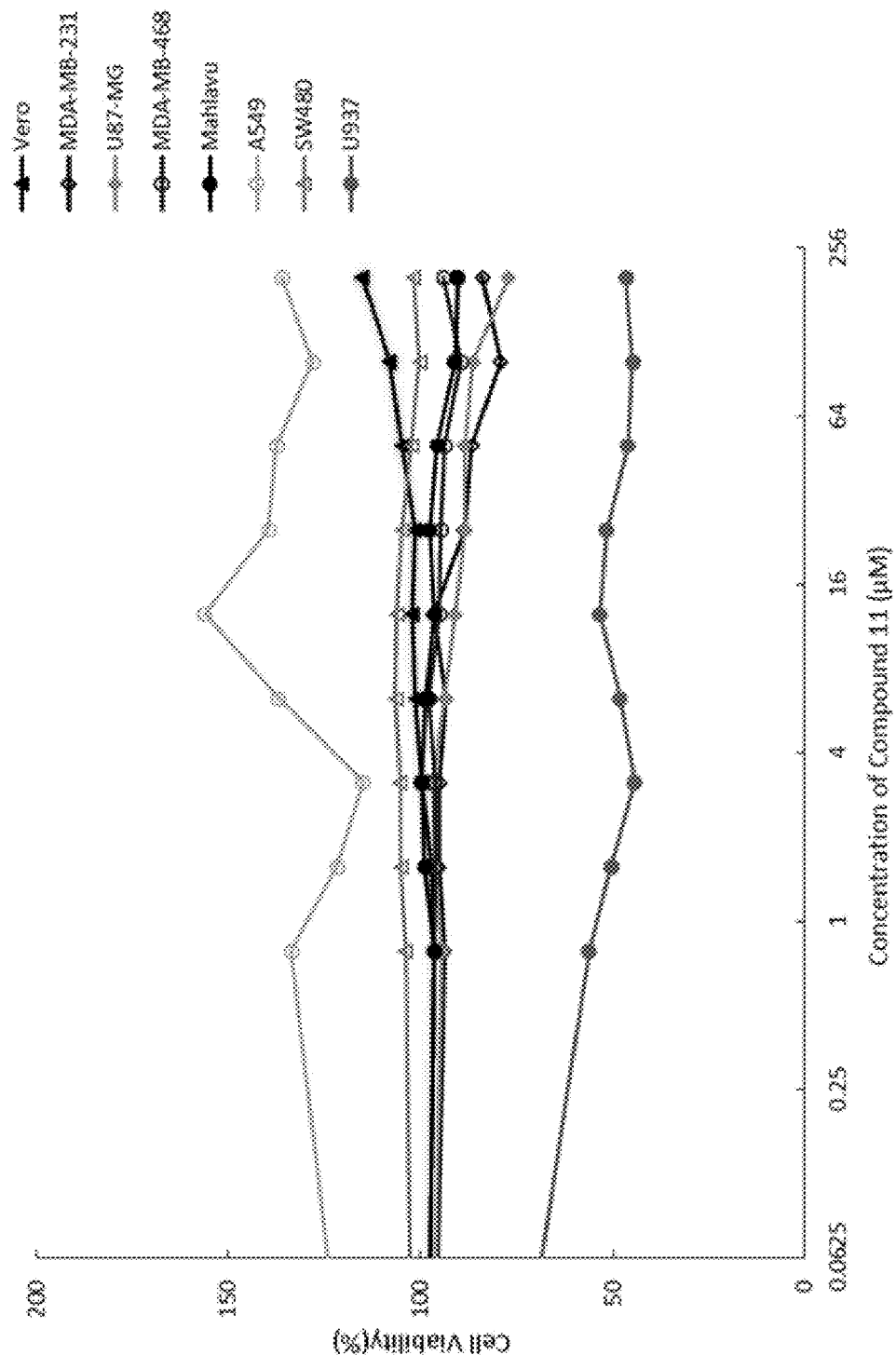
FIG. 14 is a diagram illustrating results of cell viability tests for compound 11 in example 11 according to the present invention.
Figure 15:
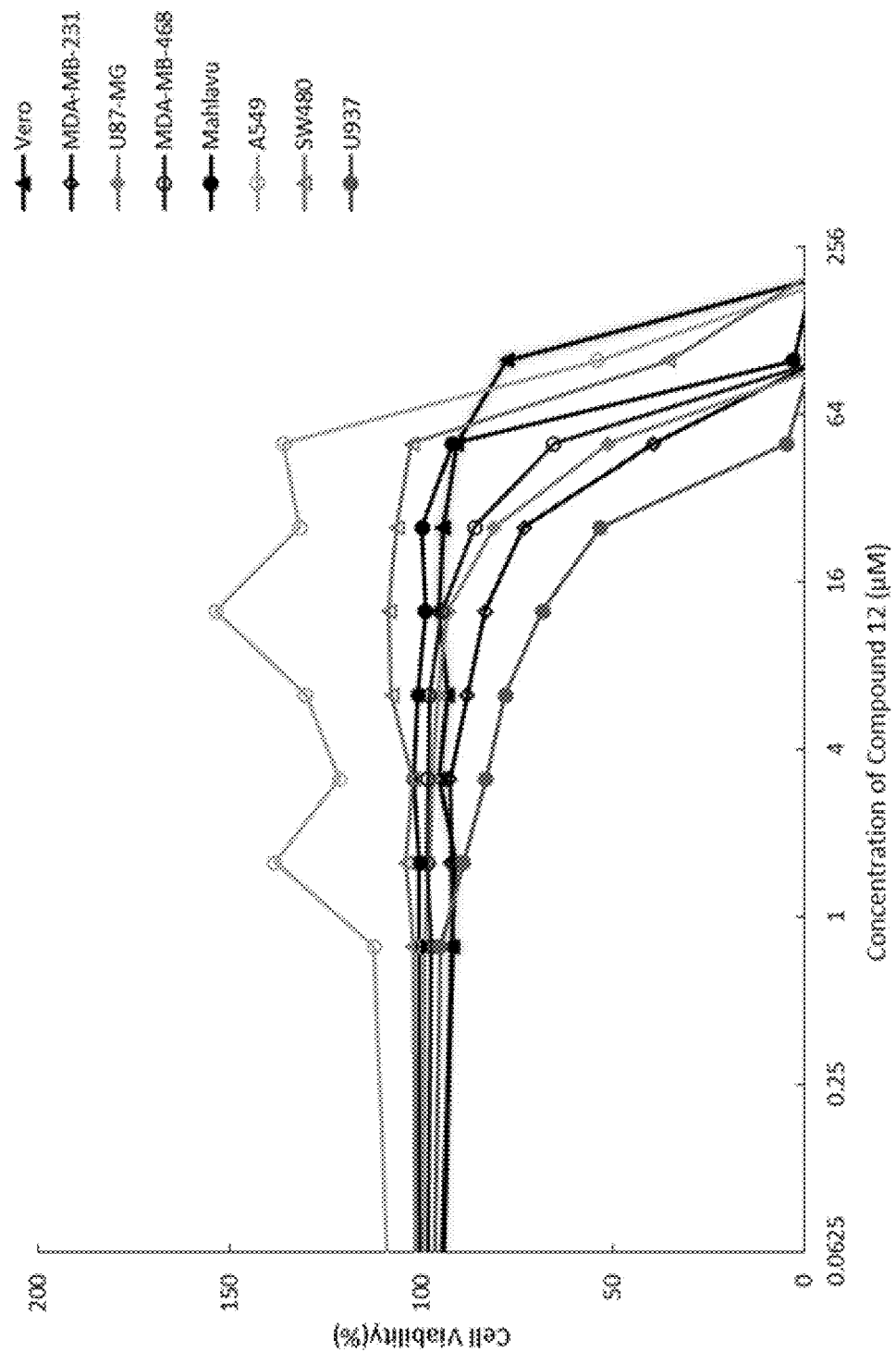
FIG. 15 is a diagram illustrating results of cell viability tests for compound 12 in example 12 according to the present invention.
Figure 16:
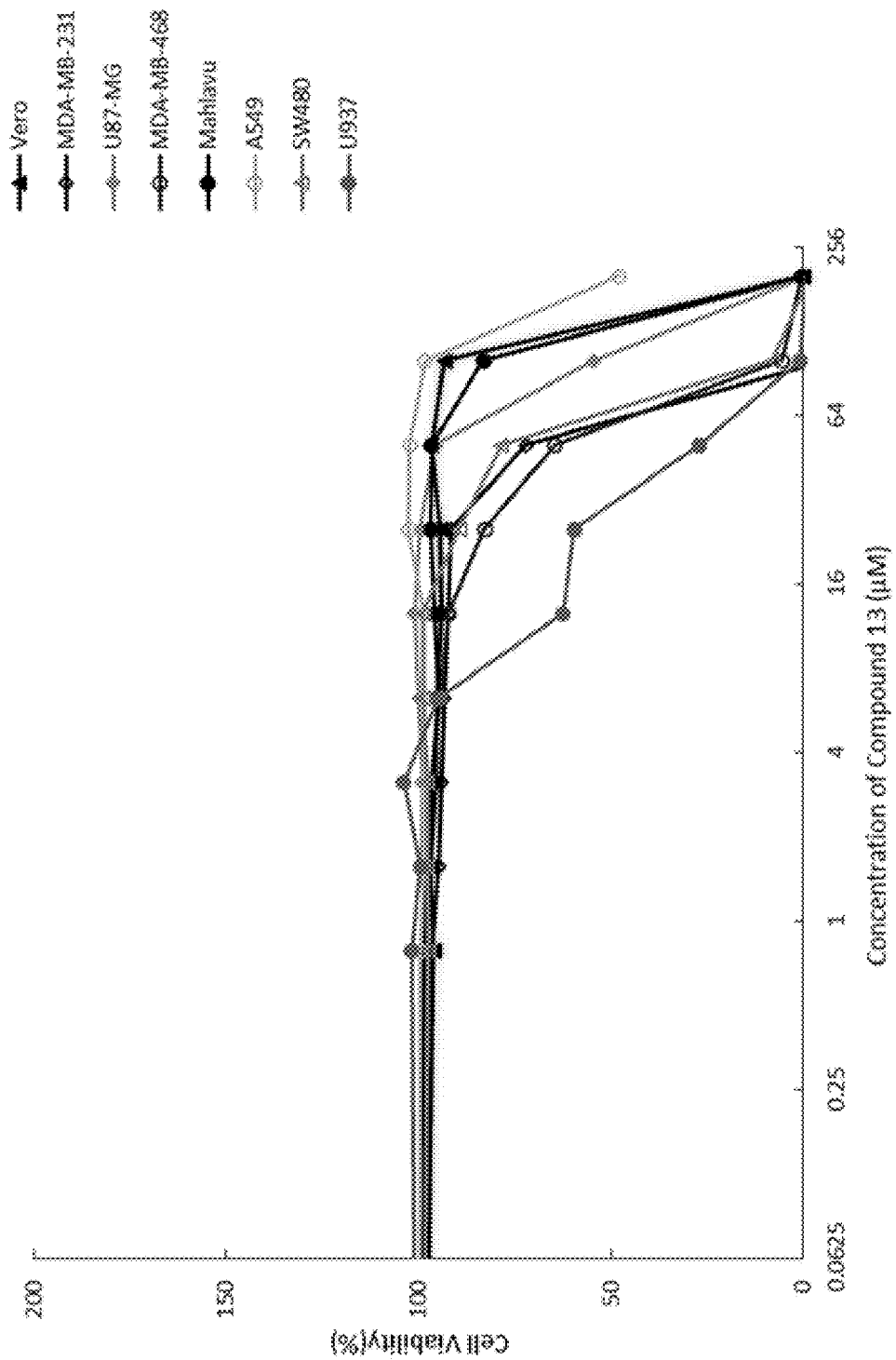
FIG. 16 is a diagram illustrating results of cell viability tests for compound 13 in example 13 according to the present invention.
Figure 17:
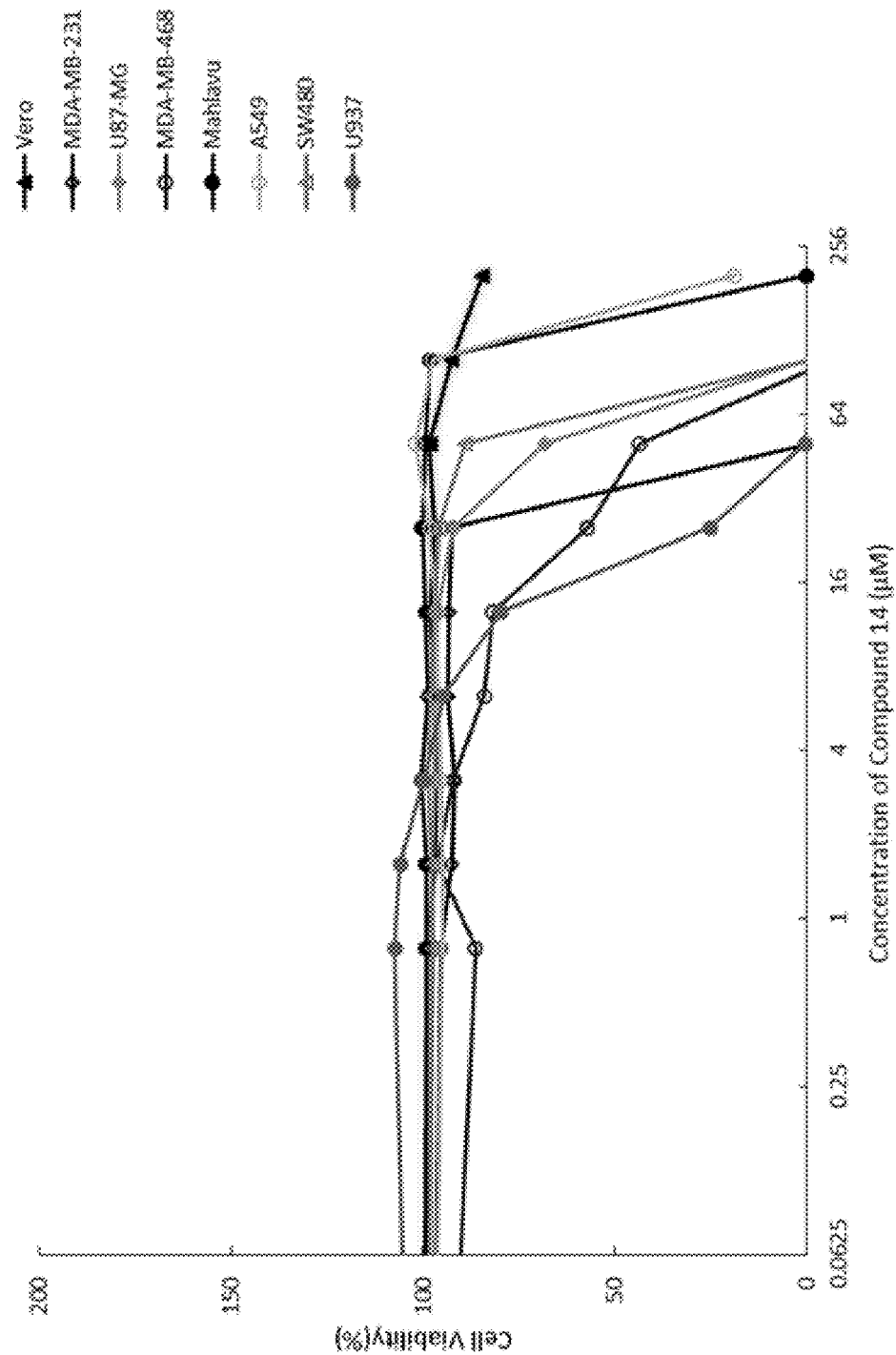
FIG. 17 is a diagram illustrating results of cell viability tests for compound 14 in example 14 according to the present invention.
Figure 18:
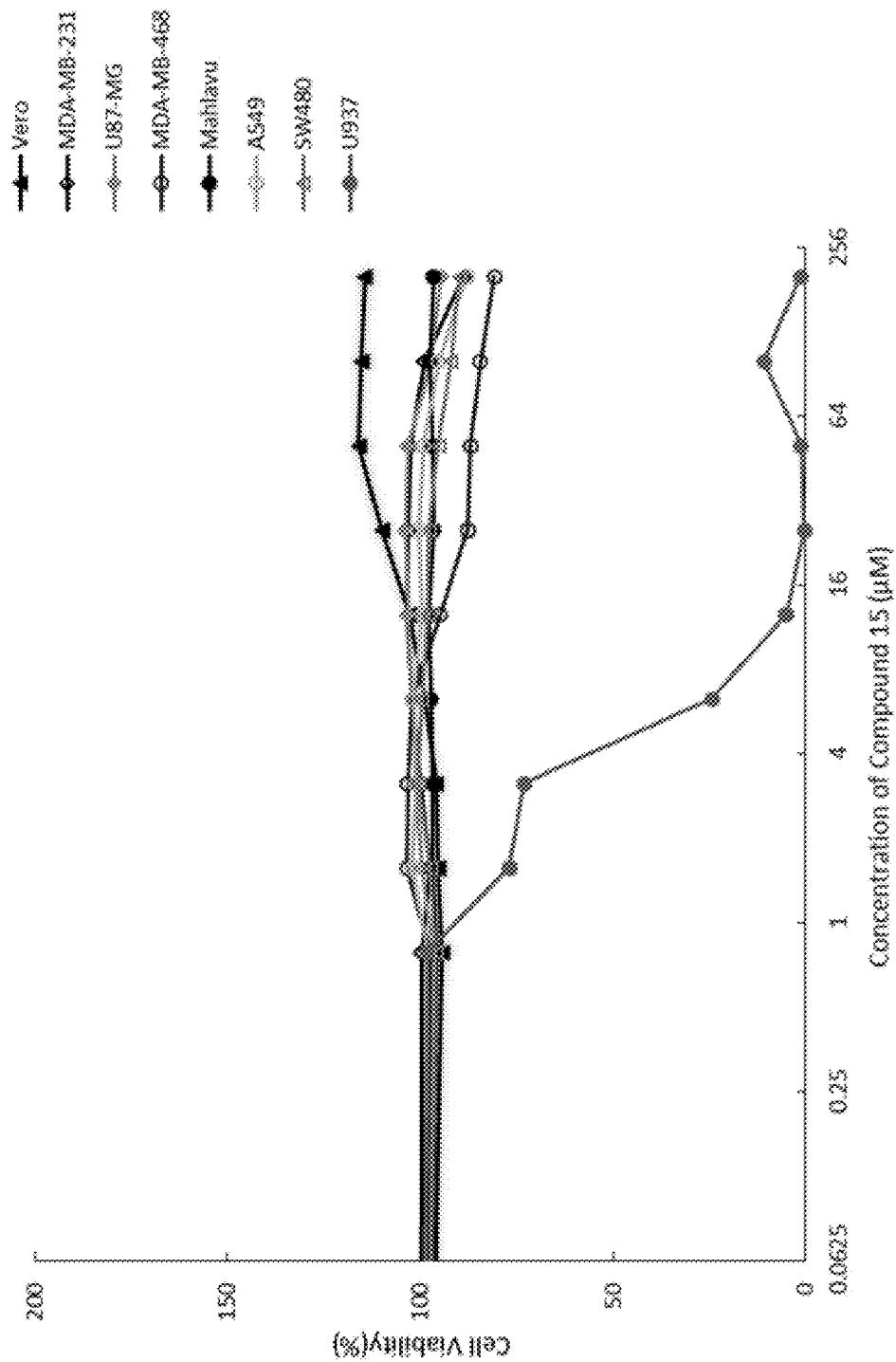
FIG. 18 is a diagram illustrating results of cell viability tests for compound 15 in example 15 according to the present invention.
Figure 19:
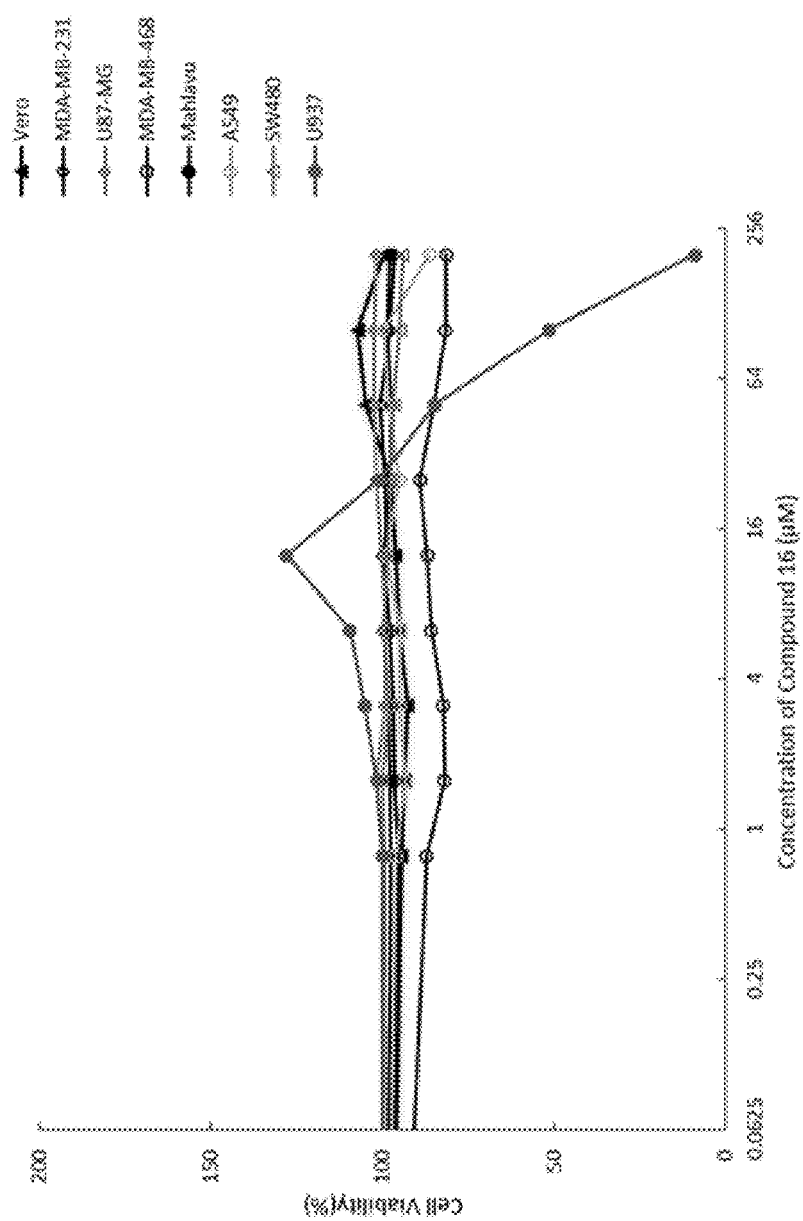
FIG. 19 is a diagram illustrating results of cell viability tests for compound 16 in example 16 according to the present invention.
Figure 20:
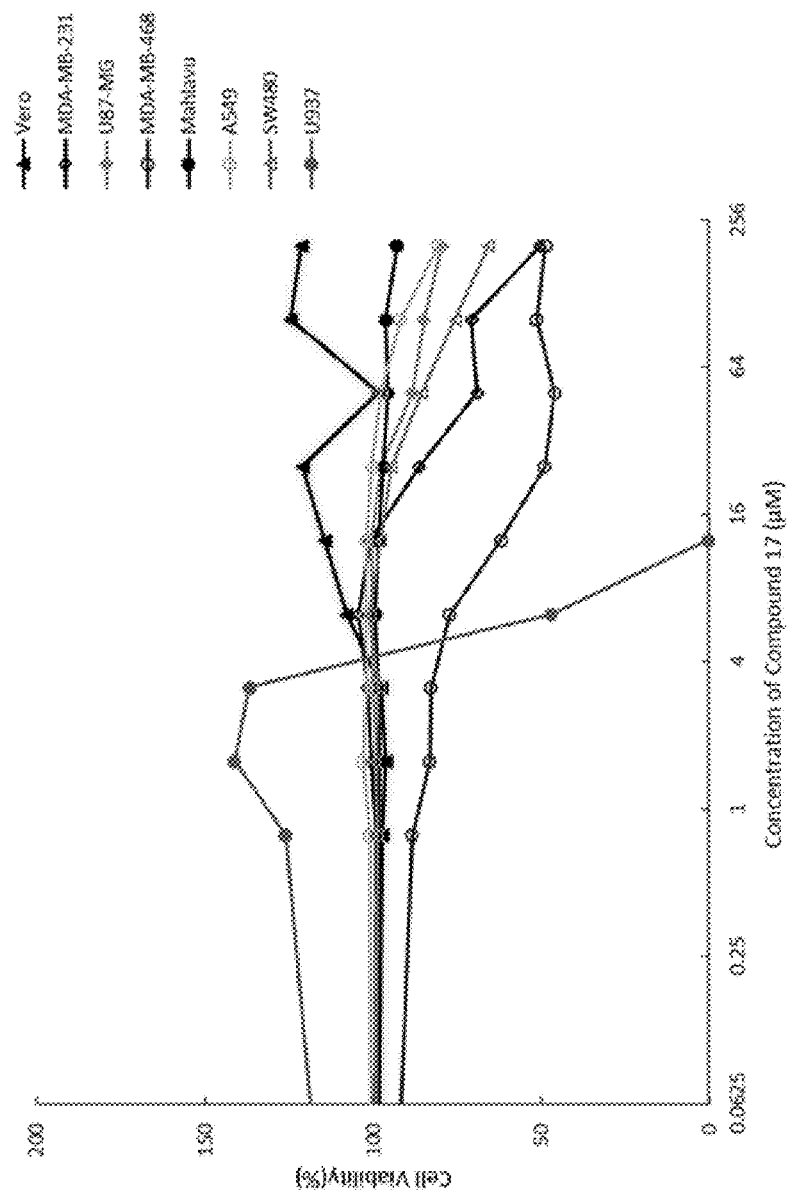
FIG. 20 is a diagram illustrating results of cell viability tests for compound 17 in example 17 according to the present invention.
Figure 21:
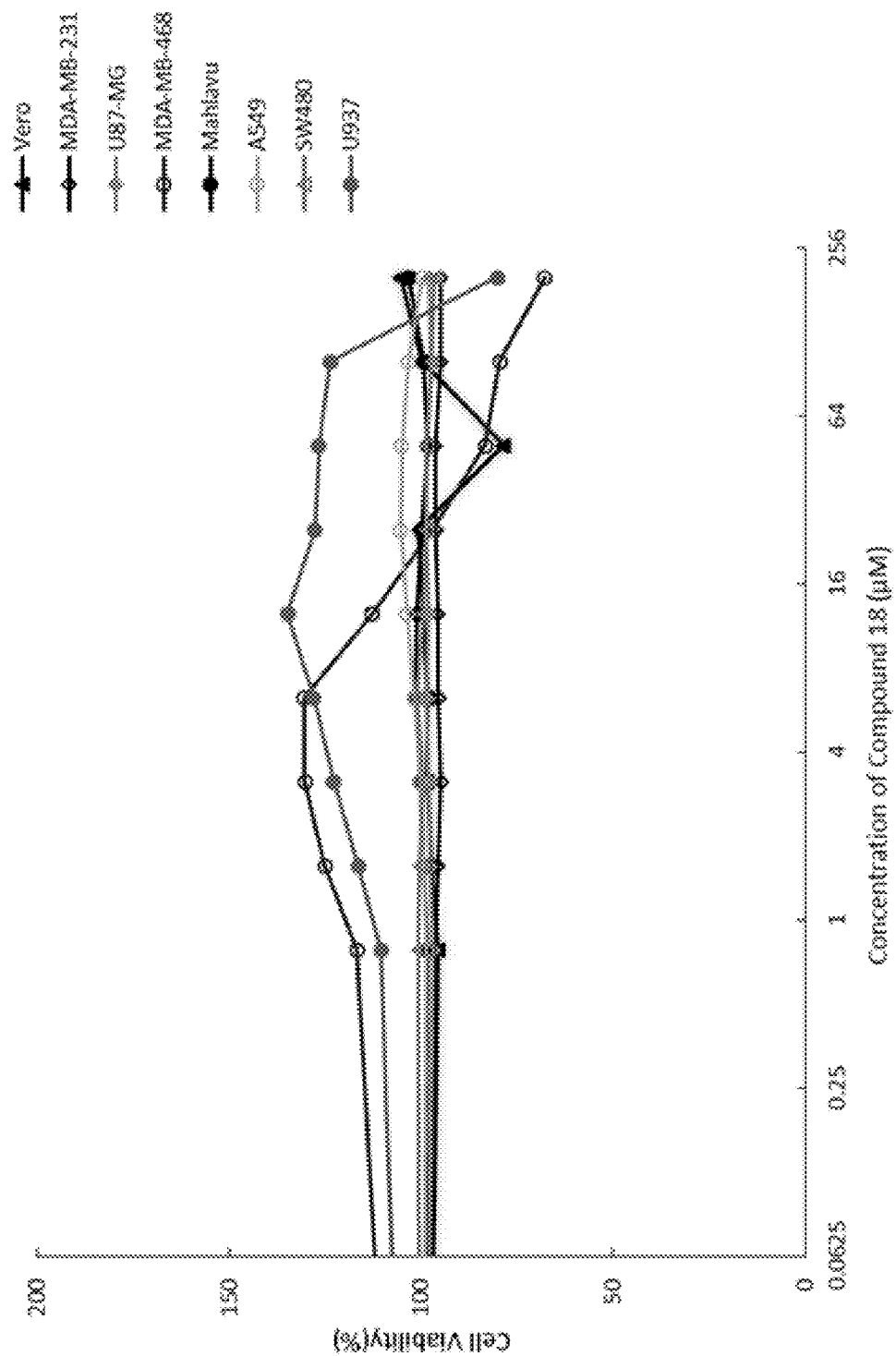
FIG. 21 is a diagram illustrating results of cell viability tests for compound 18 in example 18 according to the present invention.
Figure 22:
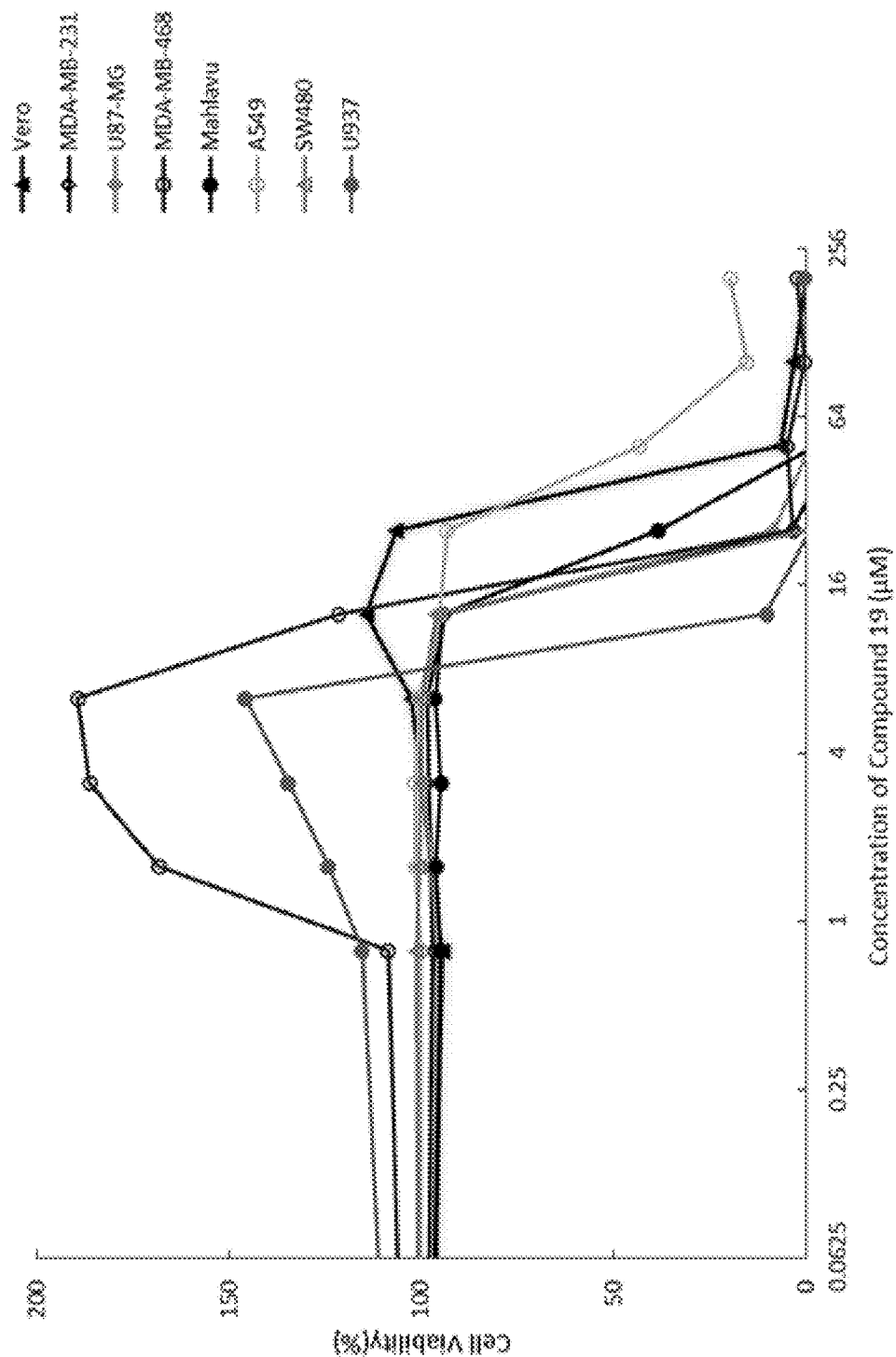
FIG. 22 is a diagram illustrating results of cell viability tests for compound 19 in example 19 according to the present invention.
Figure 23:
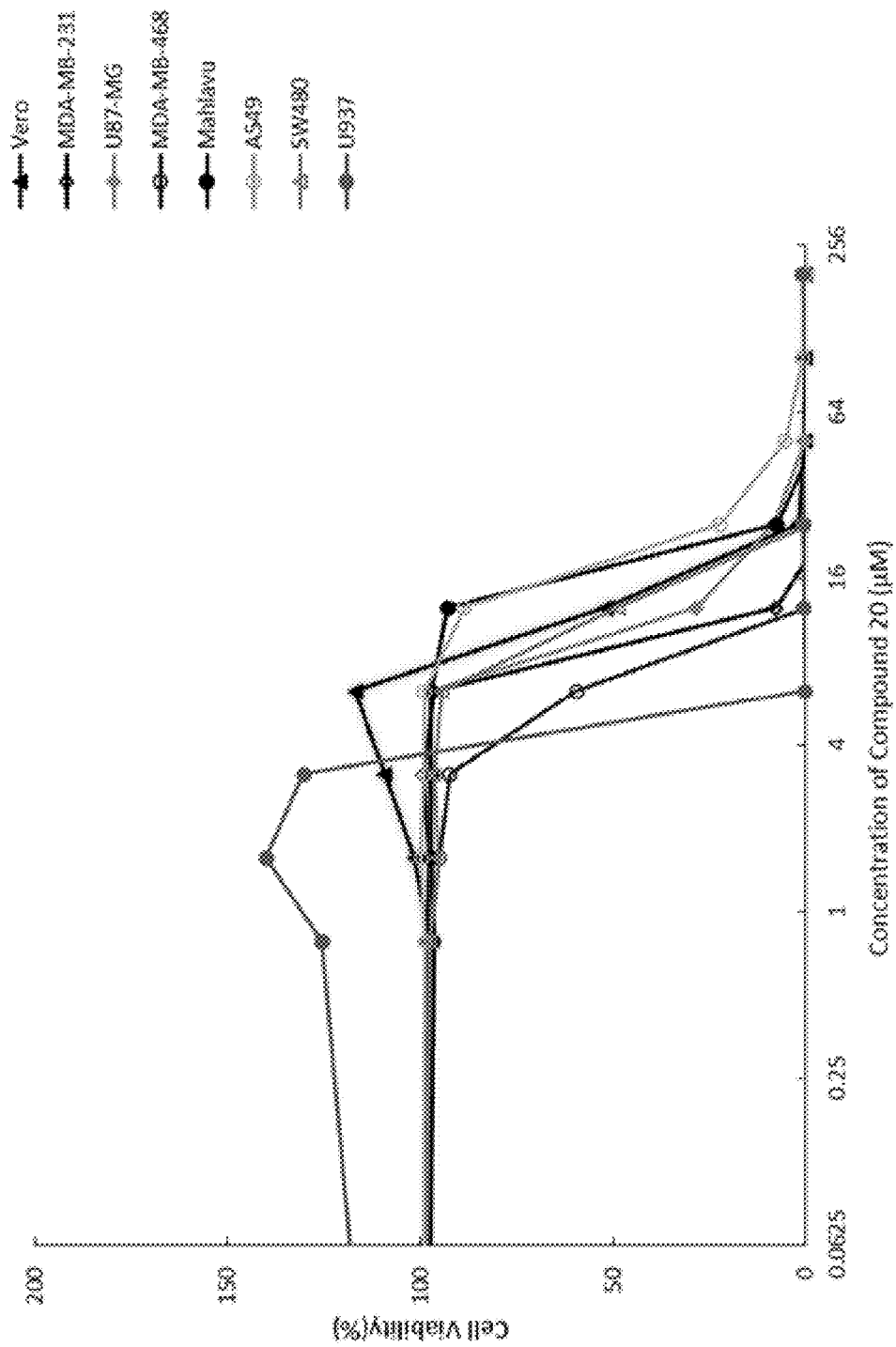
FIG. 23 is a diagram illustrating results of cell viability tests for compound 20 in example 20 according to the present invention.
Figure 24:
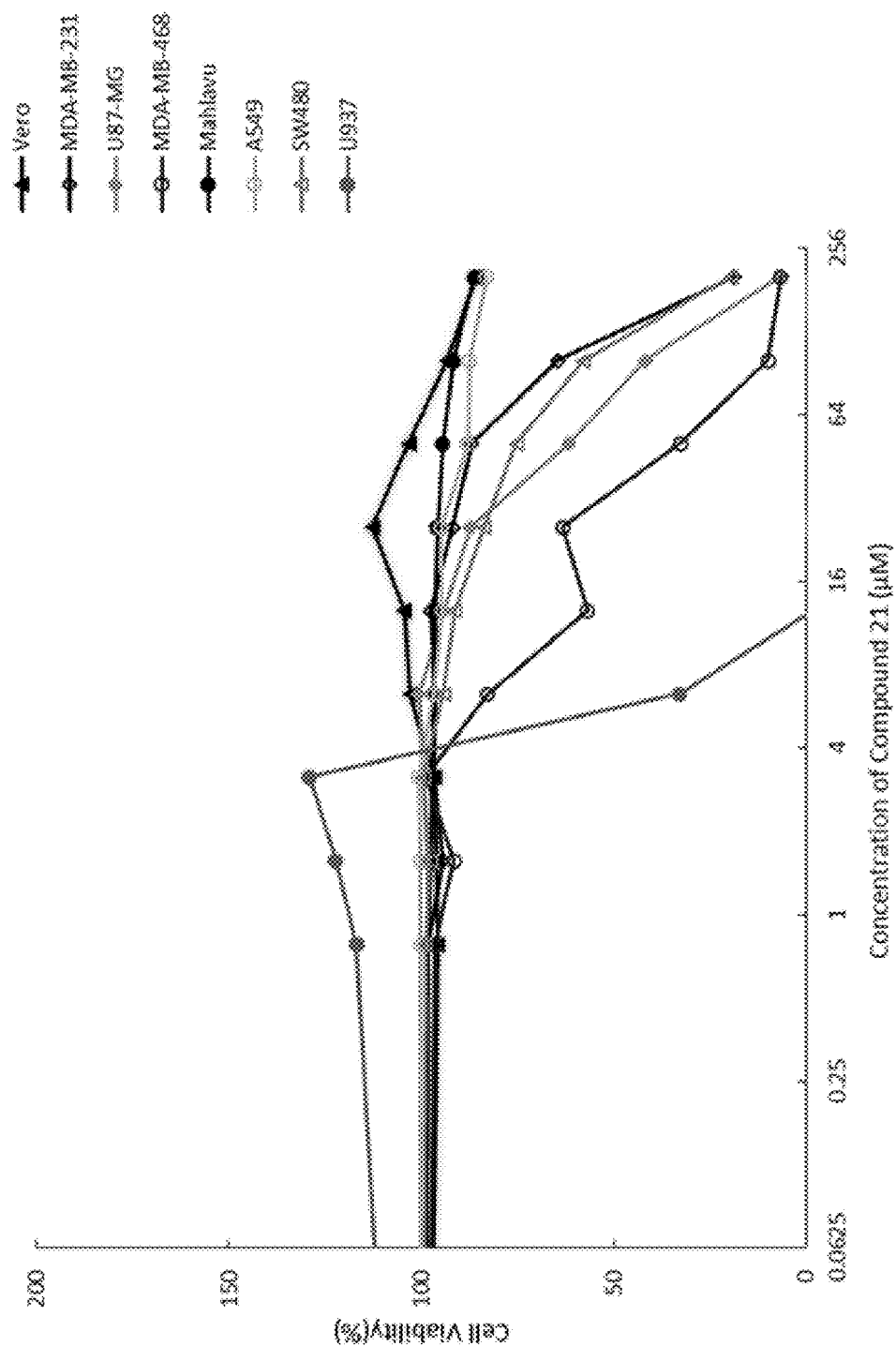
FIG. 24 is a diagram illustrating results of cell viability tests for compound 21 in example 21 according to the present invention.
Figure 25:
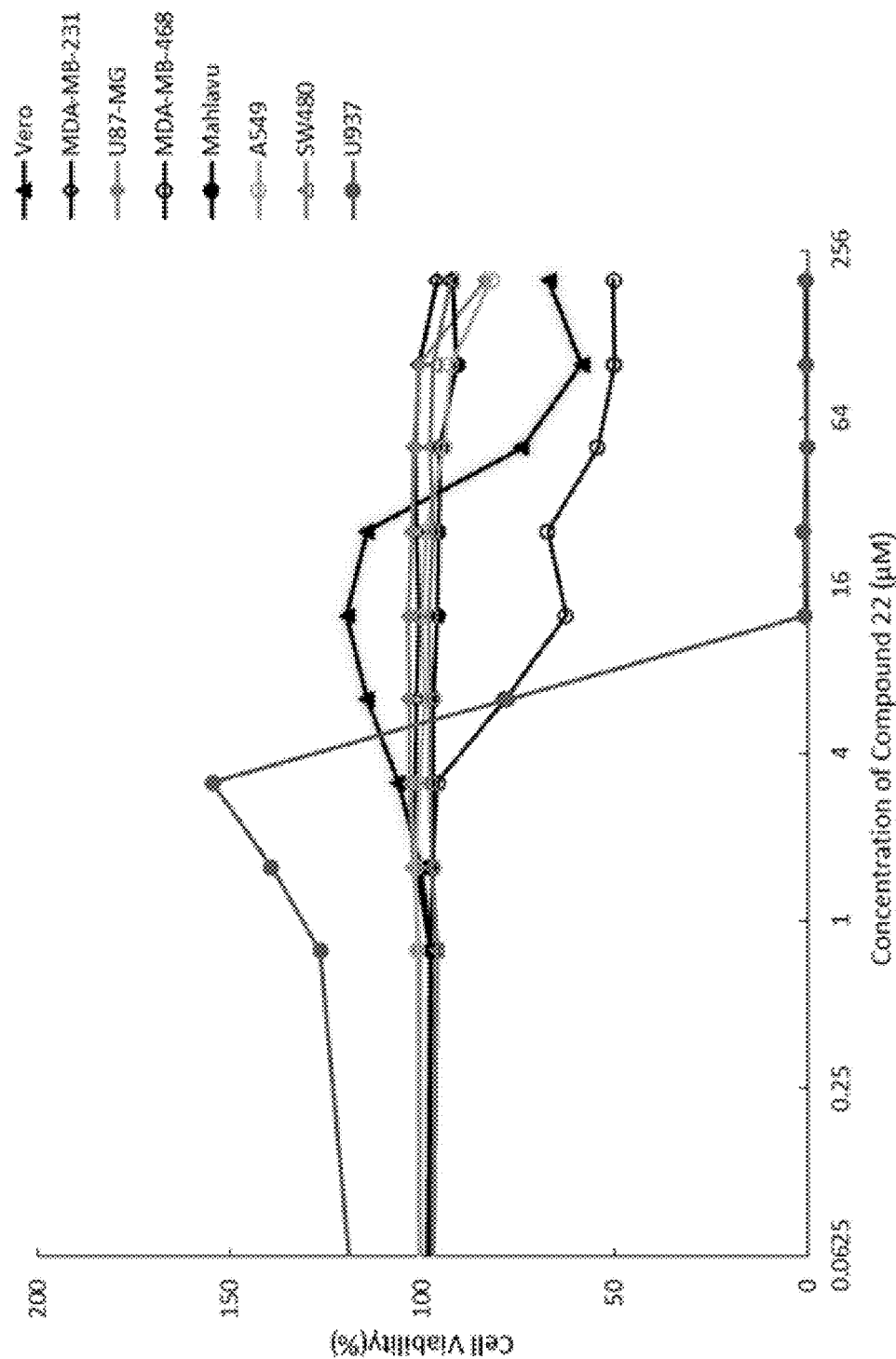
FIG. 25 is a diagram illustrating results of cell viability tests for compound 22 in example 22 according to the present invention.
Figure 26:
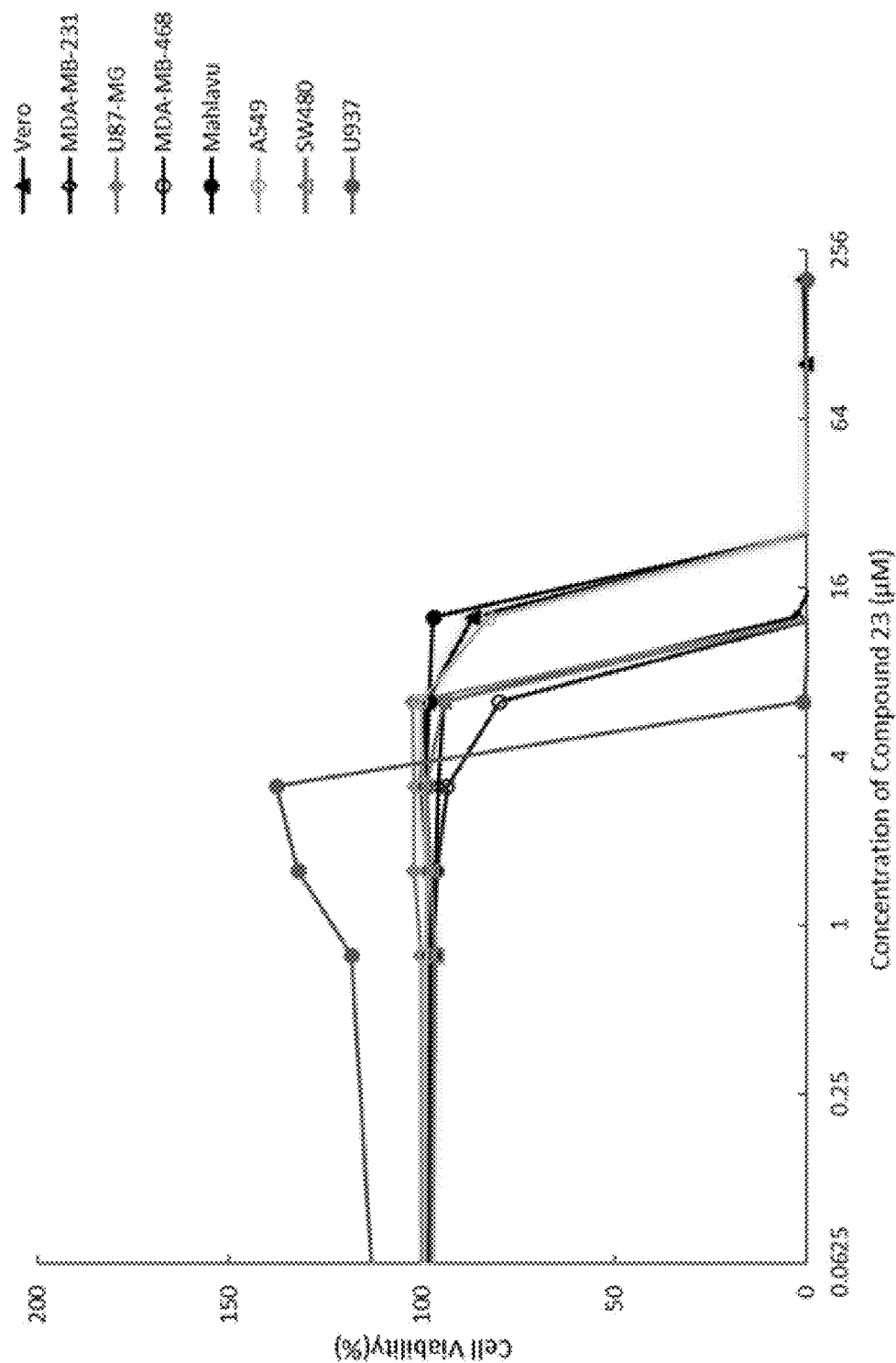
FIG. 26 is a diagram illustrating results of cell viability tests for compound 23 in example 23 according to the present invention.

Referring to FIGS. 1 to 3, flow diagrams illustrating separation of compounds 1 to 23 are shown. Firstly, air-dried balsam pear stem (at a dry weight of 1.0 kg) was ground by a grinder, and extracted with 10 L MeOH×3. The extracts were combined, filtered, and concentrated under reduced pressure. Liquid/liquid layer separation was performed with EtOAc/H2O. The upper EtOAc layer was concentrated under reduced pressure to give 35 g of a dark green crude extract.

The crude extract was subjected to preliminary separation by column chromatography using Silica gel 60, 70-230 mesh in combination with organic solvents n-hexane/EtOAc/MeOH at different ratios for gradient elution. Firstly, n-hexane was used as initial elution solvent, and the proportion of EtOAc was gradually increased to enhance the polarity of the eluent till the proportion of EtOAc reached 100%. Then, EtOAc was used as eluent, and the proportion of MeOH was gradually increased to enhance the polarity of the eluent till the proportion of MeOH reached 100%. Fractions were combined by $^1$H-NMR and TLC sheet to give 29 fractions in total, MC-1 to MC-29, respectively. The separation process diagram is shown in FIG. 1.

1. Purification and separation of compounds 1 and 2

Referring to FIG. 1, MC-19 (5 g) obtained using n-hexane/EtOAc (1:8) as eluent was subjected to reverse-phase column chromatography over silica gel (RP-18, 230 to 400 mesh) with MeOH/water (80:20) as eluent, and divided into two fractions, MC-19-R1 and MC-19-R2, respectively. Then, MC-19-R1 (4 g) was subjected to reverse-phase column chromatography over silica gel (RP-18, 230 to 400 mesh) with MeOH/water (60:40 to 100:0) as eluent, and divided into five fractions, MC-19-R1-R1 to MC-19-R1-R5, respectively. Then, MC-19-R1-R4 (3.3 g) was subjected to reverse-phase HPLC (RP-18, 5 μm, 250×25 mm, Merck, UV-vis detector), and separated and purified with MeOH/water (80:20) as eluent, to give 30 mg compound 1 and 40 mg compound 2.

2. Purification and Separation of Compounds 3 to 10

Referring to FIG. 2, 270 mg of MC-19-R1-R4 (3.3 g) was dissolved into pyridine (2 ml), and the reaction lasted for 3 h with addition of 4 drops of acetic anhydride and then was stopped with water. Liquid/liquid layer separation was performed with EtOAc. The upper EtOAc layer was concentrated under reduced pressure, and separated and purified using normal-phase column chromatography over silica gel and reverse-phase HPLC to give compounds 3 (7 mg), 4 (3.2 mg), 5 (5.2 mg), 6 (9 mg), 7 (26.2 mg), 8 (3.5 mg), 9 (10.6 mg), and 10 (24 mg).

3. Purification and Separation of Compound 11

Referring to FIG. 1, MC-18 (2 g) obtained using n-hexane/EtOAc (1:6) as eluent was subjected to normal-phase column chromatography over silica gel (Silica gel 60, 230-400 mesh) with n-hexane/EtOAc (1:1-0:1) as eluent, and divided into 11 fractions, MC-18-N1 to MC-18-N11, respectively. Then, MC-18-N4 (750 mg) obtained using n-hexane/EtOAc (1:3) as eluent was subjected to reverse-phase column chromatography over silica gel (RP-18, 230 to 400 mesh) with MeOH/water (70:30 to −100:0) as eluent, and divided into 11 fractions, MC-18-N4-R1 to MC-18-N4-R11, respectively. Then, MC-18-N4-R3 (119.3 mg) was subjected to reverse-phase HPLC (RP-18, 5 μm, 250×25 nm, Merck, UV-vis detector), and separated and purified with MeOH/water (75:25) as eluent, to give compound 11 (26 mg).

4. Purification and Separation of Compounds 12 to 14

Referring to FIG. 1, MC-27 (6.3 g) obtained using EtOAc/MeOH (2:1) as eluent was subjected to reverse-phase column chromatography (MCI) with MeOH/water (60:40-100:0) as eluent, and divided into 10 fractions, MC-27-M1 to MC-27-M10, respectively. MC-27-M2 (1 g) obtained using MeOH/water (80:20) as eluent was subjected to reverse-phase column chromatography over silica gel (RP-18, 230 to 400 mesh) with MeOH/water (60:40-100:0) as eluent, and divided into 8 fractions, MC-27-M2-R1 to MC-27-M2-R8, respectively. MC-27-M2-R5 (568.3 mg) was subjected to reverse-phase HPLC (RP-18, 5 μm, 250×25 mm, Merck, UV-vis detector), and separated and purified with MeOH/ water (77:23) as eluent, to give compound 12 (32 mg), compound 13 (30 mg), and compound 14 (5 mg).

5. Purification and Separation of Compounds 15 to 23

Referring to FIG. 3, 300 mg of MC-19-R1-R4 (3.3 g) was dissolved into MeOH (10 ml), and reacted with HCl (0.1 M, 1 ml) for 3.5 at RT, and then the reaction was stopped with water. Liquid/liquid layer separation was performed with EtOAc and water. The upper EtOAc layer was concentrated under reduced pressure, and separated and purified using reverse-phase column chromatography over silica gel and reverse-phase HPLC to give compounds 15 (14 mg), 16 (6 mg), 17 (14 mg), 18 (3 mg), 19 (3 mg), 20 (3 mg), 21 (2.9 mg), 22 (2 mg), 23 (12.2 mg).

Then, the obtained compounds 1 to 23 were further subjected to nuclear magnetic resonance spectroscopy, infrared spectroscopy, and mass spectrometry, so as to identify or measure their chemical structural characteristics, functionality, molecular weight, and spectral data, etc. The results of identification or measurement of compounds 1 to 23 are shown in Table 1.

TABLE 1

| Compound | Chemical structure | Spectral data |
| --- | --- | --- |
| Compound 1 | 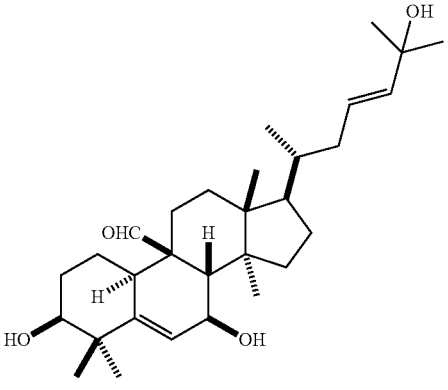<br>Molecular weight 472<br>3β,7β,25-trihydroxy-cucurbita-5,(23E)-diene-19-al | Molecular formula $C_{30}H_{48}O_4$; amorphous white powder; optical activity $[\alpha]^{26}_D$ +58.0 (c = 0.48, MeOH); IR(KBr) $\nu_{max}$ 3400 (br), 1715, 1660, 1470, 1460, 1385, 1155, 1090, 1050, 1020, 980 cm$^{-1}$; $^1$H-NMR ($C_5D_5N$, 400 MHz) $\delta_H$ 1.76 (1H, m, H-1), 2.09 (2H, m, H-2), 3.84 (1H, m, H-3), 6.28 (1H, br d, J = 4.1 Hz, H-6), 4.38 (1H, br d, J = 5.5 Hz, H-7), 2.39 (1H, br s, H-8), 2.69 (1H, m, H-10), 1.24 (1H, m, H-16), 0.88 (3H, s, H-18), 10.66 (1H, s, H-19), 0.99 (3H, d. J = 6.3 Hz, H-21), 1.85 (1H, m, H-22), 2.24 (1 H, m, H-22), 5.93 (1 H, m, H-23), 5.91 (1H, d, J = 15.4 Hz, H-24), 1.54, (3H, br s, H-26), 1.55 (3H, br s, H-27), 1.49 (3H, s, H-28), 1.19 (3H, s, H-29), 0.85 (3H, s, H-30); $^{13}$C-NMR ($C_5D_5N$, 100 MHz) $\delta_C$ 21.8 (t, C-1), 29.9 (t, C-2), 75.7 (d, C-3), 41.8 (s, C-4), 145.3 (s, C-5), 124.3 (d, C-6), 65.7 (d, C-7), 50.7 (d, C-8), 50.6 (s, C-9), 36.9 (d, C-10), 22.7 (t, C-11), 29.4 (t, C-12), 45.8 (s, C-13), 48.3 (s, C-14), 35.0 (t, C-15), 27.8 (t, C-16), 50.2 (d, C-17), 15.1 (q, C-18), 207.8 (d, C-19), 36.6 (d, C-20), 19.0 (q, C-21), 39.6 (t, C-22), 124.2 (d, C-23), 141.7 (s, C-24), 69.7 (s, C-25), 30.9 (q, C-26), 30.9 (q, C-27), 26.2 (q, C-28), 27.4 (q, C-29), 18.2 (q, C-30); EIMS m/z 472.3519 [M]$^+$ (calcd for $C_{30}H_{48}O_4$, 472.3552); FABMS m/z 495 [M + Na]$^+$, 511 [M + K]$^+$. A d . found C 73.89%, H 10.52%; calcd for $C_{30}H_{48}O_4.H_2O$, C 73.43%, H 10.27%. |
| Compound 2 | 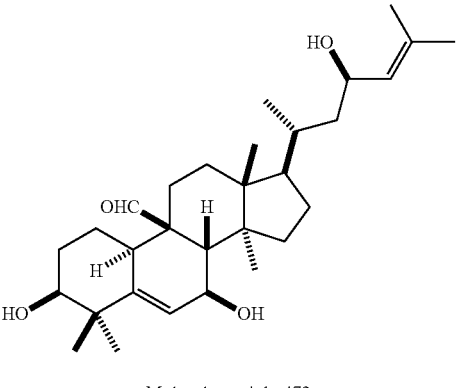<br>Molecular weight 472<br>(Momordicin I) | Molecular formula $C_{30}H_{48}O_4$; amorphous white powder; optical activity $[\alpha]_D$ +73.1 (c = 0.160, CHCl$_3$); IR $\nu_{max}$ 3418, 2945, 2871, 1708, 1663, 1467, 1382 cm$^{-1}$; $^1$H-NMR (MeOD, 400 MHz) $\delta_H$ 1.25, 1.08, 0.93, 0.82 (each 3 H, s), 3.55 (1H, br s, H-3), 5.91 (1H, d, J = 4.0 Hz, H-6), 4.00 (1H, d, J = 5.2 Hz, H-7), 2.40 (1H, m, H-8), 2.58 (1H, m, H-10), 9.88 (1H, s, H-19), 1.98 (1H, m, H-20), 1.00 (3H, d, J = 6.4 Hz, H-21), 4.41 (1H, dt, J$_1$, = 8.8 Hz, J$_2$ = 3.2 Hz, H-23), 5.16 (1H, d, J = 8.8 Hz, H-24), 1.70 (3H, s, H-26), 1.67 (3H, s, H-27); $^{13}$C-NMR (MeOD, 100 MHz) $\delta_C$ 22.2 (t, C-1), 30.3 (t, C-2), 77.1 (d, C-3), 42.3 (s, C-4), 147.3 (s, C-5), 124.0 (d, C-6), 66.9 (d, C-7), 50.8 (d, C-8), 52.1 (s, C-9), 37.7 (d, C-10), 23.3 (t, C-11), 29.8 (t, C-12), 46.8 (s, C-13), 49.0 (s, C-14), 35.6 (t, C-15), 28.6 (t, C-16), 51.3 (d, C-17), 15.3 (q, C-18), 209.7 (d, C-19), 33.7 (d, C-20), 19.3 (q, C-21), 45.6 (t, C-22), 66.6 (d, C-23), 133.4 (d, C-24), 130.5 (s, C-25), 18.8 (q, C-26), 26.0 (q, C-27), 25.9 (q, C-28), 27.8 (q, C-29), 18.1 (q, C-30); HRMS m/z 472.355 [M]$^+$ (calcd for $C_{30}H_{48}O_4$, 472.3552). |

TABLE 1-continued

| Compound | Chemical structure | Spectral data |
|---|---|---|
| Compound 3 | 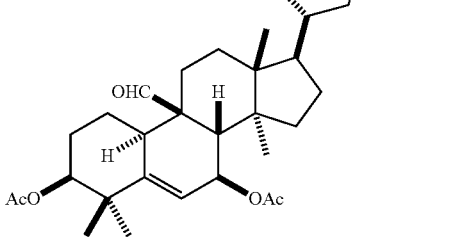<br>Molecular weight 598<br>Momordicin I 3,7,23,-triacetate | Molecular formula $C_{36}H_{54}O_7$; amorphous white powder; optical activity $[\alpha]^{26}_D$ −24.7 (c = 0.1, MeOH); IR (KBr) $\nu_{max}$ 3,430 (br), 2,948, 2,357, 1,726, 1,451, 1,376, 1,236, 1,025, 969, 754 cm$^{-1}$; $^1$H-NMR (CDCl$_3$, 400 MHz) $\delta_H$ 1.66 (1H, m, H-1α), 1.34 (1H, m, H-1β), 1.24 (1H, m, H-2α), 1.85 (1H, m, H-2β), 4.82 (1H, br s, H-3), 5.86 (1H, d, J = 4.8 Hz, H-6), 5.21 (1H, d, J = 5.6 Hz, H-7), 1.89 (1H, s, H-8), 2.56 (1H, m, H-10), 1.45 (2H, m, H-11α), 2.38 (2H, m, H-11β), 1.60 (2H, m, H-12α), 1.65 (2H, m, H-12β), 1.42 (2H, m, H-15), 1.36 (1H, m, H-16α), 1.92 (1H, m, H-16β), 1.47 (1H, m, H-17), 0.86 (3H, s, H-18), 9.83 (1H, s, H-19), 1.46 (1H, m, H-20), 0.95 (3H, d, J = 6.4 Hz, H-21), 1.78 (1H, m, H-22a), 1.06 (1H, m, H-22b), 5.60 (1H, ddd, J$_1$ = 10 Hz, J$_2$ = 8.8 Hz, J$_3$ = 3.2 Hz, H-23), 5.09 (1H, dd, J$_1$ = 8.8 Hz, J$_2$ = 1.2 Hz, H-24), 1.70 (3H, d, J = 1.2 Hz, H-26), 1.73 (3H, d, J = 1.2 Hz, H-27), 1.16 (3H, s, H-28), 1.13 (3H, s, H-29), 0.81 (3H, s, H-30), 2.04 (s, 3-OAc), 2.03 (s, 7-OAc), 2.02 (s, 23-OAc); $^{13}$C-NMR (CDCl$_3$; 100 MHz) $\delta_c$ 21.5 (t, C-1), 26.1 (t, C-2), 77.9 (d, C-3), 40.1 (s, C-4), 148.1 (s, C-5), 119.5 (d, C-6), 68.7 (d, C-7), 46.4 (d, C-8), 49.7 (s, C-9), 35.9 (d, C-10), 21.9 (t, C-11), 28.8 (t, C-12), 45.5 (s, C-13), 47.9 (s, C-14), 34.5 (t, C-15), 27.5 (t, C-16), 50.3 (d, C-17), 14.7 (q, C-18), 207.0 (d, C-19), 32.7 (d, C-20), 18.9 (q, C-21), 41.8 (t, C-22), 69.3 (d, C-23), 124.6 (d, C-24), 135.8 (s, C-25), 18.3 (q, C-26), 25.6 (q, C-27), 24.8 (q, C-28), 27.0 (q, C-29), 18.0 (q, C-30), 170.6 (s, 3-OAc), 21.9 (q, 3-OAc), 170.2 (s, 7-OAc), 21.3 (q, 7-OAc), 170.6 (q, 23-OAc), 21.5 (s, 23-OAc); ESIMS m/z 621 [M + Na]$^+$; HRESIMS m/z 621.3763 [M + Na]$^+$. |
| Compound 4 | 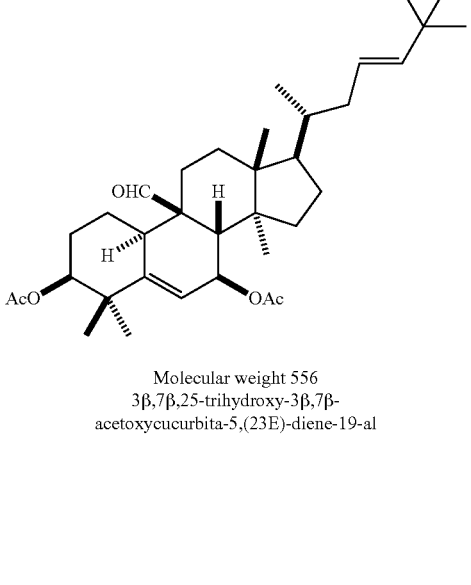<br>Molecular weight 556<br>3β,7β,25-trihydroxy-3β,7β-acetoxycucurbita-5,(23E)-diene-19-al | Molecular formula $C_{34}H_{52}O_6$; amorphous white powder; melt point 101-104° C.; IR (KBr) $\nu_{max}$ 3,450 (br), 1.735, 1,720, 1,610, 1,470, 1,380, 1,260, 1,220, 1,190, 1,020, 990, 940, 920 cm$^{-1}$; $^1$H-NMR (CDCl$_3$, 400 MHz) $\delta_H$ 1.62 (1H, m, H-1α), 1.56 (1H, m, H-1β), 1.93 (1H, m, H-2α), 1.77 (1H, m, H-2β), 4.82 (1H, br s, H-3), 5.88 (1H, d, J = 5.2 Hz, H-6), 5.19 (1H, d, J = 5.6 Hz, H-7), 1.91 (1H, s, H-8), 2.55 (1H, m, H-10), 1.42 (2H, m, H-11α), 2.38 (2H, m, H-11β), 1.56 (2H, m, H-12α), 1.64 (2H, m, H-12β), 1.43 (2H, m, H-15), 1.35 (1H, m, H-16α), 1.92 (1H, m, H-16β), 1.48 (1H, m, H-17), 0.87 (3H, s, H-18), 9.80 (1H, s, H-19), 1.52 (1H, m, H-20), 0.91 (3H, d, J = 5.5 Hz, H-21), 1.72 (1H, m, H-22a), 2.15 (1H, m, H-22b), 5 (1H, ddd, J$_1$ = 15.6 Hz, J$_2$ = 8.4 Hz, J$_3$ = 5.6 Hz, H-23), 5.59 (1H, d, J = 5.6 Hz, J, H-24), 1.31 (3H, d, J = 1.2 Hz, H-26), 1.31 (3H, d, J = 1.2 Hz, H-27), 1.26 (3H, s, H-28), 1.09 (3H, s, H-29), 0.81 (3H, s, H-30), 2.04 (s, 3-OAc), 2.01 (s, 7-OAc); $^{13}$C-NMR (CDCl$_3$, 100 MHz) $\delta_c$ 20.9 (t, C-1), 28.5 (t, C-2), 76.2 (d, C-3), 41.6 (s, C-4), 149.5 (s, C-5), 120.2 (d, C-6), 68.7 (d, C-7), 46.1 (d, C-8), 49.9 (s, C-9), 35.8 (d, C-10), 22.1 (t, C-11), 28.8 (t, C-12), 45.5 (s, C-13), 47.8 (s, C-14), 34.6 (t, C-15), 27.3 (t, C-16), 49.8 (d, C-17), 14.9 (q, C-18), 206.9 (d, C-19), 36.1 (d, C-20), 18.7 (q, C-21), 39.0 (t, C-22), 125.1 (d, C-23), 139.7 (d, C-24), 70.7 (s, C-25), 29.9 (q, C-26), 30.0 (q, C-27), 25.2 (q, C-28), 27.0 (q, C-29), 18.0 (q, C-30), 170.6 (s, 3-OAc), 21.9 (q, 3-OAc), 170.1 (s, 7-OAc), 21.3 (q, 7-OAc); EIMS m/z 478.3462 [M - HOAc - H$_2$O]$^+$ (calcd for $C_{32}H_{48}O_4$, 478.3447); FABMS m/z 579 [M + Na]$^+$, 595 [M + Kl]$^+$. |

TABLE 1-continued

| Compound | Chemical structure | Spectral data |
|---|---|---|
| Compound 5 | 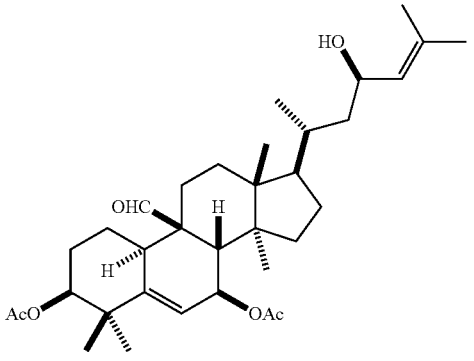<br>Molecular weight 556<br>Momordicin I 3,7-diacetate | Molecular formula $C_{34}H_{52}O_6$; amorphous white powder; optical activity $[\alpha]^{26}_D$ −0.6 (c = 0.1, MeOH); IR (KBr) $\nu_{max}$ 3,427, 2,926, 2,859, 2,353, 1,725, 1,544, 1,455, 1,373, 1,244, 1,016, 976, 673 cm$^{-1}$; $^1$H-NMR (CDCl$_3$, 400 MHz) $\delta_H$ 1.66 (1H, m, H-1α), 1.34 (1H, m, H-1β), 1.24 (1H, m, H-2α), 1.85 (1H, m, H-2β), 4.82 (1H, br s, H-3), 5.86 (1H, d, J = 4.8 Hz, H-6), 5.21 (1H, d. J = 5.6 Hz, H-7), 1.89 (1H, s, H-8), 2.56 (1H, m, H-10), 1.46 (2H, m, H-11α), 2.36 (2H, m, H-11β), 1.60 (2H, m, H-12α), 1.66 (2H, m, H-12β), 1.45 (2H, m, H-15), 1.32 (1H, m, H-16α), 1.92 (1H, m, H-16β), 1.48 (1H, m, H-17), 0.84 (3H, s, H-18), 9.78 (1H, s, H-19), 1.51 (1H, m, H-20), 0.94 (3H, d, J = 5.5 Hz, H-21), 1.80 (1H, m, H-22a), 1.10 (1H, m, H-22b), 4.46 (1H, ddd, J$_1$ = 10 Hz, J$_2$ = 8.8 Hz, J$_3$ = 3.2 Hz, H-23), 5.08 (1H, dd, J$_1$ = 8.8 Hz, J$_2$ = 1.2 Hz, H-24), 1.71 (3H, d, J = 1.2 Hz, H-26), 1.68 (3H, d, J = 1.2 Hz, H-27), 1.24 (3H, s, H-28), 1.07 (3H, s, H-29), 0.80 (3H, s, H-30), 2.04 (s, 3-OAc), 2.03 (s, 7-OAc); $^{13}$C-NMR (CDCl$_3$, 100 MHz) $\delta_c$ 21.5 (t, C-1), 26.1 (t, C-2), 77.9 (d, C-3), 40.1 (s, C-4), 148.1 (s, C-5), 119.5 (d, C-6), 68.7 (d, C-7), 46.4 (d, C-8), 49.7 (s, C-9), 35.9 (d, C-10), 22.1 (t, C-11), 28.8 (t, C-12), 45.5 (s, C-13), 47.8 (s, C-14), 34.5 (t, C-15), 27.5 (t, C-16), 50.3 (d, C-17), 14.7 (q, C-18), 206.4 (d, C-19), 32.7 (d, C-20), 18.9 (q, C-21), 41.9 (t, C-22), 69.4 (d, C-23), 124.6 (d, C-24), 135.7 (s, C-25), 18.3 (q, C-26), 25.6 (q, C-27), 25.0 (q, C-28), 27.0 (q, C-29), 18.0 (q, C-30), 170.6 (s, 3-OAc), 21.9 (q, 3-OAc), 170.2 (s, 7-OAc), 21.3 (q, 7-OAc); ESIMS m/z 579 [M + Na]$^+$; HRESIMS m/z 579.3654 [M + Na]$^+$ |
| Compound 6 | 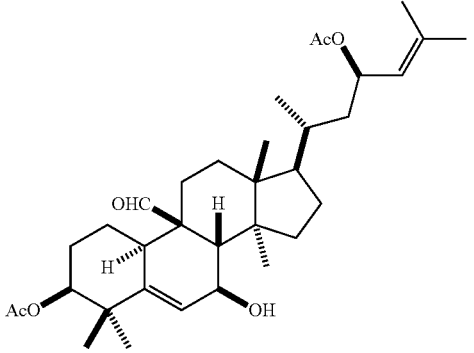<br>Molecular weight 556<br>Momordicin I 3,23-diacetate | Molecular formula $C_{34}H_{52}O_6$; amorphous white powder; optical activity $[\alpha]^{26}_D$ +4.0 (c = 0.1, MeOH); IR (KBr) $\nu_{max}$ 3,448 (br), 2,936, 2,348, 1,723, 1,455, 1,376, 1,249, 1,013, 986, 754 cm$^{-1}$; $^1$H-NMR (CDCl$_3$, 400 MHz) $\delta_H$ 1.66 (1H, m, H-1α), 1.34 (1H, m, H-1β), 1.24 (1H, m, H-2α), 1.85 (1H, m, H-2β), 4.82 (1H, br s, H-3), 5.86 (1H, d, J = 4.8 Hz, H-6), 5.21 (1H, d, J = 5.6 Hz, H-7), 1.89 (1H, s, H-8), 2.56 (1H, m, H-10), 1.46 (2H, m, H-11α), 2.36 (2H, m, H-11β), 1.60 (2H, m, H-12α), 1.66 (2H, m, H-12β), 1.45 (2H, m, H-15), 1.32 (1H, m, H-16α), 1.92 (1H, m, H-16β), 1.48 (1H, m, H-17), 0.84 (3H, s, H-18), 9.78 (1H, s, H-19), 1.51 (1H, m, H-20), 0.94 (3H, d, J = 5.5 Hz, H-21), 1.80 (1H, m, H-22a), 1.10 (1H, m, H-22b), 5.58 (1H, ddd, J$_1$ = 10 Hz, J$_2$ = 8.8 Hz, J$_3$ = 3.2 Hz, H-23), 5.08 (1H, dd, J$_1$ = 8.8 Hz, J$_2$ = 1.2 Hz, H-24), 1.71 (3H, d, J = 1.2 Hz, H-26), 1.68 (3H, d, J = 1.2 Hz, H-27), 1.24 (3H, s, H-28), 1.07 (3H, s, H-29), 0.80 (3H, s, H-30), 2.04 (s, 3-OAc), 2.02 (s, 23-OAc); $^{13}$C-NMR (CDCl$_3$, 100 MHz) $\delta_c$ 21.5 (t, C-1), 26.1 (t, C-2), 77.9 (d, C-3), 40.1 (s, C-4), 148.1 (s, C-5), 119.5 (d, C-6), 68.7 (d, C-7), 46.4 (d, C-8), 49.7 (s, C-9), 35.9 (d, C-10), 22.1 (t, C-11), 28.8 (t, C-12), 45.5 (s, C-13), 47.8 (s, C-14), 34.5 (t, C-15), 27.5 (t, C-16), 50.3 (d, C-17), 14.7 (q, C-18), 206.4 (d, C-19), 32.7 (d, C-20), 18.9 (q, C-21), 41.9 (t, C-22), 69.4 (d, C-23), 124.6 (d, C-24), 135.7 (s, C-25), 18.3 (q, C-26), 25.6 (q, C-27), 25.0 (q, C-28), 27.0 (q, C-29), 18.0 (q, C-30), 170.6 (s, 3-OAc), 21.9 (q, 3-OAc), 170.6 (q, 23-OAc), 21.5 (s, 23-OAc); ESIMS m/z 579 [M + Na]$^+$; HRESIMS m/z 579.3654 [M + Na]$^+$. |

TABLE 1-continued

| Compound | Chemical structure | Spectral data |
|---|---|---|
| Compound 7 | 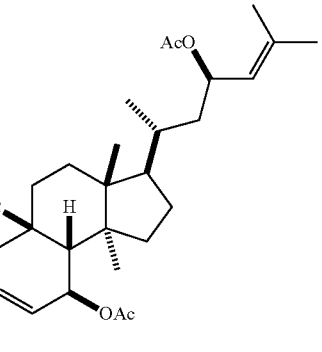<br>Molecular weight 556<br>Momordicin I 7,23,-diacetate | Molecular formula $C_{34}H_{52}O_6$; amorphous white powder; optical activity $[\alpha]^{26}_D$ +83.1 (c = 0.1, MeOH); IR (KBr) $\nu_{max}$ 3,461 (br), 2,948, 2,879, 2,357, 1,723, 1,451, 1,376, 1,244, 1,017, 934, 758 cm$^{-1}$; $^1$H-NMR (CDCl$_3$, 400 MHz) $\delta_H$ 1.62 (1H, m, H-1α), 1.54 (1H, m, H-1β), 1.78 (1H, m, H-2α), 1.94 (1H, m, H-2β), 3.60 (1H, br s, H-3), 5.85 (1H, d, J = 5.2 Hz, H-6), 5.16 (1H, d, J = 5.2 Hz, H-7), 1.90 (1H, s, H-8), 2.53 (1H, m, H-10), 1.46 (2H, m, H-11α), 2.36 (2H, m, H-11β), 1.60 (2H, m, H-12α), 1.66 (2H, m, H-12β), 1.45 (2H, m, H-15), 1.32 (1H, m, H-16α), 1.92 (1H, m, H-16β), 1.48 (1H, m, H-17), 0.84 (3H, s, H-18), 9.78 (1H, s, H-19), 1.51 (1H, m, H-20), 0.94 (3H, d, J = 5.5 Hz, H-21), 1.80 (1H, m, H-22a), 1.10 (1H, m, H-22b), 5.58 (1H, ddd, $J_1$ = 10 Hz, $J_2$ = 8.8 Hz, $J_3$ = 3.2 Hz, H-23), 5.08 (1H, dd, $J_1$ = 8.8 Hz, $J_2$ = 1.2 Hz, H-24), 1.71 (3H, d, J = 1.2 Hz, H-26), 1.68 (3H, d, J = 1.2 Hz, H-27), 1.24 (3H, s, H-28), 1.07 (3H, s, H-29), 0.80 (3H, s, H-30), 2.00 (s, 7-OAc), 1.98 (s, 23-OAc); $^{13}$C-NMR (CDCl$_3$, 100 MHz) $\delta_c$ 20.9 (t, C-1), 28.5 (t, C-2), 76.1 (d, C-3), 41.6 (s, C-4), 148.6 (s, C-5), 120.1 (d, C-6), 68.7 (d, C-7), 46.0 (d, C-8), 49.8 (s, C-9), 35.8 (d, C-10), 22.1 (t, C-11), 28.8 (t, C-12), 45.5 (s, C-13), 47.8 (s, C-14), 34.5 (t, C-15), 27.5 (t, C-16), 50.3 (d, C-17), 14.7 (q, C-18), 206.4 (d, C-19), 32.7 (d, C-20), 18.9 (q, C-21), 41.9 (t, C-22), 69.4 (d, C-23), 124.6 (d, C-24), 135.7 (s, C-25), 18.3 (q, C-26), 25.6 (q, C-27), 25.0 (q, C-28), 27.0 (q, C-29), 18.0 (q, C-30), 170.2 (s, 7-OAc), 21.3 (q, 7-OAc), 170.6 (q, 23-OAc), 21.5 (s, 23-OAc); ESIMS m/z 579 [M + Na]$^+$; HRESIMS m/z 579.3654 [M + Na]$^+$. |
| Compound 8 | 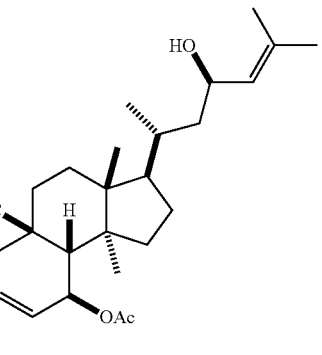<br>Molecular weight 514<br>Momordicin I 7-acetate | Molecular formula $C_{32}H_{50}O_5$; amorphous white powder; optical activity $[\alpha]^{26}_D$ +115.8 (c = 0.1, MeOH); IR (KBr) $\nu_{max}$ 3,448 (br), 2,947, 2,883, 2,356, 1,717, 1,460, 1,374, 1,235, 1,013, 939, 754 cm$^{-1}$; $^1$H-NMR (CDCl$_3$, 400 MHz) $\delta_H$ 1.66 (1H, m, H-1α), 1.57 (1H, m, H-1β), 1.80 (1H, m, H-2α), 1.96 (1H, m, H-2β), 3.61 (1H, br s, H-3), 5.87 (1H, d, J = 5.6 Hz, H-6), 5.19 (1H, d, J = 5.6 Hz, H-7), 1.92 (1H, s, H-8), 2.55 (1H, m, H-10), 1.48 (2H, m, H-11α), 2.36 (2H, m, H-11β), 1.66 (2H, m, H-12α), 1.72 (2H, m, H-12β), 1.44 (2H, m, H-15), 1.40 (1H, m, H-16α), 1.96 (1H, m, H-16β), 1.50 (1H, m, H-17), 0.89 (3H, s, H-18), 9.79 (1H, s, H-19), 1.75 (1H, m, H-20), 0.99 (3H, d, J = 5.5 Hz, H-21), 1.65 (1H, m, H-22a), 1.04 (1H, m, H-22b), 4.46 (1H, ddd, $J_1$ = 10 Hz, $J_2$ = 8.8 Hz, $J_3$ = 3.2 Hz, H-23), 5.19 (1H, dd, $J_1$ = 8.8 Hz, $J_2$ = 1.2 Hz, H-24), 1.70 (3H, d, J = 1.2 Hz, H-26), 1.69 (3H, d, J = 1.2 Hz, H-27), 1.26 (3H, s, H-28), 1.08 (3H, s, H-29), 0.81 (3H, s, H-30), 2.00 (s, 7-OAc); $^{13}$C-NMR (CDCl$_3$, 100 MHz) $\delta_c$ 20.9 (t, C-1), 28.5 (t, C-2), 76.2 (d, C-3), 41.6 (s, C-4), 148.5 (s, C-5), 120.2 (d, C-6), 68.7 (d, C-7), 46.0 (d, C-8), 49.9 (s, C-9), 35.8 (d, C-10), 22.2 (t, C-11), 28.9 (t, C-12), 45.6 (s, C-13), 47.8 (s, C-14), 34.5 (t, C-15), 27.6 (t, C-16), 50.7 (d, C-17), 14.9 (q, C-18), 206.3 (d, C-19), 32.6 (d, C-20), 18.7 (q, C-21), 44.4 (t, C-22), 65.9 (d, C-23), 129.0 (d, C-24), 133.9 (s, C-25), 25.7 (q, C-26), 18.7 (q, C-27), 25.2 (q, C-28), 27.0 (q, C-29), 18.1 (q, C-30), 170.2 (s, 7-OAc), 21.3 (q, 7-OAc); ESIMS m/z 537 [M + Na]$^+$; HRESIMS m/z 537.3549 [M + Na]$^+$. |

TABLE 1-continued

| Compound | Chemical structure | Spectral data |
|---|---|---|
| Compound 9 | 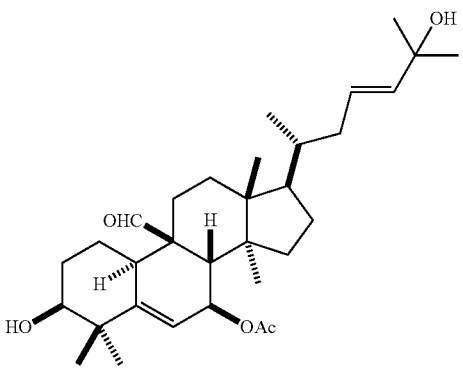<br>Molecular weight 514<br>3β,7β,25-trihydroxy-7β-acetoxycucurbita-5,(23E)-diene-19-al | Molecular formula $C_{32}H_{50}O_5$; amorphous white powder; optical activity $[\alpha]^{26}_D$ −0.6 (c = 0.1, MeOH); IR (KBr) $\nu_{max}$ 3,450 (br), 1,735, 1,720, 1,610, 1,470, 1,380, 1,260, 1,220, 1,190, 1,020, 990, 940, 920 cm$^{-1}$; $^1$H-NMR (CDCl$_3$, 400 MHz) $\delta_H$ 1.62 (1H, m, H-1α), 1.56 (1H, m, H-1β), 1.93 (1H, m, H-2α), 1.77 (1H, m, H-2β), 3.62 (1H, br s, H-3), 5.88 (1H, d, J = 5.2 Hz, H-6), 5.19 (1H, d, J = 5.6 Hz, H-7), 1.91 (1H, s, H-8), 2.55 (1H, m, H-10), 1.42 (2H, m, H-11α), 2.38 (2H, m, H-11β), 1.56 (2H, m, H-12α), 1.64 (2H, m, H-12β), 1.43 (2H, m, H-15), 1.35 (1H, m, H-16α), 1.92 (1H, m, H-16β), 1.48 (1H, m, H-17), 0.87 (3H, s, H-18), 9.80 (1H, s, H-19), 1.52 (1H, m, H-20), 0.91 (3H, d, J = 5.5 Hz, H-21), 1.72 (1H, m, H-22a), 2.15 (1H, m, H-22b), 5 (1H, ddd, J$_1$ = 15.6 Hz, J$_2$ = 8.4 Hz, J$_3$ = 5.6 Hz, H-23), 5.59 (1H, d, J = 5.6 Hz, J, H-24), 1.31 (3H, d, J = 1.2 Hz, H-26), 1.31 (3H, d, J = 1.2 Hz, H-27), 1.26 (3H, s, H-28), 1.09 (3H, s, H-29), 0.81 (3H, s, H-30), 2.01 (s, 7-OAc); $^{13}$C-NMR (CDCl$_3$, 100 MHz) $\delta_c$ 20.9 (t, C-1), 28.5 (t, C-2), 76.2 (d, C-3), 41.6 (s, C-4), 149.5 (s, C-5), 120.2 (d, C-6), 68.7 (d, C-1), 46.1 (d, C-8), 49.9 (s, C-9), 35.8 (d, C-10), 22.1 (t, C-11), 28.8 (t, C-12), 45.5 (s, C-13), 47.8 (s, C-14), 34.6 (t, C-15), 27.3 (t, C-16), 49.8 (d, C-17), 14.9 (q, C-18), 206.9 (d, C-19), 36.1 (d, C-20), 18.7 (q, C-21), 39.0 (t, C-22), 125.1 (d, C-23), 139.7 (d, C-24), 70.7 (s, C-25), 29.9 (q, C-26), 30.0 (q, C-27), 25.2 (q, C-28), 27.0 (q, C-29), 18.0 (q, C-30), 170.1 (s, 7-OAc), 21.3 (q, 7-OAc); ESIMS m/z 537 [M + Na]$^+$; HRESIMS m/z 537.3549 [M + Na]$^+$. |
| Compound 10 | 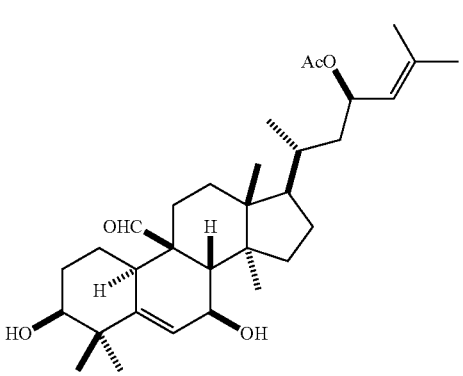<br>Molecular weight 514<br>Momordicin I 23-acetate | Molecular formula $C_{32}H_{50}O_5$; amorphous white powder; optical activity $[\alpha]^{26}_D$ −110.2 (c = 0.1, MeOH); IR (KBr) $\nu_{max}$ 3,434 (br), 2,944, 2,353, 1,718, 1,647, 1,459, 1,376, 1,244, 1,113, 1,074, 973, 754 cm$^{-1}$; $^1$H-NMR (CDCl$_3$, 400 MHz) $\delta_H$ 1.62 (1H, m, H-1α), 1.54 (1H, m, H-1β), 1.78 (1H, m, H-2α), 1.94 (1H, m, H-2β), 3.60 (1H, br s, H-3), 5.85 (1H, d, J = 5.2 Hz, H-6), 4.02 (1H, d, J = 5.2 Hz, H-7), 1.90 (1H, s, H-8), 2.53 (1H, m, H-10), 1.46 (2H, m, H-11α), 2.36 (2H, m, H-11β), 1.60 (2H, m, H-12α), 1.66 (2H, m, H-12β), 1.45 (2H, m, H-15), 1.32 (1H, m, H-16α), 1.92 (1H, m, H-16β), 1.48 (1H, m, H-17), 0.84 (3H, s, H-18), 9.78 (1H, s, H-19), 1.51 (1H, m, H-20), 0.94 (3H, d, J = 5.5 Hz, H-21), 1.80 (1H, m, H-22a), 1.10 (1H, m, H-22b), 5.58 (1H, ddd, J$_1$ = 10 Hz, J$_2$ = 8.8 Hz, J$_3$ = 3.2 Hz, H-23), 5.08 (1H, dd, J$_1$ = 8.8 Hz, J$_2$ = 1.2 Hz, H-24), 1.71 (3H, d, J = 1.2 Hz, H-26), 1.68 (3H, d, J = 1.2 Hz, H-27), 1.24 (3H, s, H-28), 1.07 (3H, s, H-29), 0.80 (3H, s, H-30), 1.98 (s, 23-OAc); $^{13}$C-NMR (CDCl$_3$, 100 MHz) $\delta_c$ 20.9 (t, C-1), 28.5 (t, C-2), 76.1 (d, C-3), 41.6 (s, C-4), 148.6 (s, C-5), 120.1 (d, C-6), 68.7 (d, C-7), 46.0 (d, C-8), 49.8 (s, C-9), 35.8 (d, C-10), 22.1 (t, C-11), 28.8 (t, C-12), 45.5 (s, C-13), 47.8 (s, C-14), 34.5 (t, C-15), 27.5 (t, C-16), 50.3 (d, C-17), 14.7 (q, C-18), 206.4 (d, C-19), 32.7 (d, C-20), 18.9 (q, C-21), 41.9 (t, C-22), 69.4 (d, C-23), 124.6 (d, C-24), 135.7 (s, C-25), 18.3 (q, C-26), 25.6 (q, C-27), 25.0 (q, C-28), 27.0 (q, C-29), 18.0 (q, C-30), 170.6 (q, 23-OAc), 21.5 (s, 23-OAc); ESIMS m/z 537 [M + Na]$^+$; HRESIMS m/z 537.3549 [M + Na]$^+$. |

TABLE 1-continued

| Compound | Chemical structure | Spectral data |
|---|---|---|
| Compound 11 | 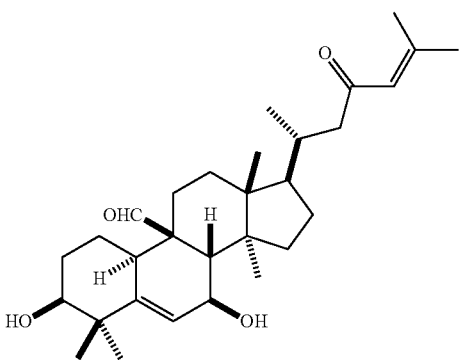<br>Molecular weight 470<br>Kuguacin N | Molecular formula $C_{30}H_{46}O_4$; amorphous white powder; melt point 140-143° C.; optical activity $[\alpha]^{20}_D$ −5.9 (c = 0.13, MeOH) ; UV (MeOH) $\lambda_{max}$ log $\epsilon$) 228 (3.6); IR (KBr) $\nu_{max}$ 3412, 2950, 2876, 1712, 1619, 1465, 1445, 1249, 1040, 944 cm$^{-1}$; $^1$H-NMR ($C_5D_5N$, 500 MHz) $\delta_H$ 2.09 (1H, m, H-1), 1.75 (1H, m, H-1), 2.09 (1H, m, H-2), 1.92 (1H, m, H-2), 3.82 (1H, br s, H-3), 6.28 (1H, br d, J = 4.7 Hz, H-6), 4.36 (1H, br d, J = 5.1 Hz, H-7), 2.37 (1H, s, H-8), 2.0 (1H, m, H-10), 2.66 (2H, m, H-11), 1.57 (2H, m, H-11), 1.60 (2H, m, H-12), 1.37 (2H, m, H-15), 1.94 (1H, m, H-16), 1.37 (1H, m, H-16), 1.57 (1H, m, H-17), 0.89 (3H, s, H-18), 10.65 (1H, s, H-19), 2.17 (1H, m, H-20), 1.03 (3H, d, J = 5.5 Hz, H-21), 2.54 (1H, d, J = 12.2 Hz, H-22), 2.17 (1H, m, H-22), 6.17 (1H, s, H-24), 1.75 (3H, s, H-26), 2.21 (3H, s, H-27), 1.19 (3H, s, H-28), 1.48 (3H, s, H-29), 0.86 (3H, s, H-30); $^{13}$C-NMR ($C_5D_5N$, 125 MHz) $\delta_C$ 21.8 (t, C-1), 29.9 (t, C-2), 75.7 (d, C-3), 41.8 (s, C-4), 145.8 (s, C-5), 124.3 (d, C-6), 65.7 (d, C-7), 50.7 (d, C-8), 50.6 (s, C-9), 36.9 (d, C-10), 22.7 (t, C-11), 29.5 (t, C-12), 45.9 (s, C-13), 48.4 (s, C-14), 34.9 (t, C-15), 28.0 (t, C-16), 50.7 (d, C-17), 14.7 (q, C-18), 207.8 (d, C-19), 33.5 (d, C-20), 20.0 (q, C-21), 51.9 (t, C-22), 200.7 (s, C-23), 124.9 (d, C-24), 154.1 (s, C-25), 27.3 (q, C-26), 20.6 (q, C-27), 27.4 (q, C-28), 26.2 (q, C-29), 18.3 (q, C-30); EIMS m/z 470 [M]$^+$; HRESIMS m/z 493.3297 [M + Na]$^+$ (calcd for $C_{30}H_{46}O_4Na$, 493.3293). |
| Compound 12 | 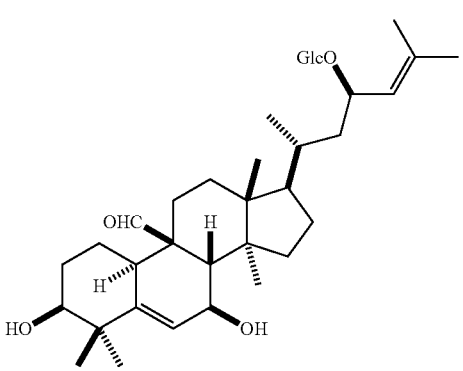<br>Molecular weight 635<br>Momordicin II | Molecular formula $C_{36}H_{58}O_9$; amorphous white powder; optical activity $[\alpha]^{22}_D$ +46.7 (c = 0.3, MeOH); $^1$H-NMR ($C_5D_5N$, 500 MHz) $\delta_H$ 0.86, 0.88, 1.16, 1.47 (each 3H, s), 1.18, 1.53, 1.57, 1.58, 1.93, 1.94, 1.96, 2.71 (each 1H), 1.35, 1.55, 1.93 (each 2H), 3.80 (1H, br s, H-3), 6.27 (1H, d, J = 4.4 Hz, H-6), 4.33 (1H, d, J = 4.6 Hz, H-7), 2.36 (1H, s, H-8), 2.71 (1H, m, H-10), 10.73, (1H, s, H-19), 2.06 (1H, m, H-20), 1.19 (3H, d, J = 6.6 Hz, H-21), 4.94 (1H, d, J = 7.8 Hz, H-23), 5.61 (1H, d, J = 7.8 Hz, H-24), 1.69, 1.75 (each 3H, s, H-26 and H-27), 4.94 (1H, d, J = 7.8 Hz, Glc-1), 4.01 (1H, br t, Glc-2), 4.21 (1H, d, Glc-3), 4.22 (1H, d, Glc-4), 3.88 (1H, br s, Glc-5), 4.34 (1H, dd, J$_1$ = 9.1 Hz, J$_2$ = 5.2 Hz, Glc-6a), 4.46 (1H, dd, J$_1$ = 9.1 Hz, J$_2$ = 1.9 Hz, Glc-6b); $^{13}$C-NMR ($C_5D_5N$, 125 MHz) $\delta_C$ 21.7 (t, C-1), 29.9 (t, C-2), 75.6 (d, C-3), 41.8 (s, C-4), 145.7 (s, C-5), 124.3 (d, C-6), 65.7 (d, C-7), 50.6 (d, C-8), 50.6 (s, C-9), 36.8 (d, C-10), 22.7 (t, C-11), 29.6 (t, C-12), 45.9 (s, C-13), 48.3 (s, C-14), 34.9 (t, C-15), 27.8 (t, C-16), 51.2 (d, C-17), 14.9 (q, C-18), 207.5 (d, C-19), 32.7 (d, C-20), 19.4 (q, C-21), 43.8 (t, C-22), 75.3 (d, C-23), 129.1 (d, C-24), 132.2 (s, C-25), 18.3 (q, C-26), 26.2 (q, C-27), 25.8 (q, C-28), 27.3 (q, C-29), 18.2 (q, C-30), 104.2 (d, Glc-1), 75.7 (d, Glc-2), 78.9 (d, Glc-3), 71.8 (d. Glc-4), 78.3 (d, Glc-5), 63.0 (d, Glc-6); ESIMS m/z 657 [M + Na]$^+$, 673 [M + K]$^+$; ESIMS m/z 633 [M − H]$^-$. |

TABLE 1-continued

| Compound | Chemical structure | Spectral data |
|---|---|---|
| Compound 13 | 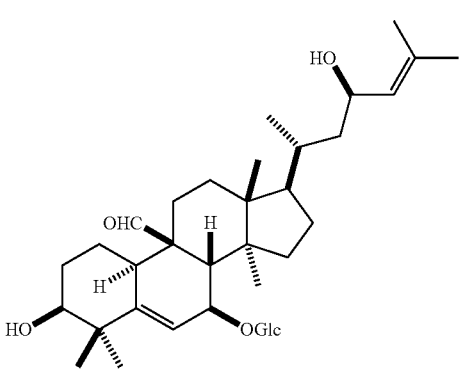<br>Molecular weight 635<br>Momordicin IV | Molecular formula $C_{36}H_{58}O_9$; amorphous white powder; optical activity $[\alpha]^{22}_D$ +90.0 (c = 0.1, MeOH); $^1$H-NMR ($C_5D_5N$, 500 MHz) $\delta_H$ 0.75, 0.89, 1.12, 1.43 (each 3H, s), 1.35, 1.55, 1.93 (each 2H), 1.16, 1.50, 1.53, 1.55, 1.90, 1.94, 1.96, 2.65 (each 1H), 3.81 (1H, br s, H-3), 6.16 (1H, d, J = 4.1 Hz, H-6), 4.62 (1H, d, J = 4.1 Hz, H-7), 2.53 (1H, s, H-8), 2.69 (1H, m, H-10), 10.56 (1H, s, H-19), 2.05 (1H, m, H-20), 1.10 (3H, d, J = 6.6 Hz, H-21), 4.78 (1H, dt, $J_1$ = 8.1 Hz, $J_2$ = 1.9 Hz, H-23), 5.60 (1H, d, J = 8.4 Hz, H-24), 1.68 (3H, s, H-26), 1.70 (3H, s, H-27), 4.95 (1H, d, J = 8.0 Hz, Glc-1), 4.02 (1H, br t, Glc-2), 4.27 (1H, d, Glc-3), 4.22 (1H, d, Glc-4), 3.88 (1H, br s, Glc-5), 4.41 (1H, dd, $J_1$ = 12.4 Hz, $J_2$ = 5.6 Hz. Glc-6a), 4.61 (1H, dd, $J_1$ = 12.4 Hz, $J_2$ = 1.2 Hz, Glc-6b); $^{13}$C-NMR ($C_5D_5N$, 125 MHz) $\delta_C$ 21.4 (t, C-1), 29.3 (t, C-2), 75.4 (d, C-3), 41.7 (s, C-4), 147.2 (s, C-5), 122.0 (d, C-6), 71.3 (d, C-7), 44.3 (d, C-8), 51.1 (s, C-9), 36.1 (d, C-10), 22.1 (t, C-11), 28.9 (t, C-12), 45.6 (s, C-13), 48.0 (s, C-14), 34.2 (t, C-15), 27.4 (t, C-16), 50.7 (d, C-17), 14.4 (q, C-18), 206.9 (d, C-19), 32.4 (d, C-20), 18.7 (q, C-21), 44.9 (t, C-22), 64.9 (d, C-23), 131.5 (d, C-24), 130.5 (s, C-25), 17.6 (q, C-26), 25.7 (q, C-27), 25.3 (q, C-28), 26.8 (q, C-29), 17.6 (q, C-30), 101.4 (d, Glc-1), 74.7 (d, Glc-2), 78.6 (d, Glc-3), 71.5 (d, Glc-4), 78.5 (d, Glc-5), 62.7 (d, Glc-6); ESIMS m/z 657 [M + Na]$^+$, 673 [M + K]$^+$; ESIMS m/z 633 [M − H]$^−$. |
| Compound 14 | 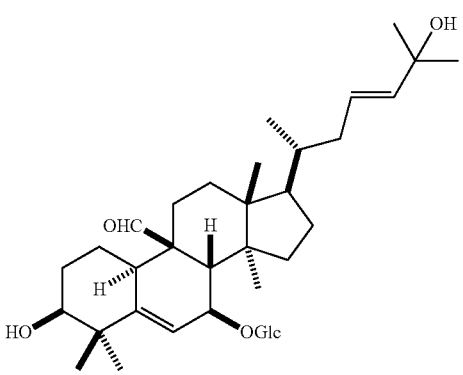<br>Molecular weight 635<br>Momordicin L | Molecular formula $C_{36}H_{58}O_9$; amorphous white powder; $^1$H-NMR ($C_5D_5N$, 500 MHz) $\delta_H$ 3.78 (1H, br s, H-3), 6.15 (1H, d, J = 4.7 Hz, H-6), 4.28 (1H, d, J = 5.3 Hz, H-7), 2.52 (1H, br s, H-8), 0.70 (3H, s, H-18), 10.49 (1H, s, H-19), 0.93 (3H, d, J = 5.8 Hz, H-21), 5.92 (2H, m, H-23), 5.92 (2H, m, H-24), 1.53 (3H, s, H-26), 1.53 (3H, s, H-27), 1.42 (3H, s, H-28), 1.11 (3H, s, H-29), 0.82 (3H, s, H-30), 4.95 (1H, d, J = 8.0 Hz, Glc-1), 4.02 (1H, br t, Glc-2), 4.27 (1H, d, Glc-3), 4.22 (1H, d, Glc-4), 3.88 (1H, br s, Glc-5), 4.41 (1H, dd, $J_1$ = 12.4 Hz, $J_2$ = 5.6 Hz, Glc-6a), 4.61 (1H, dd, $J_1$ = 12.4 Hz, $J_2$ = 1.2 Hz, Glc-6b); $^{13}$C-NMR ($C_5D_5N$, 125 MHz) $\delta_C$ 21.9 (t, C-1), 29.8 (t, C-2), 75.0 (d, C-3), 41.9 (s, C-4), 147.6 (s, C-5), 135.1 (d, C-6), 71.7 (d, C-7), 40.1 (d, C-8), 50.4 (s, C-9), 36.7 (d, C-10), 22.6 (t, C-11), 29.3 (t, C-12), 45.7 (s, C-13), 48.1 (s, C-14), 34.9 (t, C-15), 27.4 (t, C-16), 50.2 (d, C-17), 15.0 (q, C-18), 207.4 (d, C-19), 36.6 (d, C-20), 19.0 (q, C-21), 39.5 (t, C-22), 122.3 (d, C-23), 141.7 (d, C-24), 69.7 (s, C-25), 30.8 (q, C-26), 30.0 (q, C-27), 26.2 (q, C-28), 27.4 (q, C-29), 18.2 (q, C-30), 101.7 (d, Glc-1), 75.5 (d, Glc-2), 78.7 (d, Glc-3), 71.8 (d, Glc-4), 78.8 (d, Glc-5), 63.0 (d, Glc-6); ESITOFCMS m/z 657.2946 [M + Na]$^+$; 673.2549 [M + K]$^+$. |

TABLE 1-continued

| Compound | Chemical structure | Spectral data |
|---|---|---|
| Compound 15 | 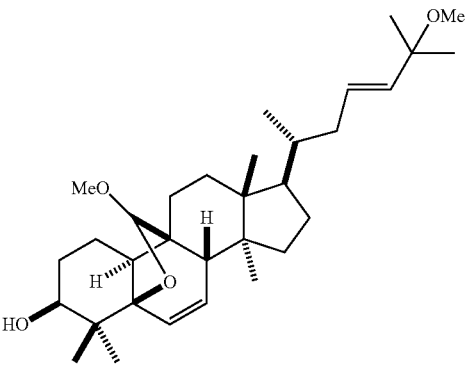<br>Molecular weight 500<br>5β,19R-epoxy-19,25-dimethoxycucurbita-6,23-dien-3β-ol | Molecular formula $C_{32}H_{52}O_4$; amorphous white powder; $^1$H-NMR (CDCl$_3$, 300 MHz) $\delta_H$ 1.50 (2H, m, H-1), 1.80 (2H, m, H-2), 3.43 (1H, br s, H-3), 5.63 (1H, dd, $J_1$ = 3.0 Hz, $J_2$ = 9.3 Hz, H-6), 5.96 (1H, dd, $J_1$ = 3.3 Hz, $J_2$ = 9.3 Hz, H-7), 2.89 (1H, br s, H-8), 2.40 (1H, m, H-10), 1.74 (1H, m H-11), 1.61 (1H, m H-11), 1.61 (2H, m, H-12), 1.31 (2H, m, H-15), 1.92 (2H, m, H-16), 1.40 (1H, m, H-17), 0.88 (3H, s, H-18), 4.65 (1H, s, H-19), 5.45 (1H, m, H-23), 5.40 (1H, d, H-24), 1.23 (3H, s, H-26), 1.23 (3H, s, H-27), 3.37 (3H, s, 19-OMe), 3.13 (3H, s, 25-OMe); $^{13}$C-NMR (CDCl$_3$, 75 MHz) $\delta_C$ 17.4 (t, C-1), 27.2 (t, C-2), 76.5 (d, C-3), 37.3 (s, C-4), 86.8 (s, C-5), 132.8 (d, C-6), 130.9 (d, C-7), 41.6 (d, C-8), 48.3 (s, C-9), 40.5 (d, C-10), 23.2 (t, C-11), 30.7 (t, C-12), 45.1 (s, C-13), 48.0 (s, C-14), 33.4 (t, C-15), 28.0 (t, C-16), 51.0 (d, C-17), 14.7 (q, C-18), 112.1 (d, C-19), 37.9 (d, C-20), 18.7 (q, C-21), 27.1 (t, C-22), 128.4 (d, C-23), 136.8 (d, C-24), 74.9 (s, C-25), 26.1 (q, C-26), 25.8 (q, C-27), 20.6 (3q, C-28), 24.4 (q, C-29), 19.9 (q, C-30), 57.3 (q, 19-OMe), 50.3 (q, 25-OMe); HRMS m/z 500.3874 [M]$^+$ (calcd for $C_{32}H_{52}O_4$, 500.3865). |
| Compound 16 | 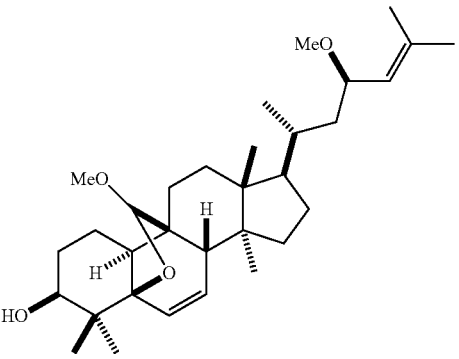<br>Molecular weight 500<br>5β,19R-epoxy-19,23 dimethoxycucurbita-6,24-dien-3β-ol | Molecular formula $C_{32}H_{52}O_4$; amorphous white powder; optical activity $[\alpha]^{20}_D$ −74 (c = 0.2, cyclohexane); UV (cyclohexane) $\lambda_{max}$ (log ε) 210.4 (3.20) nm; IR (KBr) $\nu_{max}$ 3471, 2926, 2882, 1732, 1647, 1469, 1383, 1115, 1084 cm$^{-1}$; $^1$H-NMR (CDCl$_3$, 300 MHz) $\delta_H$ 1.50 (2H, m, H-1), 1.80 (2H, m, H-2), 3.43 (1H, br s, H-3), 5.63 (1H, dd, $J_1$ = 3.0 Hz, $J_2$ = 9.3 Hz, H-6), 5.96 (1H, dd, $J_1$ = 3.3 Hz, $J_2$ = 9.3 Hz, H-7), 2.89 (1H, br s, H-8), 2.40 (1H, m, H-10), 1.74 (1H, m H-11), 1.61 (1H, m H-11), 1.61 (2H, m, H-12), 1.31 (2H, m, H-15), 1.92 (2H, m, H-16), 1.40 (1H, m, H-17), 0.88 (3H, s, H-18), 4.65 (1H, s, H-19), 1.73 (1H, m, H-20), 0.96 (3H, d, J = 6.6 Hz, H-21), 1.69 (1H, m, H-22), 1.00 (1H, m, H-22), 3.95 (1H, dt, $J_1$ = 3.0 Hz, $J_2$ = 9.3 Hz, H-23), 5.02 (1H, br d, J = 8.4 Hz, H-24), 1.74 (3H, s, H-26), 1.68 (3H, s, H-27), 0.85 (3H, s, H-28), 1.22 (3H, s, H-29), 0.85 (3H, s, H-30), 3.43 (3H, s, 19-OMe), 3.21 (3H, s, 23-OMe); $^{13}$C-NMR (CDCl$_3$, 75 MHz) $\delta_C$ 17.4 (t, C-1), 27.2 (t, C-2), 76.5 (d, C-3), 37.3 (s, C-4), 86.8 (s, C-5), 132.8 (d, C-6), 130.9 (d, C-7), 41.6 (d, C-8), 48.3 (s, C-9), 40.5 (d, C-10), 23.2 (t, C-11), 30.7 (t, C-12), 45.1 (s, C-13), 48.0 (s, C-14), 33.4 (t, C-15), 28.0 (t, C-16), 51.0 (d, C-17), 14.7 (q, C-18), 112.1 (d, C-19), 32.5 (d, C-20), 18.7 (q, C-21), 42.8 (t, C-22), 74.7 (d, C-23), 128.0 (d, C-24), 134.5 (s, C-25), 25.8 (q, C-26), 18.1 (q, C-27), 24.1 (3q, C-28), 20.5 (q, C-29), 19.8 (q, C-30), 58.2 (q, 19-OMe), 55.6 (q, 23-OMe); HRESIMS m/z 523.3752 [M + Na]$^+$ (calcd for $C_{32}H_{52}O_4Na$, 523.3758). |

TABLE 1-continued

| Compound | Chemical structure | Spectral data |
|---|---|---|
| Compound 17 | 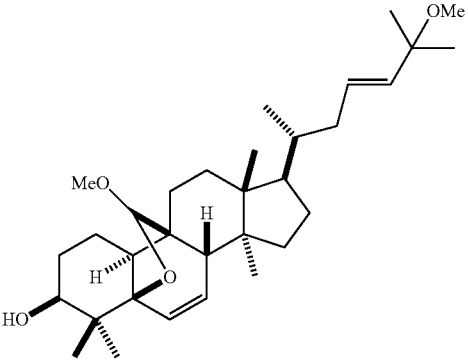<br>Molecular weight 500<br>5β,19S-epoxy-19,25-dimethoxycucurbita-6,23-dien-3β-ol | Molecular formula $C_{32}H_{52}O_4$; amorphous white powder; optical activity $[\alpha]_D$ −37.1 (c = 0.054, CHCl$_3$); IR (KBr) $\nu_{max}$ 3516, 2926, 1377, 1109, 1070 cm$^{-1}$; $^1$H-NMR (CDCl$_3$, 300 MHz) δ$_H$ 0.90, 0.88, 0.87, 0.86, 0.83 (each 3H), 3.48 (1H, m, H-3), 6.07 (1H, dd, J$_1$ = 9.8 Hz, J$_2$ = 2.3 Hz, H-6), 5.50 (1H, m, H-7), 2.24 (1H, m, H-8), 2.15 (1H, m, H-10), 4.40 (1H, s, H-19), 5.45 (1H, m, H-23), 5.40 (1H, d, H-24), 1.23 (3H, s, H-26), 1.23 (3H, s, H-27), 3.37 (3H, s, 19-OMe), 3.13 (3H, s, 25-OMe); $^{13}$C-NMR (CDCl$_3$, 75 MHz) δ$_C$ 16.5 (t, C-1), 21.4 (t, C-2), 76.2 (d, C-3), 45.1 (s, C-4), 85.1 (s, C-5), 133.5 (d, C-6), 130.5 (d, C-7), 49.8 (d, C-8), 48.9 (s, C-9), 36.1 (d, C-10), 30.4 (t, C-11), 39.4 (t, C-12), 37.1 (s, C-13), 48.0 (s, C-14), 33.5 (t, C-15), 27.8 (t, C-16), 50.0 (d, C-17), 15.0 (q, C-18), 114.7 (d, C-19), 37.9 (d, C-20), 18.7 (q, C-21), 27.1 (t, C-22), 128.4 (d, C-23), 136.8 (d, C-24), 74.9 (s, C-25), 26.1 (q, C-26), 25.8 (q, C-27), 20.6 (3q, C-28), 24.4 (q, C-29), 19.9 (q, C-30), 57.3 (q, 19-OMe), 50.3 (q, 25-OMe); HRMS m/z 500.3874 [M]$^+$ (calcd for $C_{32}H_{32}O_4$, 500.3865). |
| Compound 18 | 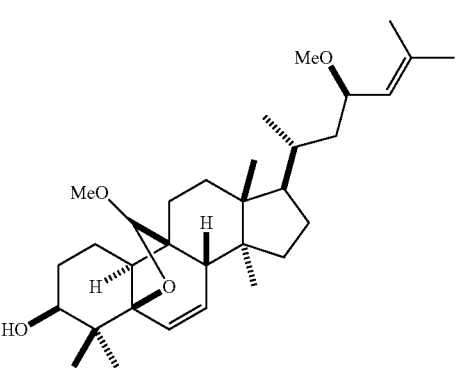<br>Molecular weight 500<br>5β,19S-epoxy-19,23-dimethoxycucurbita-6,24-dien-3β-ol | Molecular formula $C_{32}H_{52}O_4$; amorphous white powder; optical activity $[\alpha]^{20}_D$ −26.5 (c = 0.2, cyclohexane); UV (cyclohexane) $\lambda_{max}$ (log ε) 210.8 (3.20) nm; IR (KBr) $\nu_{max}$ 3525, 2939, 2875, 1732, 1647, 1466, 1382, 1113, 1083 cm$^{-1}$; $^1$H-NMR (CDCl$_3$, 300 MHz) δ$_H$ 1.35 (1H, m, H-1), 2.03 (1H, m, H-l), 1.74 (2H, m, H-2), 3.44 (1H, br s, H-3), 6.08 (1H, dd, J$_1$ = 1.5 Hz, J$_2$ = 9.6 Hz, H-6), 5.51 (1H, dd, J$_1$ = 3.6 Hz, J$_2$ = 9.9 Hz, H-7), 2.26 (1H, br s, H-8), 2.31 (1H, dd, J$_1$ = 6 Hz, J$_2$ = 12 Hz, H-10), 1.74 (1H, m, H-11), 1.65 (1H, m, H-11), 1.63 (2H, m, H-12), 1.29 (2H, m, H-15), 1.93 (2H, m, H-16), 1.40 (1H, m, H-17), 0.88 (3H, s, H-18), 4.42 (1H, s, H-19), 1.74 (1H, m, H-20), 0.94 (3H, d, J = 6.3 Hz, H-21), 1.70 (1H, m, H-22), 1.00 (1H, m, H-22), 3.94 (1H, dt, J$_1$ = 3.0 Hz, J$_2$ = 9.3 Hz, H-23), 5.02 (1H, br d, J = 8.7 Hz, H-24), 1.74 (3H, s, H-26), 1.68 (3H, s, H-27), 0.88 (3H, s, H-28), 1.25 (3H, s, H-29), 0.85 (3H, s, H-30), 3.40 (3H, s, 19-OMe), 3.21 (3H, s. 23-OMe); $^{13}$C-NMR (CDCl$_3$, 75 MHz) δ$_C$ 16.5 (t, C-1), 27.4 (t, C-2), 76.2 (d, C-3), 37.1 (s, C-4), 85.0 (s, C-5), 133.0 (d, C-6), 130.5 (d, C-7), 49.8 (d, C-8), 49.0 (s, C-9), 37.9 (d, C-10), 21.4 (t, C-11), 30.6 (t, C-12), 45.2 (s, C-13), 48.1 (s, C-14), 33.4 (t, C-15), 27.9 (t, C-16), 51.0 (d, C-17), 15.0 (q, C-18), 114.7 (d, C-19), 32.5 (d, C-20), 18.7 (q, C-21), 42.8 (t, C-22), 74.6 (d, C-23), 127.0 (d, C-24), 134.0 (s, C-25), 25.8 (q, C-26), 18.1 (q, C-27), 24.4 (3q, C-28), 20.6 (q, C-29), 19.9 (q, C-30), 57.2 (q, 19-OMe), 55.7 (q, 25-OMe) HRESIMS m/z 523.3750 [M + Na]$^+$ (calcd for $C_{32}H_{52}O_4$Na, 523.3758). |
| Compound 19 | 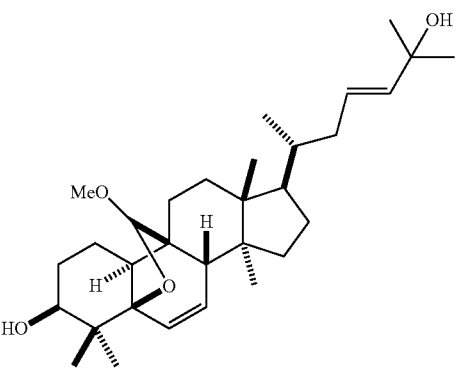<br>Molecular weight 486<br>5β,19R-epoxy-19-methoxycucurbita-6,23-diene-3β,25–diol | Molecular formula $C_{31}H_{50}O_4$; amorphous white powder; $^1$H-NMR (CDCl$_3$, 300 MHz) δ$_H$ 1.50 (2H, m, H-1), 1.80 (2H, m, H-2), 3.43 (1H, br s, H-3), 5.63 (1H, dd, J$_1$ = 3.0 Hz, J$_2$ = 9.3 Hz, H-6), 5.96 (1H, dd, J$_1$ = 3.3 Hz, J$_2$ = 9.3 Hz, H-7), 2.89 (1H, br s, H-8), 2.40 (1H, m, H-10), 1.74 (1H, m, H-11), 1.61 (1H, m, H-11), 1.61 (2H, m, H-12), 1.31 (2H, m, H-15), 1.92 (2H, m, H-16), 1.40 (1H, m, H-17), 0.88 (3H, s, H-18), 4.65 (1H, s, H-19), 1.23 (3H, d, H-21), 5.57 (2H, m, H-24), 5.57 (2H, m, H-24), 1.29 (3H, s, H-26), 1.29 (3H, s, H-27), 3.37 (3H, s, 19-OMe); $^{13}$C-NMR (CDCl$_3$, 75 MHz) δ$_C$ 17.4 (t, C-1), 27.2 (t, C-2), 76.5 (d, C-3), 37.3 (s, C-4), 86.8 (s, C-5), 132.8 (d, C-6), 130.9 (d, C-7), 41.6 (d, C-8), 48.3 (s, C-9), 40.5 (d, C-10), 23.2 (t, C-11), 30.7 (t, C-12), 45.1 (s, C-13), 48.0 (s, C-14), 33.4 (t, C-15), 28.0 (t, C-16), 51.0 (d, C-17), 14.7 (q, C-18), 112.1 (d, C-19), 36.2 (d, C-20), 18.6 (q, C-21), 27.1 (t, C-22), 125.3 (d, C-23), 139.5 (d, C-24), 70.5 (s, C-25), 29.9 (2q, C-26, 27), 30.0, 20.6 (q, C-28), 24.4 (q, C-29), 20.5 (q, C-30), 57.3 (q, 19-OMe) |

| Compound | Chemical structure | Spectral data |
|---|---|---|
| Compound 20 | 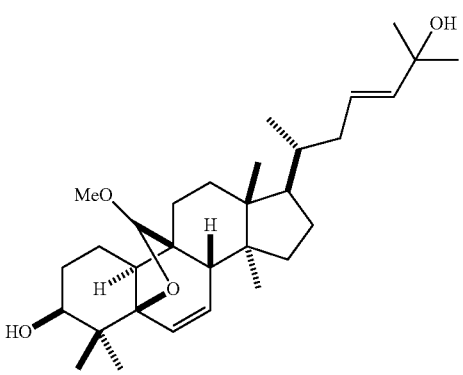<br>Molecular weight 486<br>5β,19S-epoxy-19-methoxycucurbita-6,23-diene-3β,25–diol | Molecular formula $C_{31}H_{50}O_4$; amorphous white powder; melt point 102-104° C.; optical activity $[\alpha]_D$ −52.8 (c = 0.036, $CHCl_3$); $^1$H-NMR ($CDCl_3$, 300 MHz) $\delta_H$ 0.88, 0.86, 0.83, 0.84 (each 3H, s, 4 × $CH_3$), 3.41 (1H, br s, J = 6.7 Hz, H-3), 6.10 (1H, dd, $J_1$ = 9.71 Hz, $J_2$ = 2.30 Hz, H-6), 5.50 (1H, dd, $J_1$ = 9.71 Hz, $J_2$ = 3.72 Hz, H-7), 2.13 (1H, br s, H-8), 2.29 (1H, m, H-10), 4.40 (1H, s, H-19), 1.23 (3H, d, H-21), 5.57 (1H, m, H-23), 5.57 (1H, m, H-24), 1.29 (3H, s, H-26), 1.29 (3H, s, H-27), 3.37 (3H, s, 19-OMe); $^{13}$C-NMR ($CDCl_3$, 75 MHz) $\delta_C$ 16.5 (t, C-1), 21.4 (t, C-2), 76.2 (d, C-3), 45.1 (s, C-4), 85.1 (s, C-5), 133.0 (d, C-6), 130.5 (d, C-7), 49.8 (d, C-8), 48.9 (s, C-9), 37.9 (d, C-10), 30.4 (t, C-11), 39.1 (t, C-12), 37.1 (s, C-13), 47.9 (s, C-14), 33.5 (t, C-15), 27.8 (t, C-16), 50.1 (d, C-17), 15.0 (q, C-18), 114.7 (d, C-19), 36.2 (d, C-20), 18.6 (q, C-21), 27.1 (t, C-22), 125.3 (d, C-23), 139.5 (d, C-24), 70.7 (s, C-25), 29.9 (q, C-26), 30.0 (q, C-27), 20.6 (q, C-28), 24.4 (q, C-29), 20.5 (q, C-30), 57.3 (q, 19-OMe); HRMS m/z 486.3725 $[M]^+$ (calcd for $C_{31}H_{50}O_4$, 486.3709). |
| Compound 21 | 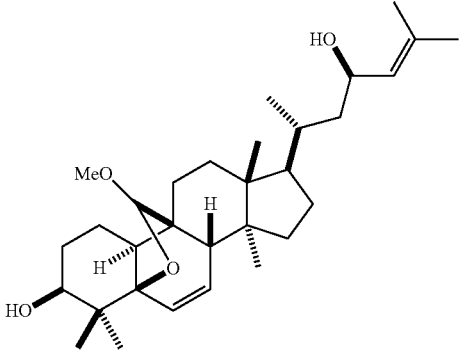<br>Molecular weight 486<br>5β,19S-epoxy-19-methoxycucurbita-6,24-dien-3β,23–diol | Molecular formula $C_{31}H_{50}O_4$; amorphous white powder; optical activity $[\alpha]^{19.8}_D$ −62 (c = 0.19, MeOH); UV (MeOH) $\lambda_{max}$ (log ε) 229 (4.03), 202 (4.36) nm; IR (KBr) $\nu_{max}$ 3444, 2950, 1639, 1383, 1081 $cm^{-1}$; $^1$H-NMR ($CDCl_3$, 600 MHz) $\delta_H$ 1.36 (1H, m, H-1), 1.95 (1H, m, H-1), 1.71 (1H, m, H-2), 1.75 (1H, m, H-2), 3.41 (1H, d, J = 9.2 Hz, H-3), 6.09 (1H, dd, $J_1$ = 1.6 Hz, $J_2$ = 9.7 Hz, H-6), 5.51 (1H, dd, $J_1$ = 3.5 Hz, $J_2$ = 9.7 Hz, H-7), 2.26 (1H, m, H-8), 2.28 (1H, m, H-10), 1.61 (1H, m, H-11), 1.72 (1H, m, H-11), 1.63 (1H, m, H-12), 2.17 (1H, s, H-12), 1.31 (2H, m, H-15), 1.39 (1H, m, H-16), 1.95 (1H, m, H-16), 1.44 (1H, m, H-17), 0.90 (3H, s, H-18), 4.41 (1H, s, H-19), 1.70 (1H, s, H-20), 0.98 (3H, d, J = 6.4 Hz, H-21), 1.03 (1H, m, H-22), 1.64 (1H, m, H-22), 4.46 (1H, m, H-23), 5.19 (1H, d, J = 8.4 Hz, H-24), 1.68 (3H, s, H-26), 1.70 (3H, s, H-27), 0.88 (3H, s, H-28), 1.24 (3H, s, H-29), 0.8 (3H, s, H-30), 3.39 (3H, s, 19-OMe); $^{13}$C-NMR ($CDCl_3$, 150 MHz) $\delta_C$ 16.5 (t, C-1), 27.1 (t, C-2), 76.2 (d, C-3), 37.1 (s, C-4), 85.1 (s, C-5), 133.0 (d, C-6), 130.5 (d, C-7), 49.8 (d, C-8), 49.0 (s, C-9), 37.9 (d, C-10), 21.4 (t, C-11), 30.5 (t, C-12), 45.2 (s, C-13), 48.1 (s, C-14), 33.4 (t, C-15), 28.1 (t, C-16), 50.9 (d, C-17), 15.0 (q, C-18), 114.7 (d, C-19), 32.6 (d, C-20), 18.6 (q, C-21), 44.4 (t, C-22), 65.9 (d, C-23), 128.9 (d, C-24), 133.9 (s, C-25), 18.1 (q, C-26), 25.7 (q, C-27), 24.4 (3q, C-28), 20.6 (q, C-29), 19.9 (q, C-30), 57.3 (q, 19-OMe); ESIMS m/z 509 $[M + Na]^+$; HRESIMS m/z 509.3611 $[M + Na]^+$ (calcd for $C_{31}H_{50}O_4Na$ 509.3601). |

| Compound | Chemical structure | Spectral data |
|---|---|---|
| Compound 22 | 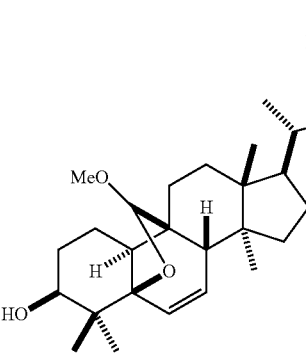<br>Molecular weight 486<br>5β,19R-epoxy-19-methoxycucurbita-6,24-dien-3β,23-diol | Molecular formula $C_{31}H_{50}O_4$; amorphous white powder; optical activity $[\alpha]^{19.9}_D$ −102 (c = 0.08, MeOH); UV (MeOH) $\lambda_{max}$ (log ε) 228 (4.69), 202 (4.54) nm; IR (KBr) $\nu_{max}$ 3441, 2946, 1635, 1449, 1184, 1115, 1083 cm$^{-1}$; $^1$H-NMR (CDCl$_3$, 600 MHz) $\delta_H$ 1.49 (1H, m, H-1), 1.77 (1H, m, H-1), 1.75 (1H, m, H-2), 1.78 (1H, m, H-2), 3.41 (1H, d, J = 9.2 Hz, H-3), 5.99 (1H, d, J = 9.8 Hz, H-6), 5.62 (1H, dd, J$_1$ = 3.5 Hz, J$_2$ = 9.7 Hz, H-7), 2.89 (1H, br s, H-8), 2.40 (1H, m, H-10), 1.62 (1H, m, H-11), 1.75 (1H, m, H-11), 1.62 (1H, m, H-12), 2.17 (1H, s, H-12), 1.31 (1H, m, H-15), 1.36 (1H, m, H-15), 1.38 (1H, m, H-16), 1.95 (1H, m, H-16), 1.42 (1H, m, H-17), 0.89 (3H, s, H-18), 4.65 (1H, s, H-19), 1.70 (1H, s, H-20), 0.99 (3H, d, J = 6.4 Hz, H-21), 1.03 (1H, m, H-22), 1.64 (1H, m, H-22), 4.47 (1H, m, H-23), 5.20 (1H, d, J = 8.4 Hz, H-24), 1.69 (3H, s, H-26), 1.70 (3H, s, H-27), 0.84 (3H, s, H-28), 1.21 (3H, s, H-29), 0.84 (3H, s, H-30), 3.43 (3H, s, 19-OMe); $^{13}$C-NMR (CDCl$_3$, 150 MHz) $\delta_C$ 17.4 (t, C-1), 27.2 (t, C-2), 76.2 (d, C-3), 37.3 (s, C-4), 86.7 (s, C-5), 130.9 (d, C-6), 132.7 (d, C-7), 41.6 (d, C-8), 48.3 (s, C-9), 40.5 (d, C-10), 23.2 (t, C-11), 30.7 (t, C-12), 45.1 (s, C-13), 48.0 (s, C-14), 33.4 (t, C-15), 28.2 (t, C-16), 50.9 (d, C-17), 14.7 (q, C-18), 112.1 (d, C-19), 32.6 (d, C-20), 18.6 (q, C-21), 44.4 (t, C-22), 65.9 (d, C-23), 129.0 (d, C-24), 133.8 (s, C-25), 18.1 (q, C-26), 25.7 (q, C-27), 24.1 (q, C-28), 20.5 (q, C-29), 19.7 (q, C-30), 58.2 (q, 19-OMe); ESIMS m/z 509 [M + Na]$^+$; HRESIMS m/z 509.3609 [M + Na]$^+$ (calcd for $C_{31}H_{50}O_4Na$, 509.3601). |
| Compound 23 | 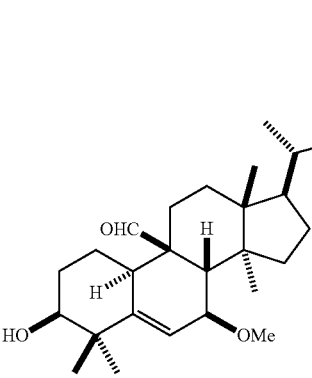<br>Molecular weight 500<br>3β,hydroxy-7β,25-dimethoxycucurbita-5,23E-dien-19-al | Molecular formula $C_{32}H_{52}O_4$; amorphous white powder; melt point 104-107° C.; optical activity $[\alpha]^{25}_D$ +25.9 (c = 0.26, CHCl$_3$); IR (KBr) $\nu_{max}$ 3444, 2929, 1712, 845, 820 cm$^{-1}$; $^1$H-NMR (C$_5$D$_5$N, 600 MHz) $\delta_H$ 1.69 (1H, m, H-1), 2.01 (1H, m, H-1), 1.90 (1H, m, H-2), 2.05 (1H, m, H-2), 3.81 (1H, br s, H-3), 6.15 (1H, d, J = 5.4 Hz, H-6), 3.55 (1H, br d, J = 5.4 Hz, H-7), 2.23 (1H, s, H-8), 2.65 (1H, m, H-10), 1.54 (1H, m, H-11a), 1.95 (1H, m, H-11β), 1.60 (2H, s, H-12), 1.35 (2H, m, H-15), 1.36 (1H, m, H-16α), 1.95 (1H, m, H-16β), 1.56 (1H, m, H-17), 0.95 (3H, s, H-18), 10.31 (1H, s, H-19), 1.55 (1H, s, H-20), 1.00 (3H, d, J = 5.9 Hz, H-21), 1.85 (1H, m, H-22), 2.24 (1H, m, H-22), 5.66 (1H, ddd, J$_1$ = 5.4 Hz, J$_2$ = 8.3 Hz, J$_3$ = 15.8 Hz, H-23), 5.57 (1H, d, J = 15.8 Hz, H-24), 1.34 (3H, s, H-26), 1.34 (3H, s, H-27), 1.1 (3H, s, H-28), 1.50 (3H, s, H-29), 0.81 (3H, s, H-30), 3.29 (3H, s, 19-OMe), 3.23 (3H, s, 25-OMe); $^{13}$C-NMR (C$_5$D$_5$N, 150 MHz) $\delta_C$ 21.6 (t, C-1), 29.8 (t, C-2), 75.6 (d, C-3), 42.0 (s, C-4), 147.7 (s, C-5), 121.1 (d, C-6), 75.7 (d, C-7), 45.8 (d, C-8). 50.3 (s, C-9), 36.8 (d, C-10), 22.6 (t, C-11), 29.4 (t, C-12), 45.9 (s, C-13), 47.9 (s, C-14), 35.1 (t, C-15), 27.7 (t, C-16), 50.3 (d, C-17), 15.0 (q, C-18), 207.2 (d, C-19), 36.4 (d, C-20), 19.0 (q, C-21), 39.7 (t, C-22), 128.4 (d, C-23), 137.8 (d, C-24), 74.9 (s, C-25), 26.1 (q, C-26), 26.5 (q, C-27), 27.3 (q, C-28), 26.2 (q, C-29), 18.2 (q, C-30), 55.9 (q, 19-OMe), 50.2 (q, 25-OMe); EIMS m/z 482 [M − H$_2$O]$^+$; 440 [M − H$_2$O − MeOH]$^+$; HREIMS m/z 482.3759 [M − H$_2$O]$^+$ (calcd for $C_{32}H_{50}O_3$, 482.3760) ; FABMS m/z 539 [M + K]$^+$. |

Example 1-23

For the obtained compounds 1 to 23, cancer cell viability tests were performed by the above-described <Cancer cell viability tests>. The results are shown in FIGS. 4 to 26.

In addition, inhibitory concentrations of cell growth activity IC50 (μM) (i.e., minimum concentration of the compound required for 50% inhibition of cell growth activity) for the compounds 1 to 23 were calculated according to the cancer cell viability tests shown in FIGS. 4 to 26. By conversion of the results, inhibitory concentrations of cell growth activity (IC50) of compounds 1 to 23 are shown in Table 2 below, respectively.

TABLE 2

| Cell line | Example 1 Compound 1 | Example 2 Compound 2 | Example 3 Compound 3 | Example 4 Compound 4 | Example 5 Compound 5 | Example 6 Compound 6 | Example 7 Compound 7 | Example 8 Compound 8 |
|---|---|---|---|---|---|---|---|---|
| Vero | ** | 12.8 | ** | 35.3 | 25.26 | 23.08 | 23.19 | 24.15 |
| MDA-MB-231 | ** | 4.44 | 5.2 | 12.08 | 8.07 | 23.51 | 6.0 | 5.19 |
| U87-MG | 150.5 | 7.52 | 6.82 | 14.37 | 8.8 | 23.42 | 8.51 | 7.54 |
| MDA-MB-468 | ** | 7.25 | 10.41 | 18.6 | 16.76 | 13.95 | 13.94 | 9.81 |
| Mahlavu | ** | 11.27 | 23 | 29.42 | 18.52 | 16.23 | 11.94 | 11.5 |
| A549 | ** | 4.16 | 12.18 | 12.9 | 11.99 | 5.43 | 6.26 | 4.86 |
| SW480 | ** | 13.06 | 18.22 | 12.95 | 16.37 | 14.91 | 13.49 | 13.8 |
| U937 | 36.63 | 0.05 | 3.45 | 8.08 | 3.67 | 1.57 | 5.52 | 5.39 |

| Cell line | Example 9 Compound 9 | Example 10 Compound 10 | Example 11 Compound 11 | Example 12 Compound 12 | Example 13 Compound 13 | Example 14 Compound 14 | Example 15 Compound 15 | Example 16 Compound 16 |
|---|---|---|---|---|---|---|---|---|
| Vero | 25.88 | 19.19 | ** | 124.42 | ** | ** | ** | ** |
| MDA-MB-231 | 18.33 | 10.66 | ** | 41.71 | 59.42 | 32.81 | ** | ** |
| U87-MG | 15.55 | 10.68 | ** | 49.03 | 102.96 | 58.47 | ** | ** |
| MDA-MB-468 | 26.77 | 20.33 | ** | 56.52 | 58.34 | 39.26 | ** | ** |
| Mahlavu | 5.07 | 19.37 | ** | 70.31 | ** | ** | ** | ** |
| A549 | 24.41 | 9.81 | ** | 100.38 | 198.3 | 171.06 | ** | ** |
| SW480 | 31.82 | 17.87 | ** | 98.6 | 67.15 | 64.24 | ** | ** |
| U937 | 11.15 | 5.92 | 84.21 | 58.6 | 32.52 | 19.8 | 4.28 | 97.9 |

| Cell line | Example 17 Compound 17 | Example 18 Compound 18 | Example 19 Compound 19 | Example 20 Compound 20 | Example 21 Compound 21 | Example 22 Compound 22 | Example 23 Compound 23 |
|---|---|---|---|---|---|---|---|
| Vero | ** | ** | 36.14 | 12.5 | ** | ** | 15.88 |
| MDA-MB-231 | ** | ** | 22.6 | 10.44 | 130 | ** | 7.91 |
| U87-MG | ** | ** | 25 | 12.16 | 83.46 | ** | 7.65 |
| MDA-MB-468 | 9.4 | ** | 24.35 | 6.9 | 35.4 | ** | 7.55 |
| Mahlavu | ** | ** | 20.73 | 19.65 | ** | ** | 15.44 |
| A549 | ** | ** | 45.64 | 20.06 | ** | ** | 15.34 |
| SW480 | ** | ** | 16.61 | 12.6 | 117.8 | ** | 7.56 |
| U937 | 12.20 | ** | 11.88 | 4.33 | 6.19 | 6.17 | 5.75 |

** indicates that the inhibitory concentration of cell growth activity (IC50) of the compound is much greater than 256 μM, and has no inhibition effect.

Then, for the obtained compounds 1 to 23, the compounds were evaluated for their ability to inhibit cell growth activity according to the following evaluation criteria with reference to the data in Table 2 above.

That is, when the inhibitory concentration of cell growth activity (IC50) of the compound listed in Table 2 above is greater than 256 μM, the ability of the compound to inhibit cell growth activity is evaluated to be very poor (X X); when the inhibitory concentration of cell growth activity (IC50) is between 64 and 256 μM, the ability of the compound to inhibit cell growth activity is evaluated to be poor (X); when the inhibitory concentration of cell growth activity (IC50) is between 16 and 64 μM, the ability of the compound to inhibit cell growth activity is evaluated to be acceptable (Δ); when the inhibitory concentration of cell growth activity (IC50) is between 8 and 16 μM, the ability of the compound to inhibit cell growth activity is evaluated to be good (○); and when the inhibitory concentration of cell growth activity (IC50) is less than 8 μM, the ability of the compound to inhibit cell growth activity is evaluated to be excellent (◎). The individual evaluation results of these compounds are shown in Table 3 respectively.

TABLE 3

| Cell line | Example 1 Compound 1 | Example 2 Compound 2 | Example 3 Compound 3 | Example 4 Compound 4 | Example 5 Compound 5 | Example 6 Compound 6 | Example 7 Compound 7 | Example 8 Compound 8 |
|---|---|---|---|---|---|---|---|---|
| Vero | X X | ○ | X X | △ | △ | △ | △ | △ |
| MDA-MB-231 | X X | ◎ | ◎ | ○ | ○ | △ | ◎ | ◎ |
| U87-MG | X | ◎ | ◎ | ○ | ○ | △ | ○ | ◎ |
| MDA-MB-468 | X X | ◎ | ○ | △ | △ | ○ | ○ | ○ |
| Mahlavu | X X | ○ | △ | △ | △ | △ | ○ | ○ |
| A549 | X X | ◎ | ○ | ○ | ○ | ◎ | ◎ | ◎ |
| SW480 | X X | ○ | △ | ○ | △ | ○ | ○ | ○ |
| U937 | △ | ◎ | ◎ | ○ | ◎ | ◎ | ◎ | ◎ |

| Cell line | Example 9 Compound 9 | Example 10 Compound 10 | Example 11 Compound 11 | Example 12 Compound 12 | Example 13 Compound 13 | Example 14 Compound 14 | Example 15 Compound 15 | Example 16 Compound 16 |
|---|---|---|---|---|---|---|---|---|
| Vero | △ | △ | X X | X | X X | X X | X X | X X |
| MDA-MB-231 | △ | ○ | X X | △ | △ | △ | X X | X X |
| U87-MG | ○ | ○ | X X | △ | X | △ | X X | X X |
| MDA-MB-468 | △ | △ | X X | △ | △ | △ | X X | X X |
| Mahlavu | ◎ | △ | X X | X | X X | X X | X X | X X |
| A549 | △ | ○ | X X | X | X | X | X X | X X |
| SW480 | △ | △ | X X | X X | X | X | X X | X X |
| U937 | ○ | ◎ | X | △ | △ | △ | ◎ | X |

| Cell line | Example 17 Compound 17 | Example 18 Compound 18 | Example 19 Compound 19 | Example 20 Compound 20 | Example 21 Compound 21 | Example 22 Compound 22 | Example 23 Compound 23 |
|---|---|---|---|---|---|---|---|
| Vero | X X | X X | △ | ○ | X X | X X | ○ |
| MDA-MB-231 | X X | X X | △ | ○ | X | X X | ◎ |
| U87-MG | XX | XX | △ | ○ | X | X X | ◎ |
| MDA-MB-468 | ○ | X X | △ | ◎ | △ | X X | ◎ |
| Mahlavu | X X | X X | △ | △ | X X | X X | ○ |
| A549 | X X | X X | △ | △ | X X | X X | ○ |
| SW480 | X X | X X | △ | ○ | X | X X | ◎ |
| U937 | ○ | X X | ○ | ◎ | ◎ | ◎ | ◎ |

From the evaluation results of inhibitory ability of cell growth activity (IC50) listed in Table 3 above, it is clearly known that for inhibition of human Glioblastoma cells "U87-MG", compounds 4, 5, 7, 9, 10, and 20 have "good" (○) inhibitory ability of cell growth of human Glioblastoma cells, while compounds 2, 3, 8, and 23 have "excellent" (◎) inhibitory ability of cell growth of human Glioblastoma cells. In other words, momordicin and derivatives thereof obtained by the present invention are effective components for pharmaceutically resisting Glioblastoma or treating Glioblastoma.

For inhibition of human liver cancer cells "Mahlavu", compounds 2, 7, 8, and 23 have "good" (○) inhibitory ability of cell growth of human liver cancer cells, while compound 9 have "excellent" (◎) inhibitory ability of cell growth of human liver cancer cells. In other words, momordicin and derivatives thereof obtained by the present invention are effective components for pharmaceutically resisting liver cancer or treating liver cancer.

For inhibition of human colorectal cancer cells "SW-480", compounds 2, 4, 6, 7, 8, and 20 have "good" (○) inhibitory ability of cell growth of human colorectal cancer cells, while compound 23 have "excellent" (◎) inhibitory ability of cell growth of human colorectal cancer cells. In other words, momordicin and derivatives thereof obtained by the present invention are effective components for pharmaceutically resisting colorectal cancer or treating colorectal cancer.

For inhibition of human lung cancer cells "A549", compounds 3, 4, 5, 10, and 223 have "good" (○) inhibitory ability of cell growth of human lung cancer cells, while compounds 2, 6, 7, and 8 have "excellent" (◎) inhibitory ability of cell growth of human lung cancer cells. In other words, momordicin and derivatives thereof obtained by the present invention are effective components for pharmaceutically resisting lung cancer or treating lung cancer.

For inhibition of human lung cancer cells "A549", compounds 3, 4, 5, 10, and 23 have "good" (○) inhibitory ability of cell growth of human lung cancer cells, while compounds 2, 6, 7, and 8 have "excellent" (◎) inhibitory ability of cell growth of human lung cancer cells. In other words, momordicin and derivatives thereof obtained by the present invention are effective components for pharmaceutically resisting lung cancer or treating lung cancer.

For inhibition of human leukemia cells "U937", compounds 4, 9, 17, and 19 have "good" (○) inhibitory ability of cell growth of human leukemia cells, while compounds 2, 3, 5, 6, 7, 8, 10, 15, and 20 to 23 have "excellent" (◎) inhibitory ability of cell growth of human leukemia cells. In other words, momordicin and derivatives thereof obtained by the present invention are effective components for pharmaceutically resisting leukemia or treating leukemia.

For inhibition of human breast cancer cells "MDA-MB-231", compounds 4, 5, 10, and 20 have "good" (○) inhibitory ability of cell growth of human breast cancer cells, while compounds 2, 3, 7, 8, and 23 have "excellent" (◎) inhibitory ability of cell growth of human breast cancer cells; in addition, for inhibition of human breast cancer cells "MDA-MB-468", compounds 3, 6, 7, 8, and 17 have "good" (○) inhibitory ability of cell growth of human breast cancer cells, while compounds 2, 20, and 23 have "excellent" (●) inhibitory ability of cell growth of human breast cancer cells In other words, momordicin and derivatives thereof obtained by the present invention are effective components for pharmaceutically resisting breast cancer or treating breast cancer. From exemplification of examples 1 to 23 above, it can be clearly confirmed that for the pharmaceutical compounds for treating cancer of this invention, due to having chemical structures represented by formula (I) or (II) and having excellent inhibitory ability of cell growth activity for various human cancer cells, the compound of this invention is an active ingredient effective to treat cancer, and may be prepared into a pharmaceutical compound or pharmaceutical compound composition for treating cancer.

While specific examples of the invention have been disclosed in the forgoing detailed description of the invention, it is understood that these examples are not intended to limit the invention, and various variations and modifications can be made thereto by one of ordinary skill in the art to which this invention belongs, without departing the principle and spirit of this invention. Thus, the scope of this invention is defined by the appended claims.

The invention claimed is:

1. A compound represented by formula (I):

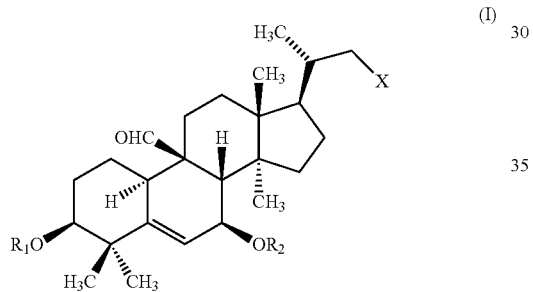

(I)

or a pharmaceutically acceptable salt thereof, wherein:

X represents:

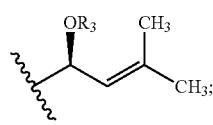

$R_1$ represents $C(O)CH_3$;
$R_2$ represents hydrogen, $C(O)H$ or $C(O)C_{2-10}$ alkyl; and
$R_3$ represents hydrogen, $C(O)H$ or $C(O)C_{1-10}$ alkyl; or
$R_1$ represents $C(O)CH_3$;
$R_2$ represents hydrogen, $C(O)H$ or $C(O)C_{1-10}$ alkyl; and
$R_3$ represents hydrogen, $C(O)H$ or $C(O)C_{2-10}$ alkyl; or
$R_1$ represents hydrogen, $C(O)H$ or $C(O)C_{2-10}$ alkyl;
$R_2$ represents $C(O)CH_3$; and
$R_3$ represents hydrogen, $C(O)H$ or $C(O)C_{1-10}$ alkyl; or
$R_1$ represents hydrogen, $C(O)H$ or $C(O)C_{1-10}$ alkyl;
$R_2$ represents $C(O)CH_3$; and
$R_3$ represents hydrogen, $C(O)H$ or $C(O)C_{2-10}$ alkyl; or
$R_1$ represents hydrogen, $C(O)H$ or $C(O)C_{1-10}$ alkyl;
$R_2$ represents hydrogen, $C(O)H$ or $C(O)C_{2-10}$ alkyl; and
$R_3$ represents $C(O)CH_3$; or $R_1$ represents hydrogen, $C(O)H$ or $C(O)C_{2-10}$ alkyl;
$R_2$ represents hydrogen, $C(O)H$ or $C(O)C_{1-10}$ alkyl; and
$R_3$ represents $C(O)CH_3$.

2. A pharmaceutical composition comprising a pharmaceutically acceptable carrier, a pharmaceutically acceptable diluent, a pharmaceutically acceptable excipient and/or a pharmaceutically acceptable adjuvant and a compound represented by formula (I):

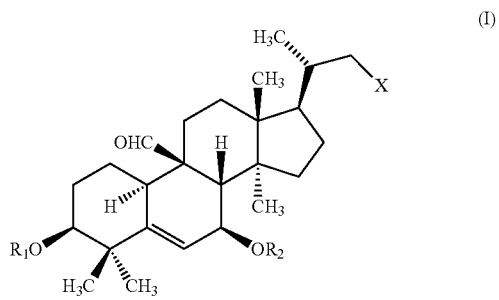

(I)

or a pharmaceutically acceptable salt thereof, wherein:

X represents:

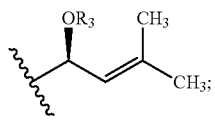

$R_1$ represents $C(O)CH3$;
$R_2$ represents hydrogen, $C(O)H$ or $C(O)C_{2-10}$ alkyl; and
$R_3$ represents hydrogen, $C(O)H$ or $C(O)C_{1-10}$ alkyl; or
$R_1$ represents $C(O)CH_3$;
$R_2$ represents hydrogen, $C(O)H$ or $C(O)C_{1-10}$ alkyl; and
$R_3$ represents hydrogen, $C(O)H$ or $C(O)C_{2-10}$ alkyl; or
$R_1$ represents hydrogen, $C(O)H$ or $C(O)C_{2-10}$ alkyl;
$R_2$ represents $C(O)CH_3$; and
$R_3$ represents hydrogen, $C(O)H$ or $C(O)C_{1-10}$ alkyl; or
$R_1$ represents hydrogen, $C(O)H$ or $C(O)C_{1-10}$ alkyl;
$R_2$ represents $C(O)CH_3$; and
$R_3$ represents hydrogen, $C(O)H$ or $C(O)C_{2-10}$ alkyl; or
$R_1$ represents hydrogen, $C(O)H$ or $C(O)C_{1-10}$ alkyl;
$R_2$ represents hydrogen, $C(O)H$ or $C(O)C_{2-10}$ alkyl; and
$R_3$ represents $C(O)CH_3$; or
$R_1$ represents hydrogen, $C(O)H$ or $C(O)C_{2-10}$ alkyl;
$R_2$ represents hydrogen, $C(O)H$ or $C(O)C_{1-10}$ alkyl; and
$R_3$ represents $C(O)CH_3$.

3. The pharmaceutical composition according to claim 2, wherein the pharmaceutically acceptable carrier is a liposome, a lipid microvesicle, a brown alga, a bladderwrack, a black wrack, a *Himanthalia* species or an *Undaria* species.

4. The pharmaceutical composition according to claim 2, wherein the pharmaceutical composition is a tablet, a capsule, a powder, a granule, a patch or a liquor.

5. A method for inhibiting cancer cell proliferation in a subject, comprising administering to a subject in need thereof a therapeutically effective amount of a compound represented by formula (I):

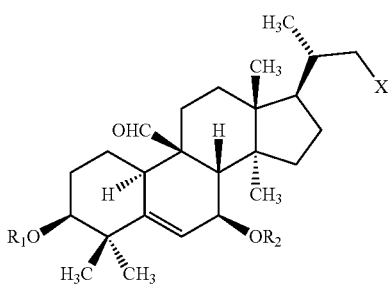

(I)

or a pharmaceutically acceptable salt thereof, wherein:

X represents:

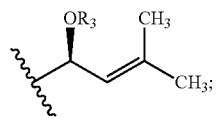

$R_1$ represents $C(O)CH_3$;
$R_2$ represents hydrogen, $C(O)H$ or $C(O)C_{2-10}$ alkyl; and
$R_3$ represents hydrogen, $C(O)H$ or $C(O)C_{1-10}$ alkyl; or
$R_1$ represents $C(O)CH_3$;
$R_2$ represents hydrogen, $C(O)H$ or $C(O)C_{1-10}$ alkyl; and
$R_3$ represents hydrogen, $C(O)H$ or $C(O)C_{2-10}$ alkyl; or
$R_1$ represents hydrogen, $C(O)H$ or $C(O)C_{2-10}$ alkyl;
$R_2$ represents $C(O)CH_3$; and
$R_3$ represents hydrogen, $C(O)H$ or $C(O)C_{1-10}$ alkyl; or
$R_1$ represents hydrogen, $C(O)H$ or $C(O)C_{1-10}$ alkyl;
$R_2$ represents $C(O)CH_3$; and
$R_3$ represents hydrogen, $C(O)H$ or $C(O)C_{2-10}$ alkyl; or
$R_1$ represents hydrogen, $C(O)H$ or $C(O)C_{1-10}$ alkyl;
$R_2$ represents hydrogen, $C(O)H$ or $C(O)C_{2-10}$ alkyl; and
$R_3$ represents $C(O)CH_3$; or
$R_1$ represents hydrogen, $C(O)H$ or $C(O)C_{2-10}$ alkyl;
$R_2$ represents hydrogen, $C(O)H$ or $C(O)C_{1-10}$ alkyl; and
$R_3$ represents $C(O)CH_3$.

6. The method according to claim 5, wherein the cancer cell is selected from the group consisting of a human leukemia cell U937, a human lung cancer cell A549, a human glioblastoma cell U87-MG, a human liver cancer cell Mahlavu, a human colorectal cancer cell SW-480, a human breast cancer cell MDA-MB-231 and a human breast cancer cell MDA-MB-468.

* * * * *